US006227202B1

(12) United States Patent
Matapurkar

(10) Patent No.: US 6,227,202 B1
(45) Date of Patent: May 8, 2001

(54) METHOD OF ORGANOGENESIS AND TISSUE REGENERATION/REPAIR USING SURGICAL TECHNIQUES

(75) Inventor: Balkrishna Ganpatrao Matapurkar, New Dehli (IN)

(73) Assignee: Maulana Azad Medical College, New Dehli (IN)

( * ) Notice: Subject to any disclaimer, the term of this patent is extended or adjusted under 35 U.S.C. 154(b) by 0 days.

(21) Appl. No.: 08/921,307

(22) Filed: Aug. 29, 1997

(30) Foreign Application Priority Data

Sep. 3, 1996 (IN) .............................. 1959DEL96

(51) Int. Cl.[7] .................................................. A61B 19/00
(52) U.S. Cl. .......................................... 128/898; 623/11.11
(58) Field of Search ...................... 128/898; 623/11.11, 623/23.64, 23.65, 23.66, 23.71, 23.72, 23.76

(56) References Cited

PUBLICATIONS

1994, Alberts, Bruce; Dennis Bray; Julian Lewis; Martin Raff; Keith Roberts and James D. Watson, *Molecular Biology of The Cell*, 3rd ed. Garland Publishing, Inc. New York, NY, 1994, p. 32–40, 1037–1066, 1067–1102, 1103–1137, 1139–1146, 1147–1162, 1163–1193.

1982, Ansari, Amir H., Kenneth Gould, and Richard J. Turner, *Obstetrics & Gynecology*, "Uterine Horn Replacement", v. 60, n. 6, p. 733–737, Dec. 1982.

1995, Berry, C.L. *Progress in Pathology*, "The Molecular Basis of Development", v. I, ed. Nigel Kirkham, p. 121–132, 1995.

?, J.P. Blandy, M. Singh and G.C. Tresidder, *British Journal of Urology*, "Urethroplasty by Scrotal Flap for Long Urethral Strictures", p. 261–267.

Boyarsky, Saul and Oscar Duque, *The Journal of Urology*, "Ureteral Regeneration in dogs: an experimental study bearing on the Davis intubated ureretotomy", v. 73, n. 1, p. 53–61, Jan. 1955.

Dadoukis, John D.; Spiros Th. Papayramidis; George N. Karavelas; Anastasios P. Aidonopoulos; and Homer A. Aletras; *Eur. J. Surg.*, "Pedicle Grafts of Peritoneum and Transversals Muscle for the Repair of Large Defects in the Duodenal Wall", v. 159 31–33, 1993.

P.G. Duffy; P.G. Ransley; P.S. Malone; and P. van Oyen, *British Journal of Urology*, "Combined Free Autologous Bladder Mucosa/Skin Tube for Urethral Reconstruction: and Update", v. 61, p. 505–506, 1988.

1988, Elkins, Thomas E.; Charles Drescher; J.O. Martey and David Fort, *Obstetrics& Gynecology*, "Vesicovaginal Fistula Revisited", v. 72, n. 3, part 1, p. 307–312, Sep.

1992, Elkins, Thomas E.; T.S. Ghosh; G.A. Tagoe and Robert Stocker, *Obstetrics & Gynecology*, "Instruments & Methods: Transvaginal mobilization and utilization of the anterior bladder wall to repair vesicovaginal fistulas involving the urethra", v. 70, n. 3, p. 455–459, Mar. 2092.

Enwemeka, C.S.; *Tissue and Cell*, "Membrane–Bound Intracellular Collagen Fibrils in Fibroblasts and Myofibroblasts of Regenerating Rabbit Calcaneal Tendons", v. 23 n. 2, p. 173–190, 1991.

(List continued on next page.)

*Primary Examiner*—Dinh X. Nguyen
(74) *Attorney, Agent, or Firm*—Merchant & Gould P.C.

(57) ABSTRACT

An in vivomethod of organogenesis of various tissues and/or organs in a mammalian body, comprising surgically transferring autogenous peritoneum containing stem cells to a place in the body where the desired tissue or organ is to be regenerated or repaired.

39 Claims, 31 Drawing Sheets

STRUCTURE OF NEPHROGENIC CORD

GUT
PERITONEAL LAYER
PARAMESONEPHERIC DUCT(1)
MESONEPHRIC DUCT(2)
MESONEPHROS(3)
GONAD(4)

OTHER PUBLICATIONS

Fazio, Victor W.; Ian T. Jones; David G. Jagelman and Frank L. Weakley, *Surgery, Gynecology & Obstetrics*, "Rectourethral Fistulas in Grohn's Disease", v. 164, p. 148–150, Feb. 1987.

Gilbauch, James H., Jr.; David C. Utz and Khalil G. Wakim, *Investigative Urology*, "Partial Replacement of the Canine Urethra with a Silicone Prosthesis", v. 7, n. 1, p. 41–51, 1969.

1981, Harris, Albert K., David Stopak and Patricia Wild, *Nature*, "Fibroblast Traction as a Mechanism for Collagen Morphogensis", v. 290, p. 249—249, Mar. 20, 1998.

Harrison, D.H., *British Journal of Plastic Surgery*, "Reconstruction of the Urethra for Hypospadiac Cripples by Microvascular Free Flap Transfers", v. 39, p. 408–413, 1986.

Harrison, R.G., *Cunningham's Text Book of Anatomy*, "introduction to human embryology", reprint ed. 1991.

Hendren, W. Hardy and K. Kenney Crooks, *The Journal of Urology*, "Tubed Free Skin Graft for Construction of Male Urethra", v. 123, p. 858–861, Jun. 1980.

Holder, Nigel, *Development*, "Organization of Connective Tissue Patterns by Dermal Fibroblasts in the regenerating axolotl limb", v. 105, p. 585–593, 1989.

Hübner, I. Rurka, P. Porpaczy and I. Miko, *Orological Research*, "Antologous Everted Vein Graft for Repairing Long–section Urethral Defects", c. 19, p. 131–134, 1991.

Imai, Tamaki; Toshio Kubo and Hidenobu Watanabe; "Chronic Gastritis in Japanese with Reference to High Incidence of Gastric Carcinoma", before 1971.

Jonkman, Marcel F.; Frank M. Kauer; Paul Niewenhuis and Izaak Molenaar, *Artificial Organs*, "Segmental Uterine Horn Replacement in the Rat Using a Biodegradable Microporous Synthetic Tube", V. 10, n. 6, 475–480, 1986.

Juan, Rosai, ed.; *Ackerman's Surgical Pathol*, v. II, pp. 1635, 1638 and 1661; 1989.

1989, Khoury, A.E.; M.E. Olsen; G.A. McLorie and B.M. Churchill, *American Urological Association, Inc.*, "Urethral Replacement with Tunica Vaginalis: a pilot study", p. 628–630.

Kiricuta, I. and A.M.B. Goldstein, *The Journal of Urology*, "The Repair of Extensive Vesicovaginal Fistulas with Pedicled Omentum: a review of 27 cases", v. 108, p. 724–727, 1972.

1955, Lapides, Jack and Eldon L. Caffery, *The Journal of Urology*, "Observations on Healing of Ureteral Muscle: relationship to intubated ureterotomy", v. 73, n. 1, p. 17–52, Jan. 1985.

Lazarus, Hilda M., *The Journal of Obstetrics & Gynaecology*, "Urinary Fistulae in Women with Special Reference to their Operative Technique", v. X, n. 1, p. 1–11, Sep. 1959.

Louagie, Y., A. Legrand–Mousier, C. Remacle, P. Maldague, L. Lambotte and R. Pontot, *Res. Experimental Medicine*, "Morphology and Fibrinolytic Activity of Canine Autogenous Mesothelium Used as Venous Substitute", v. 180, p. 239–347, 1986.

1984, Lugo, Miguel and Paul B. Putong, *Arch Pathol Lab Med*, "Metaplasia: an overview", v. 108, p. 185–189, Mar. 2084.

Medline Abstract; Department of Surgery, UCLA School of Medicine, *Urol.Res*. "Patch Grafting the Renal Pelvis and Ureteropelvic Junction. A Comparative Study in Pigs Using Lyophilized Dura Matter and Free Peritoneum", v. 16, n. 1, 37–41, 1988.

Medline Abstract; Ghrib, M., *Z–kinderchir*, "Bridging Extensive Esophageal Atresias by a Peritoneal Transplant", v. 41, n.2 p. 81–85, Apr. 1986.

Medline Abstract; Van Cangh, P.J.; G. Lagneaux; A. Abi–Aad; F. Lorge; R.J. Opsomer and F.X. Wese, *Eur. Url.*, "Muscle Regeneration after Edoureteropyelotomy", v. 22, n. 3, p. 241–246, 1992.

Medline Abstract; Wessells, H. and J.W. McAninch, *J. Urol.*, "Use of Free Grafts in Urethral Stricture Reconstruction", v. 155, n. 6, p. 1912–1915, Jun. 1996.

Macasaet, Milagros; Therese Lu and James H. Nelson; *Am. J. Obstet. Gymnecol.*, "Ureterovaginal Fistula as a Complication of Radical Pelvic Surgery", v. 124, n. 7, p. 757–760, Apr. 1, 1976.

Olsen, Leif; Staffan Bowald, Christer Busch, Johan Carlsten and Ingvar Eriksson, *Scand J. Urol. Nephrol*, "Urethral Reconstruction with a New Synthetic Absorbable Device", v. 26, p. 323–326, 1992.q.

O'Neill, J.J., *American Journal of Obstetrics and Gynecology*, "The use of the vermiform appendix as a Fallopian Tube", v. 95, n 2, p 219–221, May 15, 1996.

Openheimer, Rudolf and Frank Hinman, Jr., *The Journal of Urology*, "Ureteral Regeneration: Constracture vs. Hyperplasia of smooth muscle", v. 74, n. 4, p. 476–484, Oct. 1955.

Prasad, Leela M., "York Mason Procedure for Rectourethral Fistula or Benign Tumor", *Mastery of Surgery*, ed. Dr. Nyhus, v. 2, 2nd ed., ch. 135, 1993.

Royce, P.I., P.I. Zimmerman and J.B. deKernion, *Urological Research*, "Patch Grafting the Renal Pelvis and Ureteropelvic Junction: A comparative study in pigs using lyophilized dura mater and free peritoneum", v. 16, p. 37–41, 1988.

Sadler, T.W. ed., *Longman's Medical Embryology*, "Urogenital System", Williams & Williams, Baltimore, 1995, p. 272–311.

Schmid, Peter; David Cox; Grawme Bilbe; Rainer Maier and Gary K. McMaster, *Development*, "Differential Expression of TGF $\beta1$, $\beta2$ and $\beta3$ Genes Duging Mouse Embryogenesis", v. 111, p. 117–130, 1991.

1976, Singh, Inderbir, *An Introduction to Human Embryology for Medical Students*, 5th Ed. S.G. Wassani for Macmillan India Limited, Madras, India, 1991, p. 288–296.

Thüroff, J.W.; G. Hutschenreiter; D. Frohneberg and R. Hohenfellner, *Eur. Urol*. "Transplantation of a Free Peritoneal Patch in Surgery of the Renal Pelvis and Ureter", v. 7, p. 304–311, 1981.

Turner–Warwick, *British Journal of Urology*, "The Use of Pedicle Grafts in the Repair of Urinary Tract Fistulae", v. 44, p. 644–656, 1972.

Trump, Benjamin; Elizabeth M. McDowell; Fred Glavin; Lucy A. Barrett; Peter J. Becci; Walter Schürch; Hans E. Kaiser and Curtis C. Harris; *J. Natl. Cancer*, "The Respiratory Epithelium. III. Histogenesis of Epidermoid Metaplasia and Carcinoma In Situ in the Human", v. 61, n. 2, p. 563–575, Aug. 1978.

Weaver, Robert G., *Surgery, Gynecology & Obstetrics*, "The Effect of Large Caliber Splints on Ureteral Healing", p. 590–594, Nov. 1956.

Wood, Thomas W. and Richard G. Middleton, *Urology*, "Single–Stage Transrectal Transsphincteric (Modified York–Mason) Repair of Rectourinary Fistulas", v. XXXV, n. 1, p. 27–30, Jan. 1990.

INTRA EMROYNIC MESODERM

TRANSVERSE SECTION OF EMBRYO '5mm'

STRUCTURE OF NEPHROGENIC CORD

FORMATION OF PARAMESONEPHRIC DUCT
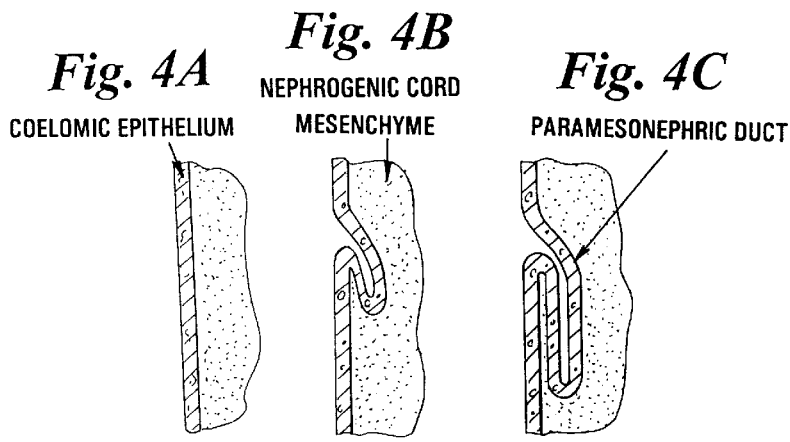
Fig. 4A COELOMIC EPITHELIUM
Fig. 4B NEPHROGENIC CORD MESENCHYME
Fig. 4C PARAMESONEPHRIC DUCT
Fig. 5
FORMATION OF UTERO-VAGINAL CANAL (STAGE-I)
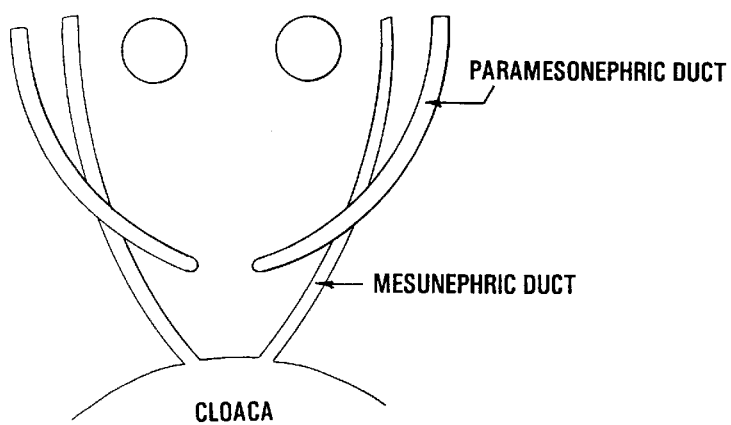
Fig. 6
FORMATION OF UTERO-VAGINAL CANAL (STAGE-II)
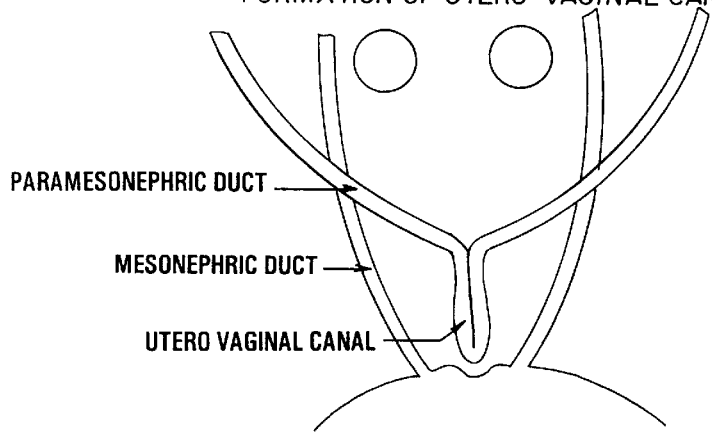

REGENERATION OF URETER

TO URINARY BLADDER

INTRAVENOUSPYELOGRAPHY (IVP)
OF DOG AT 6 MONTH

INTRAVENOUSPYELOGRAPHY (IVP)
OF DOG AT 12 MONTH

REGENERATION OF FALLOPIAN TUBE

REGENERATION OF UTERUS

A. PRIOR TO SEX DIFFERENTIATION

B. AFTER SEX DIFFERENTIATION

A. SAGITAL SECTION OF EMBRYO

B. DORSAL VIEW OF URINARY BLADDER

Fig. 49 URINE FLOW CHART (5 YEARS OF POST OPERATIVE)

| | | |
|---|---|---|
| VOIDED VOLUME | (V) = | 396 ml |
| MAXIMUM FLOW RATE | (QMAX) = | 41.5 ml/s |
| VOLUME AT MAX. FLOW | (VQMAX) = | 53 ml |
| TIME TO MAX. FLOW | (TQMAX) = | 1 s |
| FLOW TIME | (T) = | 22 s |
| AVERAGE FLOW RATE | (QAVE) = | 17.7 ml/s |

DIAGRAMABLE REPRESENTATION OF DEVELOPMENT OF ABDOMINAL WALL

ECTODERM
MESODERM
ENDODERM

DERMATOME
MYOTOME
SLEROTOME

DERMATOME
MYOTOME
SPINAL NERVE
MESENCHYMAL VERTABRAL BODY

DERMIS FROM DERMATOME
UGC
UGC
MYOTOME

METHOD OF ORGANOGENESIS AND TISSUE REGENERATION/REPAIR USING SURGICAL TECHNIQUES

FIELD OF THE INVENTION

The present invention relates to organogenesis, i.e., repair or regeneration of various tissues and organs in a patient's body from autogenous stem cells. This invention is preferably employed to regenerate organs such as ureter, fallopian tube, uterus, urethra and aponeurosis. The term 'Patient' includes mammals including human beings.

PRIOR ART OF THE INVENTION

In plant life and lower animals, regeneration capacity of various tissues and organs is present, for example, regeneration of lens and heteromorphic regeneration of antenna in place of amputated eye is possible in lower forms of life such as insects. However, in higher forms of life such as mammals including human beings, this is negligible or absent.

In the literature, in the past, regeneration of organs in mammals have been attempted and studied. A few examples of such prior art are given here below.

Earlier, experiments were conducted on Blood Vessels, Duodenum defects, oesophagus ect. and the following prior art are worth to be quoted:

Luagie. D. Y. et al. Morphology & Fibrinotylic activity of canine (Dogs) autogenous mesothelium used as venous substitute. Res. in Exp. Med 1986=186=239–247.

Dadaukis J. D. et al. Pedicle graft of Peritoneum and Transversalis muscle for repair of large defects in duodenal wall (in pigs). Eur.J. Surg. 1993=159=31–33.

Gharib M Bridging extensive oesophageal atresias by peritoneal transplant Z. Fur. Kinderchir 1986=41 (2)=81–85.

Ureter

Boyarsky S and Duque O—Ureteral regeneration in god an experimental study bearing on Davis intubated ureterotomy. The J. of Urology 1955=73 =53–61.

Oppenheimer R F. Hinman. F. Jr. Ureteral regeneration: Contracture Vs Hyperplasia of smooth muscles. The J. of Urol. 1955=74=476–484.

Lapidis J, Caffery E. J. Observations on healing of ureteral muscle: Relationship to intubated ureterotomy, The J. of Urol. 1955=73=47–52.

Similarly,—Thuroff J W et al. attempted free peritoneal patch graft in surgery of Renal Pelvis and Ureter. The free patch was used from anterior abdominal wall. Eur.Urol. 1981=7==304–311.

Royce P. L. et al. used patch grafting of renal pelvis and uretero-pelvic junction using Lyophilised dura and free peritoneum from adjacent peritoneal envelope for grafting purpose. Urol. Res. 1988=16=37–41.

Ureter has the capacity to regenerate as studied by Boyarsky 1955; Operneimer 1955 and Lapidis of 1955. The window made in the wall of ureter by these researchers was small (0.5 to 2 cms) in size. These workers could not comment whether the regeneration was true or scar contraction was responsible for spreading adjacent wall.

Unfortunately, the above prior arts failed to regenerate the required components of organs and tissues of the ureter.

Fallopian tube and Uterus:—

Fallopian tube is a tube which conducts ovum from ovary to the uterus and also helps in fertalisation of the ovum in its lumen. The uterus is a part of reproductive system in mammals and it provides the congenial atmosphere for the growth and development of embryo.

The tubal plastic surgery has witnessed use of various tissues indicating the interest in the area of infertility problems in females. The tissues used are vermiform appendix human umbilical vein (in rabbits) seromuscular ileal grafts, ileum, venous and arterial homografts, allontoic membrane, human chorion-amnion etc with variable success rates. Biodegradable synthetic microporous artificial vascular grafts showed excellent healing characteristics. Despite notable improvement in overall results of tuboplasty a suitable method is still needed for replacement of part of whole of the oviduct to correct extensive damage of the fallopian tube.

In a prior art namely, "Use of PTFE (Poly Tetra Fluro Ethylene) and Biodegradable microporous synthetic tube as uterine horn graft in rats". Jonkman M F et al. Artif. Organs. 1986=10=475–480, the above matierals have been used for healing and regeneration of endometrium of uterus and fallopian tube.

The microsurgical reconstruction of Fallopian tube studies by Gauwerky and others showed regeneration of mucosa. Hum. Reprod. 1994=9(11)=2090–2102 and Zentral bl Gynakol. 1994=116(3)=173–178.

The ciliogenesis after salpingostomy of rabbit has been observed by Vasquez et al Eur.J.Obst. Gynaecol. Reprod. Biol. 1984=18=103–118.

In these prior art experiments, though they observed the growth of certain kinds of cells/layers, none of them proposes or even envisages the complete regenertion of all the tissues/organs in toto. In other words, no prior art so far suggests or shows the regeneration of all the compounds of the organ. Therefore, till date, there is no clear evidence or proof to establish the regeneration of the entire organ or the desired parts of it.

OBJECTS OF THE INVENTION

To overcome the existing restrictions, the inventor, for the first time has regenerated the entire organ or the desired parts of it in mammals including human beings.

Hence, the main object of the present invention relates to organogenesis and tissue regeneration in live mammals including human beings.

Another object of the invention is to eliminate the problems of organ transplantation such as non-availability of organs, rejection of transplanted organs by recipient host, life long use of immunosuppresents by the recipient, need of perfect tissue matching etc. In other words, organ transplantation though a successful process, is plagued by rejection phenomenon which needs life long use of immunosuppresent. This not only increases the cost but jeopardizes the immunity as well. Non-availability of suitable donor, preservation and transportation of organ are a few other problems.

One more object of the invention relates to effective management of diseases of organs.

Yet another object of the invention is to provide a cost effective method of regeneration of organ without any need for external donor such as live or brain-death person.

Still another object of the invention relates to use of autogenous tissues so that the use of immunosuppresents are eliminated to prevent rejection phenomenon common in organ transplant surgery.

Further object of the invention provides the 'desired metaplasia' of tissues i.e providing useful transformation of one tissue into required tissue(s) in the region.

Yet another object of the invention is for providing regeneration or repair of organ/tissue employing stem cells.

One more object of the invention relates to the regenertion or repair of various organs/tissues of the body employing relevant stem cells from autogenous tissues present in various parts of the body.

Still another object of the invention relates to regeneration of organs/tissues by surgically transferring stem cells to the region of the organ/tissue system where regeneration is required.

Furthermore, the invention relates to regeneration of ureter, fallopian tube, uterus, urethra and aponeurosis from the embryonic contiguous regions of peritoneum.

One more object of the presnte invention relates to regeneration/repair of uro-rectal septum from the embryonic contiguous segment of peritoneum.

Another object of the invention relates to surgically treat genito-urinary rectal diseases.

SUMMARY OF THE INVENTION

The above objects of organogenesis are achieved by using stem cells, which involves an in vivo and in situ method of organogenesis or various tissues/organs in an animal or human body, said method comprising surgically transferring autogenous peritoneum containing stem cells to a place in the body where the desired tissue/organ to be regenerated or repaired.

DETAILED DESCRIPTION OF THE INVENTION

The invention is centered around the realization of the principle that when single cell, i.e., fertilized ovum could produce the entire body comprising different kinds of tissues and organs performing innumerable functions, why then the stem cells of the developed tissues having pluripotent nature in the developed body should not form the desired tissues and organs. Keeping the above principle in mind, the inventor, after much research, has now regenerated many organs.

Embryological principle underlying the invention.

Basic laws of nature remain hidden by manifest world of nature. To unravel the laws of organogenesis, embryological principles are exactly similar. It is difficult to say which embryo will become fish, bird, mammal or man (Raff, R. A., Kaufman, T. C., Embryogenesis of evolution, New York, Macmillan. 'Molecular biology of the cell' edited by Alberts, B. et al; 2rd edition, 1994 Chapter 1, P. 32 and 33). Organogenesis exists in nature in plants and lower forms of life. It is absent or negligible in higher forms of life such as mammals and man. Multicellular bodies of higher life forms are formed by differentiation of and proliferation of embryonal primitive germ cells. In order to sustain complex life functions, the cell specialization has to be maintained and thus, organ regeneration capacity is compromised in higher forms of life due to specialization of stem cells (Molecular biology of the cell, edited by Alberts B. et al, 3rd edition, 1994 Chapter 21, P. 1037, Chapter 22 p.1141).

When the whole body is formed from a single celled fertilized ovum having totipotent character, why not the pluripotent stem cells from developed tissues should not form the tissues limited by its pluripotency. Many general Surgeons dealing with chronic peritonities cases observed abnormal changes in the abdominal cavity such as papillary formation, osseous change, acini formation etc. However, till date, no one realized and co-related the fact the abnormal metaplastic changes observed in chronic peritonities cases are limited to tissues developed from mesoderm layer of the embryo. Now, the inventor for the first time co-related the abnormal changes of peritoneum by its embryonal origin i.e. any metaplastic change in peritoneum will result in tissues of mesoderm only since peritoneum is also of mesodermal in origin. In other words, peritoneum is formed form mesodermal germ layer which in turn can undergo metaplastic change to form tissues developed from mesodermal germ layers only, for example, muscles, smooth muscles, blood vessels, bones. Moreover, the inventor has never observed, during his various experiments, any metaplastic changes into formation of other germ layer tissues derived from ectodermal or endodermal layers. That is, mesodermal tissue can only form tissues derived from mesodermal germ layer and not ecto or endodermal tissues. However, the inventor investigated in depth the reason for such histophathological changes and arrived at an inference that the tissue changes are limited by pluripotency of the germ layer limited by that germ layer only. After many experiments with faults and failures, embryonal principles were utilized to achieve the desired metalplasia of stem cells in the present invention. The view based on embryonal principle was planned and experiments were carried out in live animal models. Indeed, at the time of experiments, proper embryonal contiguous segments were identified and selected to develop the corresponding organs. The stem cells were searched in places where they are easily accessible/available in simplest forms and preferably, in a single stem celled layer for easy stimulation and induction of change to any desired way.

Exploitation of nature by man for human benefits is known since time immemorial. In other words, developments of organs from fertilized ovum and perpetuation of life is a natural phenomenon. The organs and tissues are developed in embryo from germ layers namely Ecto, Endo and Mesoderm. The totipotent cells of these germ layers are capable of developing different tissues and organs. Primitive stem cells exist in adult tissues as well. Proliferation and differentiation for tissue repair and replacement of lost cells is their nature. If this property of stem cells can be exploited surgically, a desired metaplastic transformation can be achieved and the any required tissues and organs can be developed in the body.

In other words, the primitive life and lower animals found in nature have tissue regeneration capacity and can replace the lost part of their body. In higher animals, however, it is absent or negligible. The germ layers, the ecto, ento and mesoderm are distinct sheet of cells in early development of embryo. Each layer separately or in combination forms different tissues.

In the embryo, the perfect development of tissues and organs is dependent upon the following factors:

1. Cell movements—which enables the cells to reach the desired location in the embryo. In case, the required cell movements are hampered or affected, normal growth of the embryo is equally affected.
2. Duration of development of tissues and organs, i.e. providing sufficient time period which is essential for the formation of viable and functional tissues/organs in the embryo.
3. Location of the tissues or organs in the embryo.
4. Region surrounding the site or location of the tissues or organs.
5. Cell fate, i.e, the outcome of the cells in differentiation and proliferation proliferation of the cells. The cell fate again depends on (a) intrinsic factor—which means the cell code or messenger genes present in the cells and (b) extrinsic factors—which are tissue organisers responsible for induction of change in the cells (inducers) and limit the change in the cells (inhibitors). Thus, the cells undergo the change in a calculated and desired manner. That is, in given normal conditions the cellular differentiation and proliferation is in a well organized fashion.

6. Environmental factor—Such as radiation or drugs etc. which cause the cell damage. In other words, the changes in the cells indicate that the cells are capable of undergoing change, though they are destined to a particular function based on their inherent genetic coding.

7. Remote control influence of other tissues and organs in different regions of the embryo.

Apart from the above embryonic factors, the inventor has also realized that there are some beneficial properties inherent in the stem cells. The 'stem cells' are primitive cells which have not yet undergone differentiation, i.e., they possess the character of getting differentiated and multiply for specific purpose. These stem cells are present in the adult tissues and hence, hve the intrinsic capacity to differentiate and proliferate. Furthermore, the multiplication of stem cells occur in all directions and hence, the healing/repair of any tissue/organ takes place in a very short span of time.

In a developing embryo, the tissues and organs develop by cell migration to proper location in the embryo. The germ layer cells with totipotent nature in special locations undergo differentiation and proliferation governed by tissue organizers (inducers and inhibitors) The extent and limit of development of tissues and organs are also controlled by signals and control mechanisms of distant tissues and organs in the embryo coupled with functional need of the region and location (Alberts B et al, Molecular Biology of Cell, 3rd edition 1994, ch. 21 p.1037 and 1060 ch.22 p. 1141–94; Rosai, J., Ackerman's Surgical Pathol, 1989 Vol II ch.26, p.1638; Nieuwkoop P D., Wilhelm Roux Arch. Entwick. Lungs Mech. org. 1969=162=p.341–73).

It is now well established that vertebrate development is a process driven mainly by cellular interaction rather than direct genetic instruction. The process of development are capable of disturbances by environmental factors (Schmid P. et al, Development 1991=111=117, Berry C. L. The molecular Basis of development progress in Path. Vol. I, Ch.7, 1995 p.121–31).

The inventor has now applied these embryological principles to regenerate or repair the organs in the following manner:

The inventor has now selected the stem cells from autogenous tissues, for example, peritoneum for its inherent qualities to undergo change into different tissues, i.e. metaplastic transformation. Further, he has adopted an effective surgical technique thereby providing movement of such stem cells having the intrinsic capacity to undergo metaplastic transformation, to a site where the desired organ/tissue is to be regenerated. Furthermore, the inventor has also provided these stem cells a region/location of tissue system wherein the desired organ is to be regenerated or repaired. For example, shifting of peritoneal stem cells to urogenital system so that the construction or regeneration of ureter can be successfully achieved and thus, providing extrinsic factors of the region, for example, tissue organizers namely inducers and inhibitors. Therefore, in the present invention the required movement of stem cells is provided to the desired site. Moreover, the inventor provides the functional need of the new environment to the stem cells which further created demand/inducement to the shifted stem cells to undergo the desired change in the region, i.e., the desired metaplasia according to the inventor (metaplastic transformation being its property of peritoneal stem cells. In a typical case, for ureter regeneration, peritoneum from the contiguous embryonic site, i.e. from infra-umbilical region just anterior to caecum and ascending colon extending downward towards pelvis is transferred to excised ureteric region and anastomosed with proximal and distal cut ends of the ureter. Thus, exposing the graft to urinary system thereby creating a demand on the stem cells of the transferred graft to transform into the exact ureteric tissue.

In addition, the inventor provided sufficient/required duration of time for the development of the stem cells into viable and functional tissues. For example, in an embryo viable and functional tissue formation takes place in about three months time and keeping this time period in mind, the inventor in the present invention has provided at least three months time to the shifted stem cells to regenerate or repair the required organ or tissue. In other words, the inventor provided minimum three months time to the grafter peritoneum layers before removal of stent and performance of biopsy. However, the time period provided to obtain a viable and functional tissue/organ depends on case to case and the period indicated above should not be taken as to limit the scope of the invention.

In short, the inventor observed that the premature undifferentiated stem cells present in adult tissue maintain their pluripotency and are responsible for metaplasia if exposed to abnormal conditions or irritation. These cells even differentiate and proliferate on new pathways and also replace old cells. The basal metaplasia of endovervial glandlur epithelium is the best example. The metaplasia of fully differentiated cells is often abnormal and considered pathological. If the stem cells in the process of replacement of morphologically different cells are directed to desired metaplastic transformation, the tissue regeneration and organogensis is possible. Accordingly, the regeneration of ureter and other organs has been achieved by the inventor. In fact, the present invention envisages regeneration of ureter, fallopian tubes, uterus, aponeurosis and many other organs in vivo in mammals such as dogs, monkeys and human beings.

The scientific words used in the specification need some clarification. The abnormal transformation of adult fully differentiated tissues of one kind into fully differentiated tissues of another kind is termed "metaplasia" (Steadman's medical dictionary). This definition is same in most of the reference books.

Metaplasia commonly occur in different locations. The metaplastic change is important due to its clinical behaviour. It is responsible for diagnostic problems. Regeneration of lens and heteromorphic regenertion of antenna in place of amputated eye is possible. Numerous other studies on metaplasia of epithelium have been documented in cervix uteri, bronchus, oesophage-gastro-intestinal musosa urinary bladder, conjunctiva etc. (botinne C et al Cancer Res.1938=33=265; Cantin M. et al Am.J. Pathol. 1977=87=581; Imai T. et al. J. National Cancer Res.Int. 1971=47=179; Rosai J., Ackemans surg. Pathol 1989 vol.II p. 1968; Trump B F. et al. J Nat. Cancer Res. Inst. 1978=68=61=563). Tissue transformation and metaplasia arise from genetic expression of protein synthesis in cellular population (Lugo M. et al. Am. J. Clin. Pathol 1983=803 92). However, in the present invention, the fully differentiated tissue i.e the peritoneum has changed into fully differentiated tissue of the required organ such as ureter, fallopian tube, uterus, uro-rectal septum and aponeurosis (after the embryonic contiguous peritoneum has been surgically transferred to the required site or organ). But the change is not abnormal, on the contrary, it is desired morphologically and functionally in the region and therefore, the term "desired metaplasia" has been coined and used by the inventor in the present specification.

The development of all the components of the organ after it has been excised, suggests development of organ and hence, the term 'organogenesis' has been used in the present invention.

The metaplastic change of smooth muscle into juxtagmerular cells have been reported in ischaemic kidney (Cantin M. et al. Am. J. Pathol. 1977=87=581). However, only in the present invention, development of smooth muscle cell has been homogeneous and uniform and has similar pattern throught out the grafted peritoneal tube.

Peritoneum

After studying different body tissues, the inventor preferred the peritoneum because peritoneum consists of a single layered stem cells on a basement membrane. The presence of basement membrane helps in holding sutures very well. Further, the peritoneum traps large numbers of macrophages which in addition to their known phagocytic activity, also secrete a variety of physiologically active products such as prostaglandisn and leukotriences. Normal mesothelial cells of the peritoneum are a rich source of plasminogen and the fibrinolytic nature of these compounds prevents blood clots and facilitates absorption of body fluids.

Peritoneum is a wonder membrane. It has surface area equivalent to skin and has lot of properties which are still not utilized for human benefits. It has primitive stem cells on its basement membrane. Peritoneum is known to undergo metaplasia and forms papillary projections, pesudoacinin squamous nests and even cartilagenous nodules. Metaplasia transformation due to irritation is often reversible is the irritant is removed. Use of Peritonum as free graft and its nourishment has been tested in numerous animal experiments as on arterial patch graft. (Sterioff S. J R. Smith G. W. Am. Surg. 1472=38=53), in myringoplasty, intestinal anastomosis, for heart valve replacement, on stomach and pancreas as patch graft.

Peritoneum is a suitable material as it has strong basement membrane making it a very good sheet material and can hold sutures very well. The primitive stem cells of peritoneum are consistly engaged in replacing lost cells and tissues. The stem cells undergo proliferation differentiation and replace lost tissues. It takes active part in healing and produce conditions which help in healing by preventing infection and blood clot formation. In addition it has semipermeable property by which collection of excess serum etc. is absorbed (Matapukar et al World. J. Surg. 1991=15=768). these properties have prevented local infection and collection of inflammatory exudate. These properties of peritoneum have proved it to be an ideal material for the present invention.

Use of peritoneum has been reported in animal experiments as stated earlier (Dadaukis et al. Eur. J. surg.1993=153=31; Luagie D Y et al Res. in Exp. Med.1986=186=239). In humans, Gharib (Gharib. M. Z. Fur KinderChir. 1986=41(2)=81) has used peritoneal cylinder to bridge the defect of oesophageal atresia but failed to regenerate the wall of oesophagus; the peritoneal cylinder got contacted and ring was formed. The defect of oesophageal atresia may be due to the absence of tissue organizers during embryonic life. This may be the reason of non-development of oesophageal wall from the peritoneal cylinder used in oesophageal atresia cases. Absence of regional organizers failed to induce regenerative change in peritoneal stem cells. In addition, the peritoneal cylinder was not selected from the embryonic contiguous segment.

In another experiment, pedicle graft of peritoneum along with skeletal muscle (transverse abdominis of abdominal wall) were used for repair of large defects in duodenal wall in pigs (Dadaukis J. D. et al. Em. J. Surg. 1993=159=31). However, in this experiment the duodenal mucosa appeared similar to duodenum but smooth muscle layer was not developed. This may be due to presence of skeletal muscle with the peritoneum and hence, the local tissue organizers failed to have desired action on the graft and smooth muscle could not be developed. In dogs anterior wall of common illiac vein was replaced with (a) peritoneum with posterior rectus sheath, and (b) peritoneum without rectus sheath, and (c) mesentary. This revealed normal mesothelium only and no other component of the vessel wall regenerated. (Luagie D Y. et al Res. in Exp. Med. 1986=186=239). This may be due to the presence of rectus sheath. The peritoneum used may not be from representative contiguous embryonal segment. Royce et al. (Urol. Res. 1988=16=37). Using lyophilised dura and free peritoneum from adjacent peritoneal envelope for grafting renal pelvis and pelvis ureteric junction, failed to regenerate components of the wall of urinary tract. Change to transitional epithelium may be due to metaplastic reaction. As the kidneys develop in pelvic cavity and ascend to the lumbar region, the peritoneum of the adjacent peritoneal envelope may not be the representative embryonal segment of the peritoneum.

Earlier workers have observed that in the excised part of the ureter there appeared dense fibrosis and stricture in the region to the extent that even water could not be forced through the strictured tube. Microscopically mucosa was regenerated in the excised region but no development of other components of wall of ureter in the grafter peritoneal tube could not take place (Weaver R G., Surg. Gynae Obstet. 1956 Nov. p.590; Boyorashy S & Duque O., J. Urol. 1955=73=53; Oppenheimer R. Hinman, F. Jr. J. Urol. 1955=74=476; Lipides J. & Caffrey E L., J. Urol.1955=Vol.I p.17).

The potential of stem cells in the development of tissues and organs of the body in embryo is well known to the embryologists. The fertilized ovum, a single cell, is capable of forming the whole body with its different tissues and organs having different functions. This is based on sound principles of nature. In summary, the cell fate in embryo depends upon intrinsic and extrinsic cell factors, cell movements and tissue organizers, inducers or inhibitors. The other important factor being the timings of developments coupled with the functional need of the region where these cells have moved in embryo. Taking into consideration all these principles of nature, the present invention was planned and experimented in live animal models including human beings.

In other words, peritoneum has primitive stem cells. Mesoderm in the embryo forms gastrointestinal and urogenital systems. Intermediate cell mass of mesoderm in the embryo forms utogential organs. The lateral plate mesoderm forms peritoneum and the stem cells of peritoneum are engaged in proliferation and differentiation to regenerate and replace its lost cells. If stem cells of peritoneum are exposed to the environment of a particular organ/tissue system, the desired metaplastic transformation is a possibility. This may be due to the intrinsic capacity of the stem cells of the peritoneum to proliferate and differentiate, extrinsic local factor of the region, and the functional need of such tissue/organ. With this in mind, the present experiments have been performed on Mongrel dogs, monkeys and humans to explore the possibility of regeneration of many organs such as ureter, fallopian tube, uterus, uro-rectal septum, aponeurosis etc. from peritoneum.

The file of this patent contains at least one drawing/photo executed in color. Copies of this patent with color drawings/photos will be provided upon request and payment of the necessary fees.

The present invention is illustrated herebelow with reference to the accompanying drawings and such description and drawings should not be construed to restrict the scope of the invention. In the accompanying drawings:

FIG. 4 shows formation of paramesonephric duct in nephrogenic cord.

FIGS. 5 and 6 show formation of fallopian tube and utero vaginal canal from paramesonephric duct. Stage-I clearly shows the formation of utero-vaginal canal by the conversion of the two paramesonephric duct towards the centre. These two ducts then unite in the centre to form uterovaginal canal as shown in Stage-II.

Figure 7:
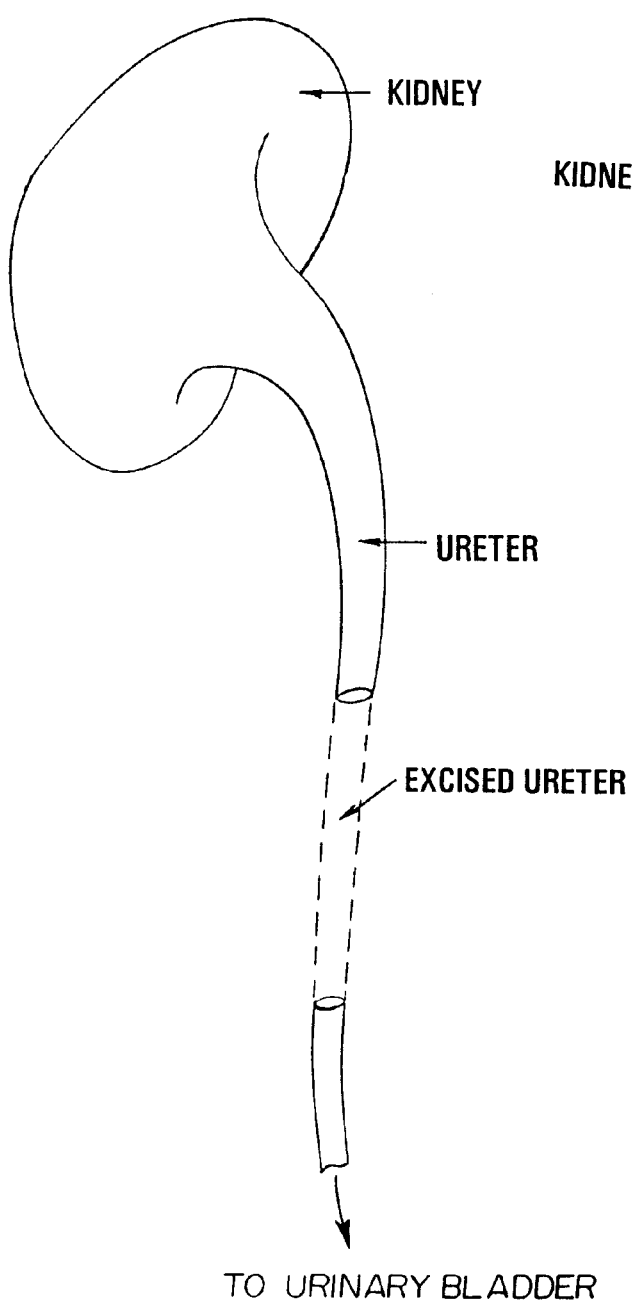
Figure 8:
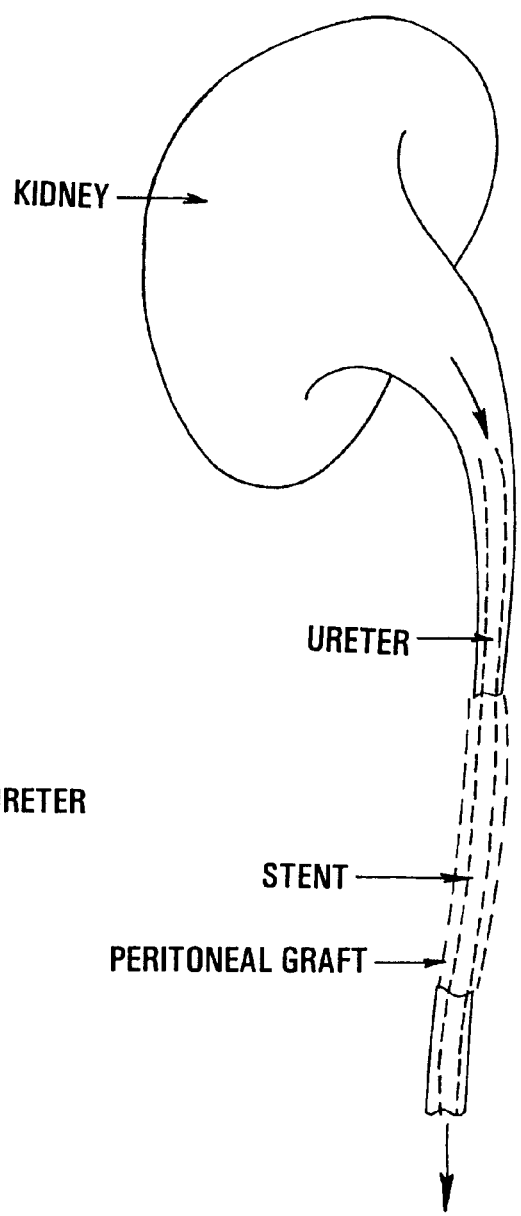

FIGS. 7 and 8 show diagramatic representation of regeneration of ureter as per invention.

Figure 9:
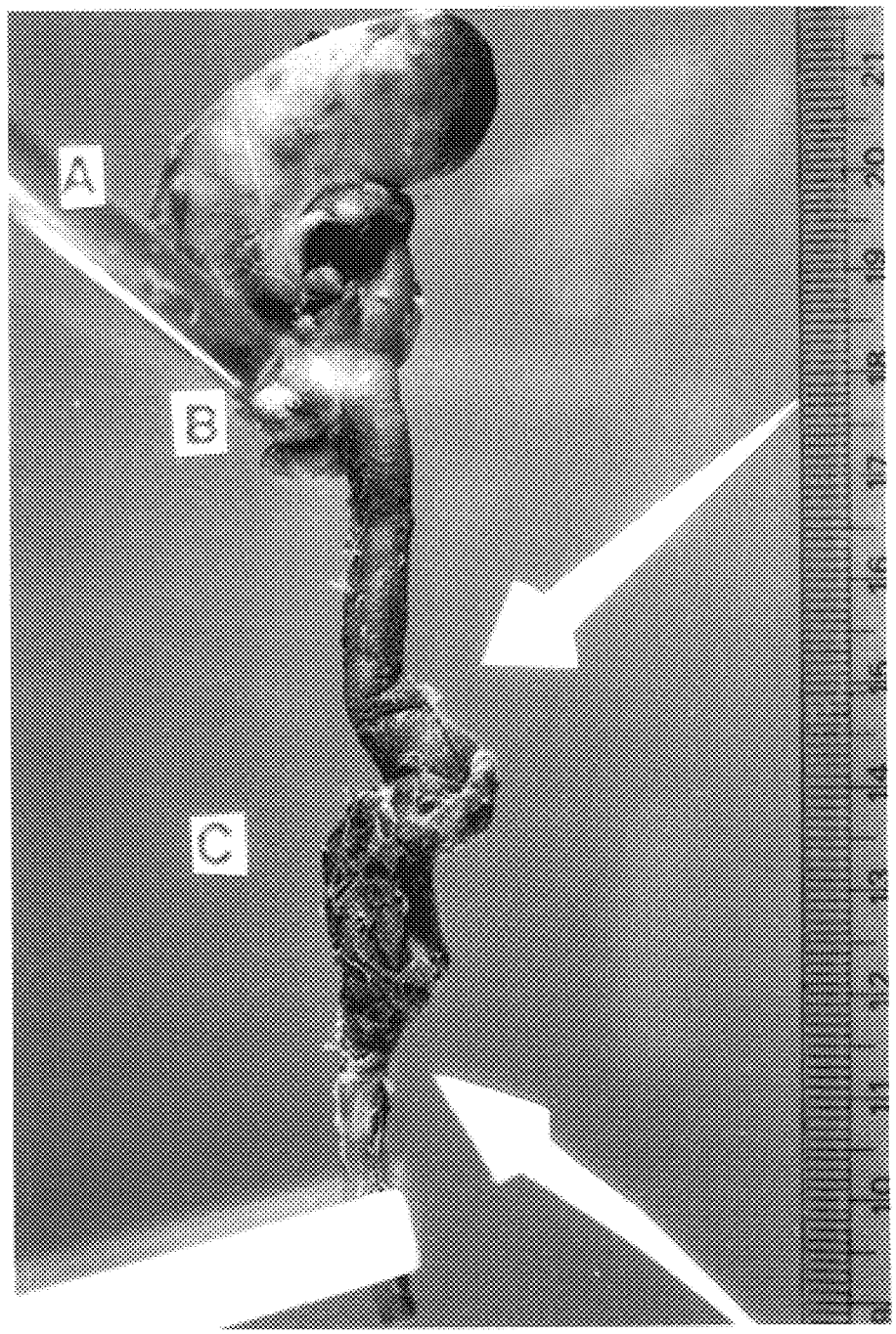
Figure 10:
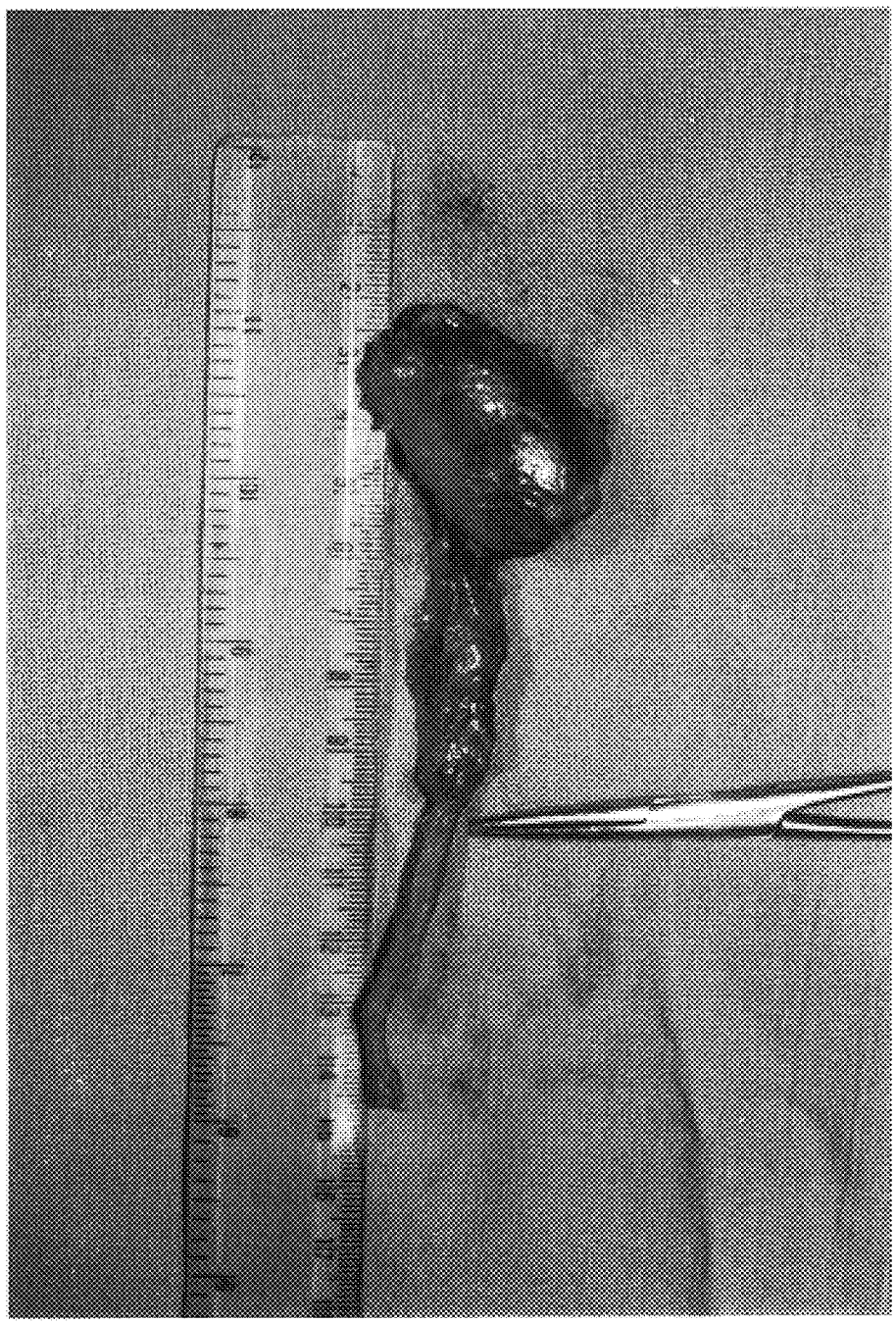

FIGS. 9 and 10 show regenerated ureter in gross at various regions of ureteric length in dog and monkey respectively.

Figure 11:
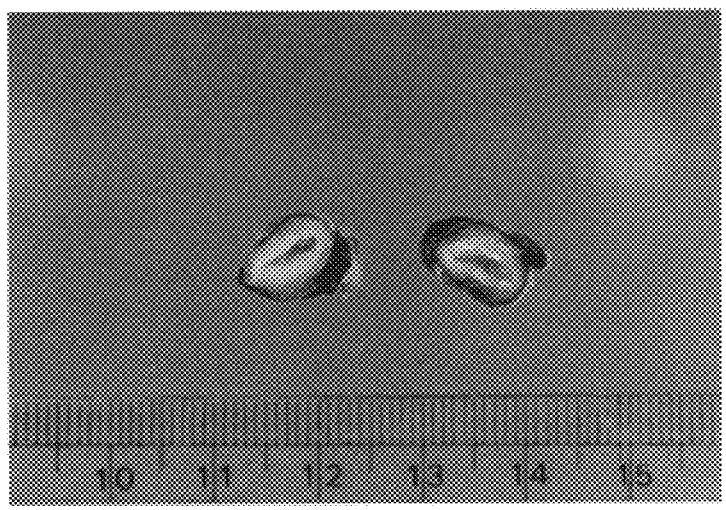
Figure 12:
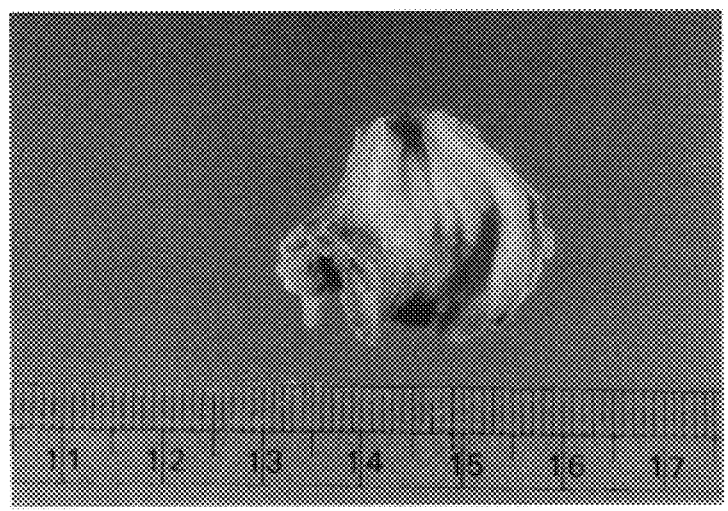
Figure 13:
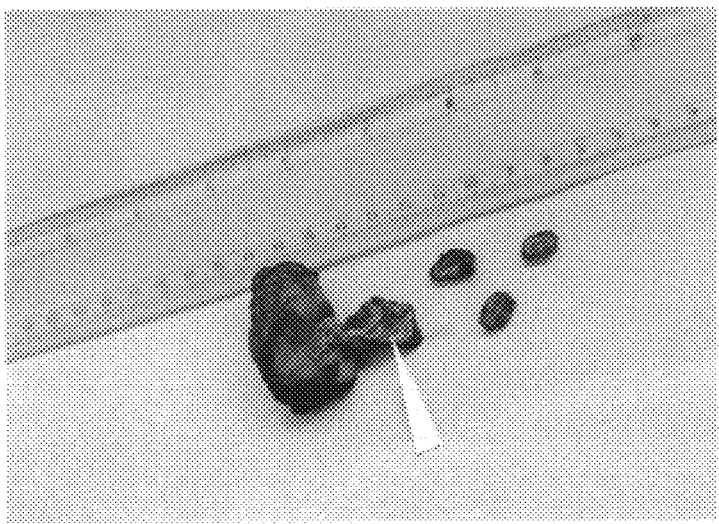

FIGS. 11, 12 and 13 show the transverse and longitudinal section of graft after 3 months of post operative period. The transverse sections of the graft clearly show the wall and well preserved lumen.

Figure 14:
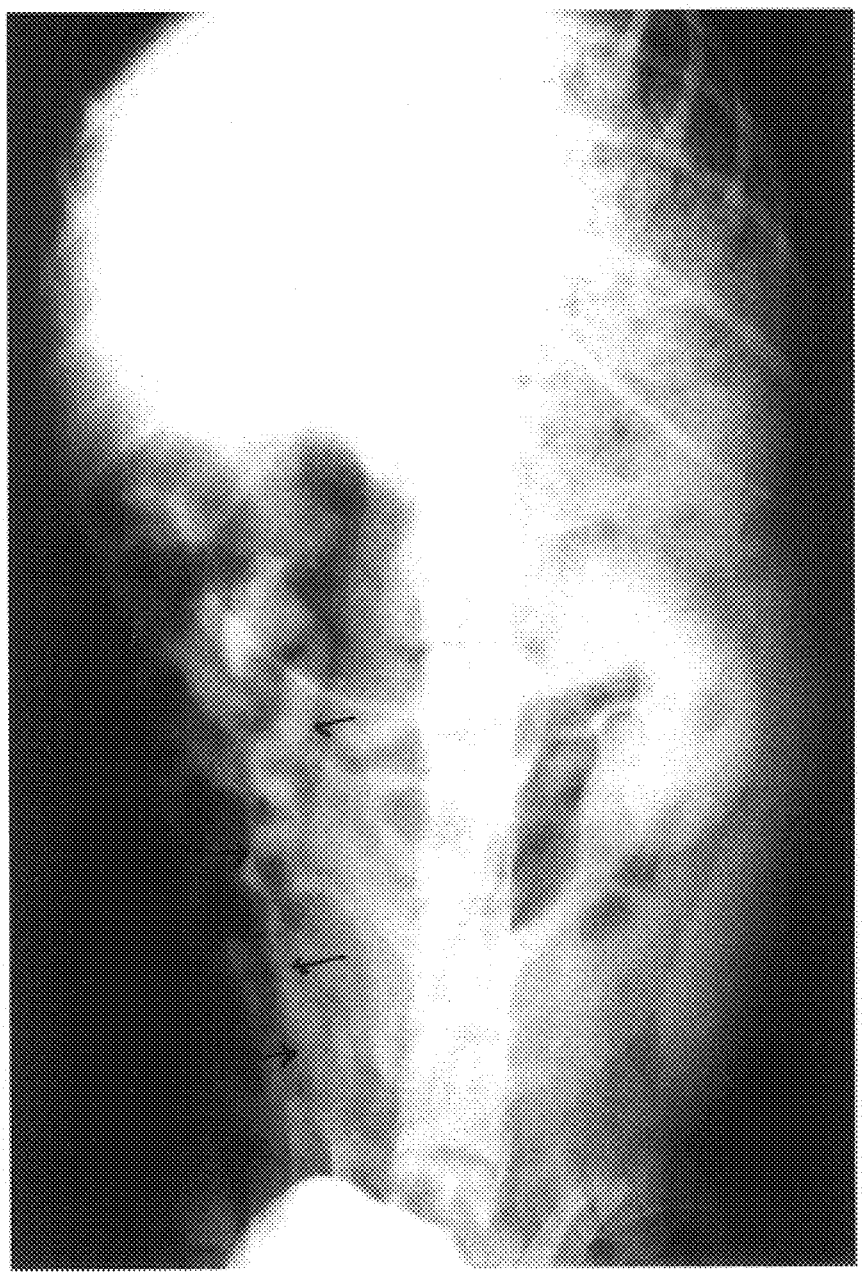
Figure 15:
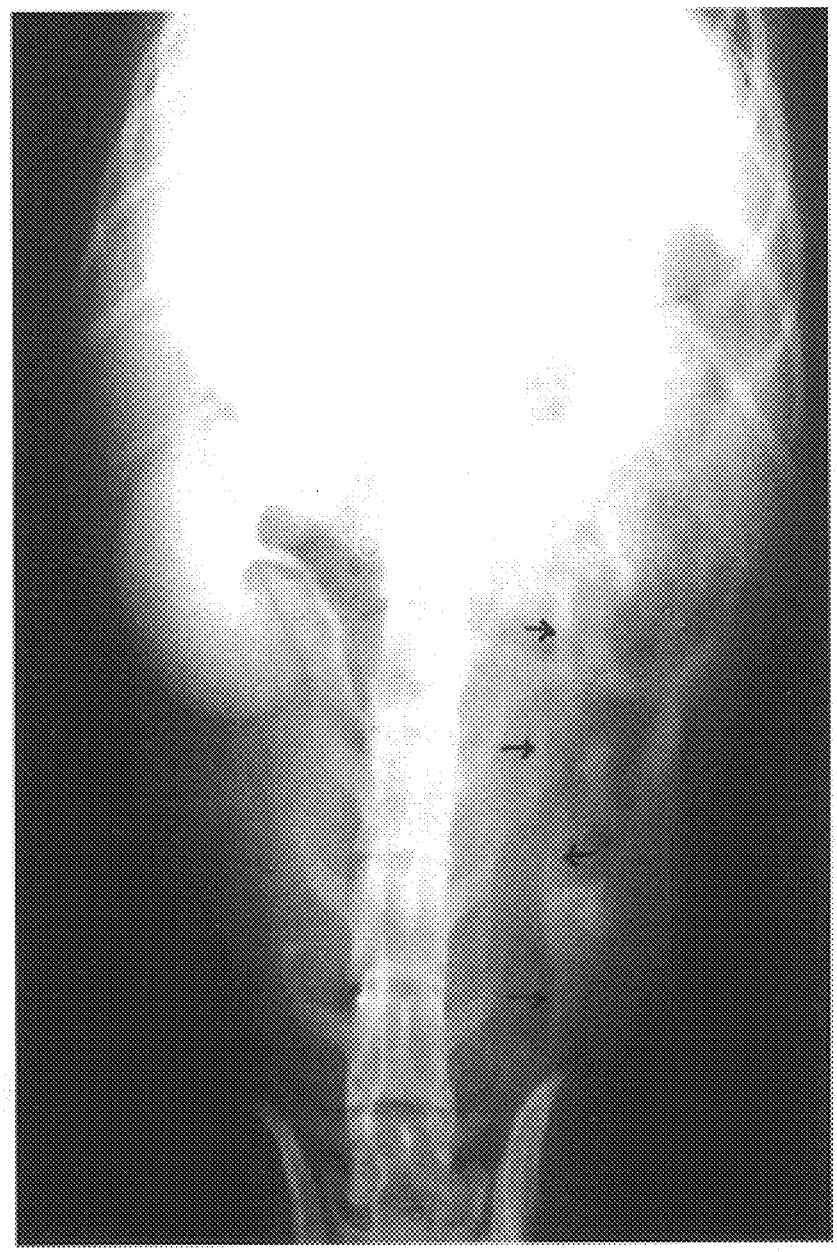

FIGS. 14 and 15 show Intravenouspyelography of dog taken at 6 and 12 months.

Figure 16:
Figure 17:
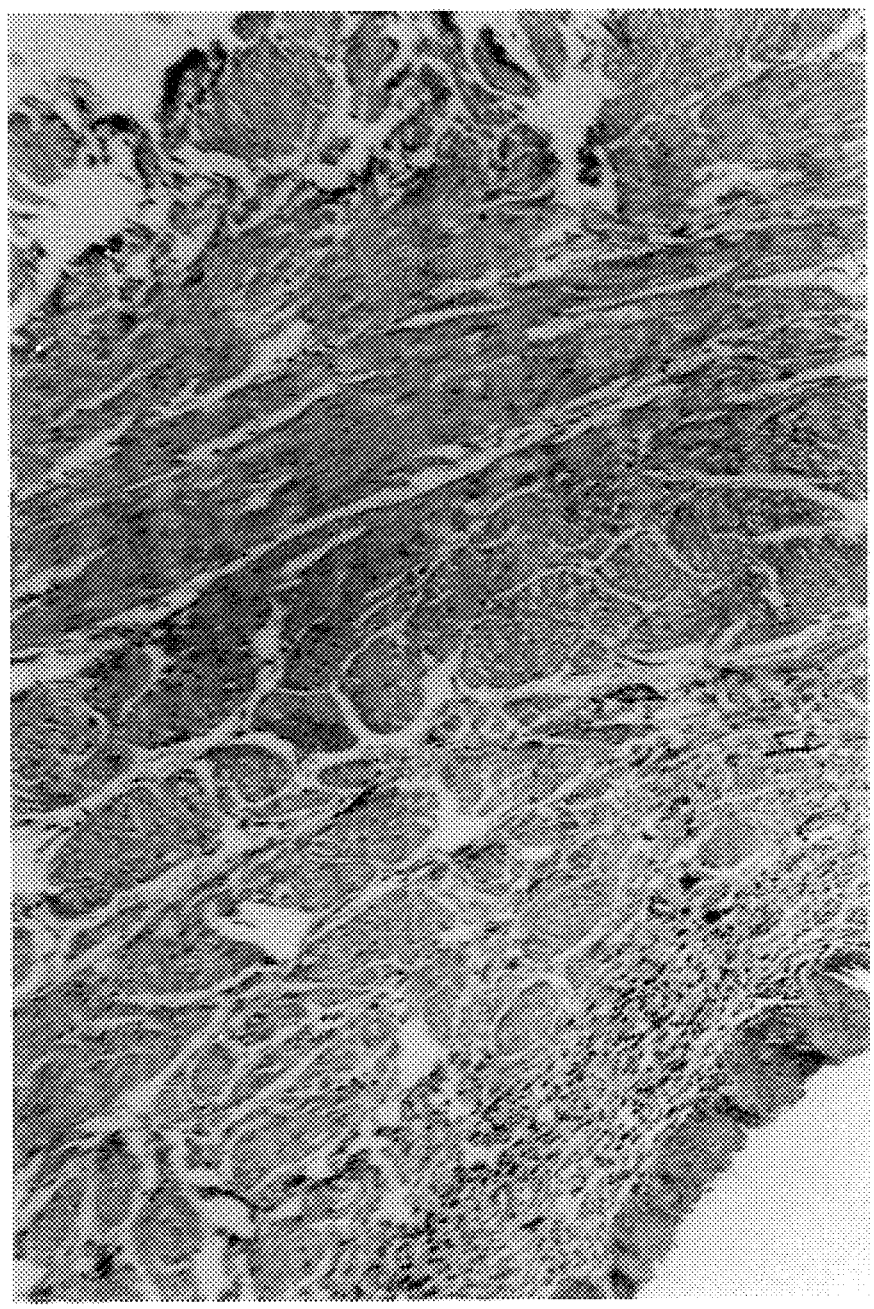
Figure 17A:
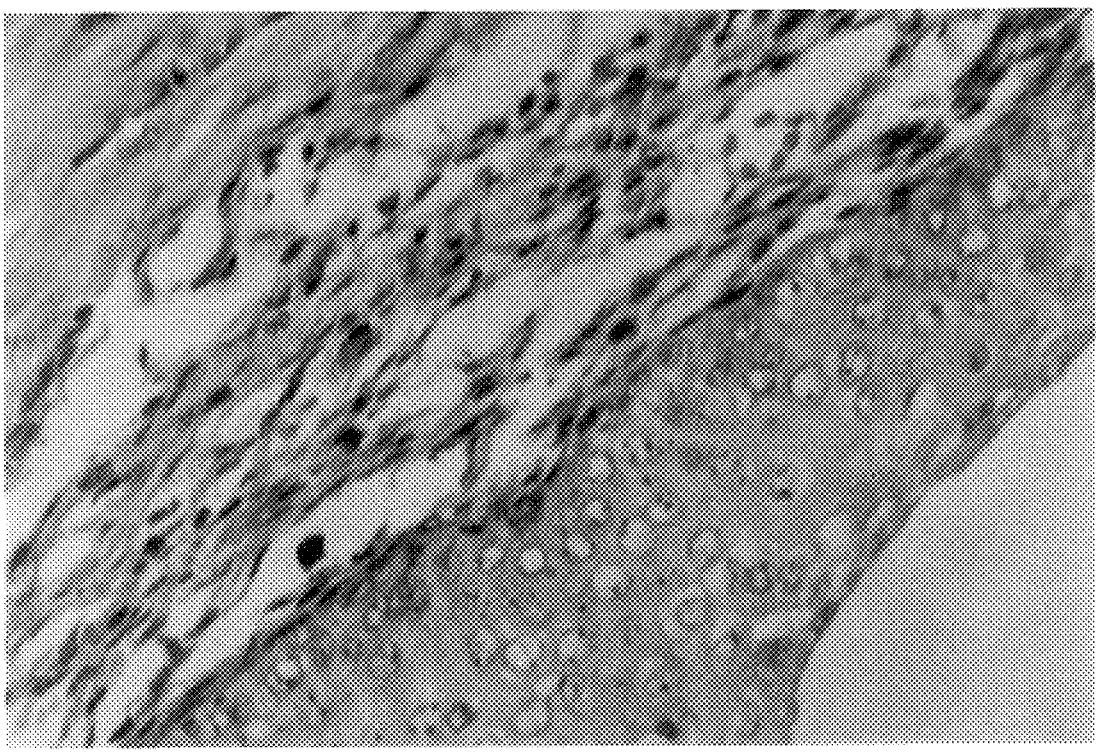

FIGS. 16 and 17 show histology of graft in Haematoxylene and Eosin stain which clearly reveal the microscopic details of wall of regenerated ureter in the graft. FIGS. 16 and 17 show the low and high power microscopic views respectively.

FIG. 17-A shows the magnified view of the transitional epithelium of the regenerated ureter, which is typical of normal ureter.

Figure 18:
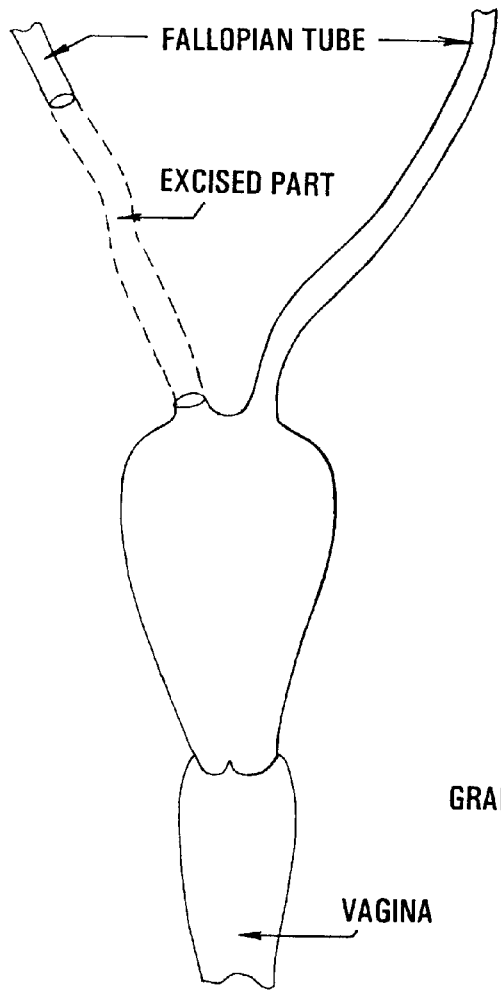
Figure 19:
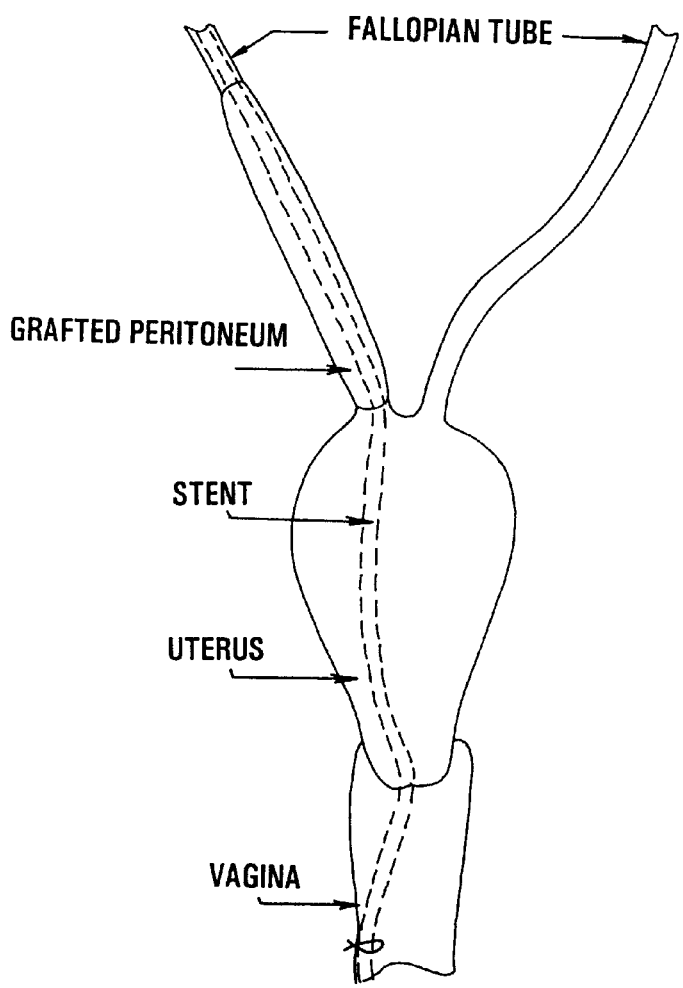

FIGS. 18 and 19 show diagramative representation of regeneration of fallopian tube as per invention.

Figure 20:
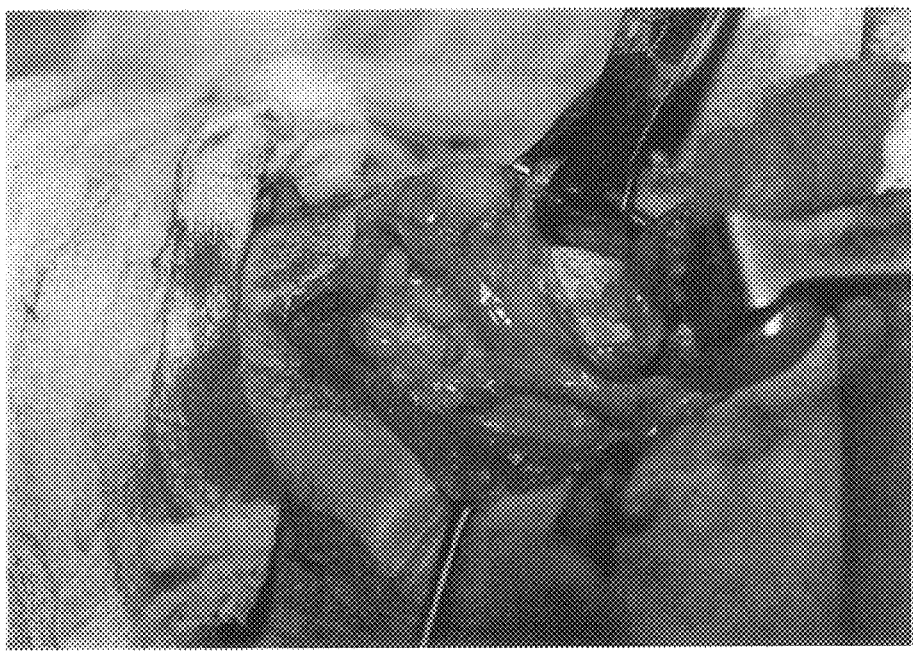

FIG. 20 shows the normal fallopian tube (normal anatomy) in dog.

Figure 21:
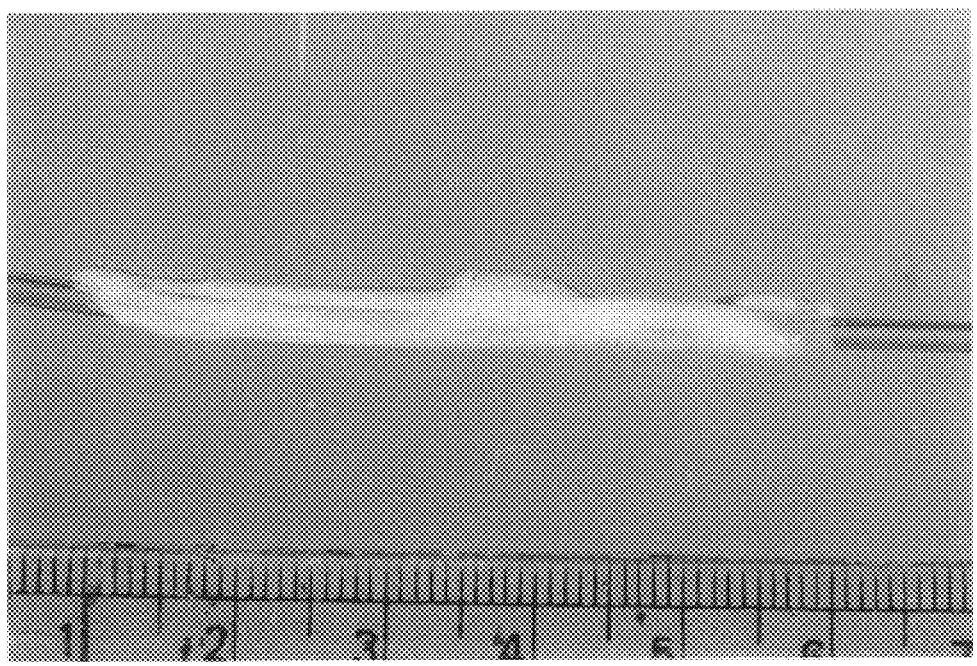

FIG. 21 shows the peritoneal tube having stent inside which is visible through the thin membraneous peritoneal tube.

Figure 22:
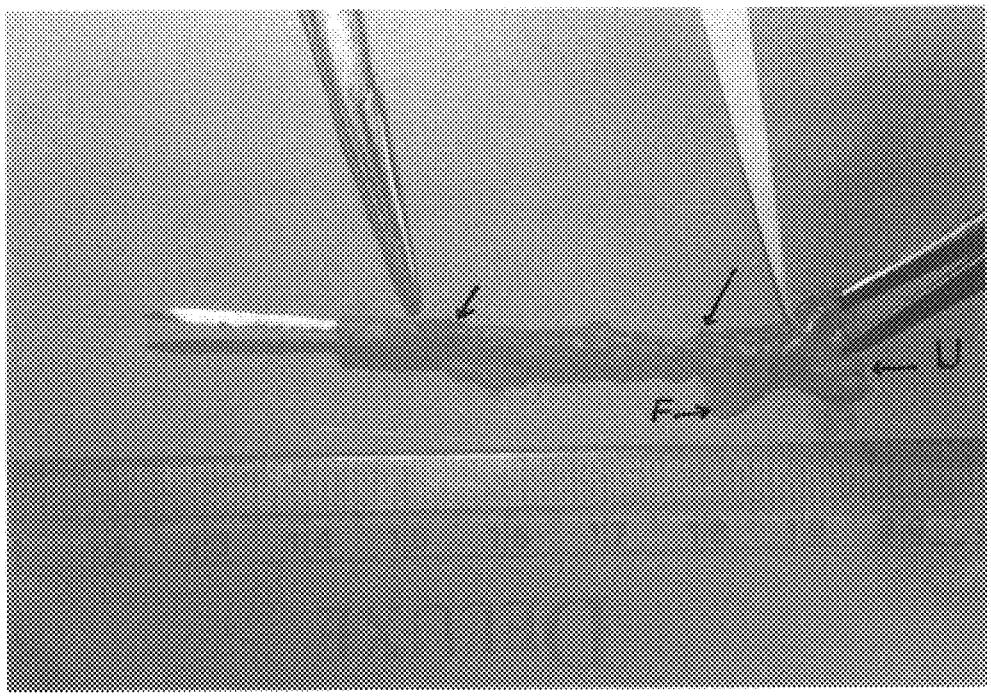

FIG. 22 shows the regenerated fallopian tube in gross.

Figure 23:
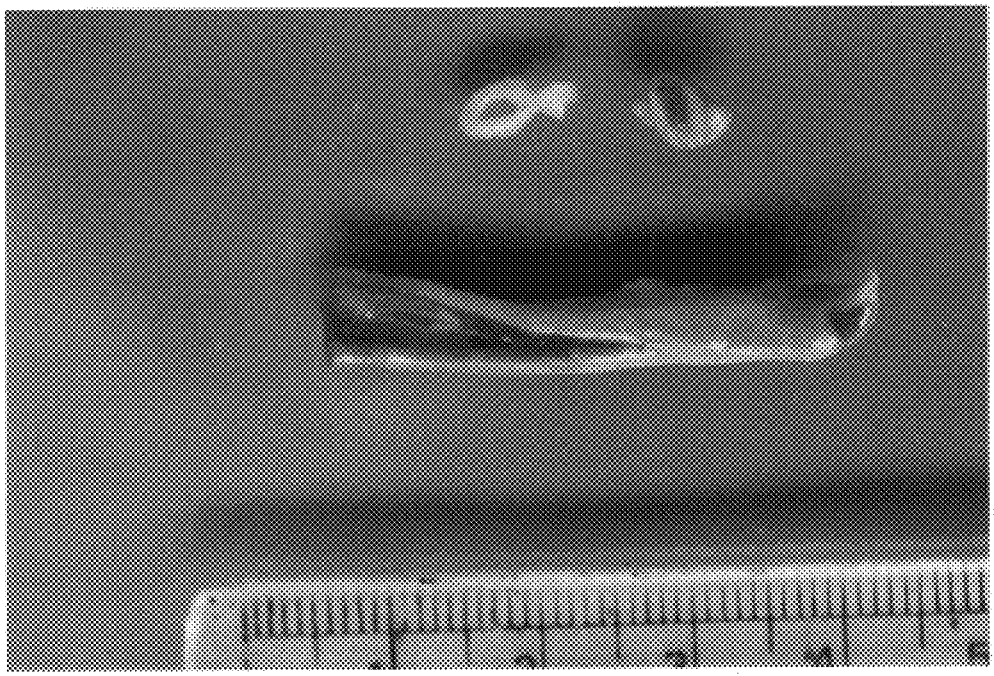

FIG. 23 shows the transverse section of the peritoneal tube prepared before graft (shown in pale white colour), the transverse and longitudinal sections of regenerated fallopian tube are shown in pink colour. In fact, the transverse cut section of peritoneal tube and regenerated tube is kept side by side for comparison.

Figure 24:
Figure 25:
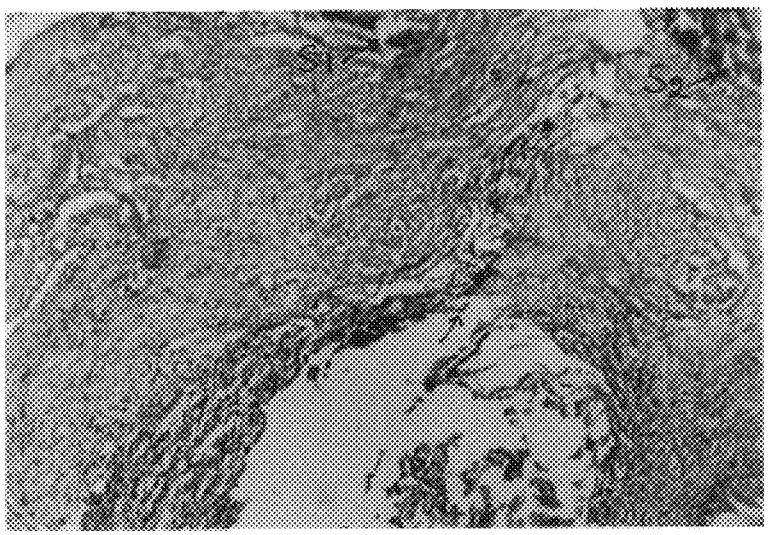

FIGS. 24 and 25 show the histology of grafter fallopian tube clearly showing the different components of the wall of the regenerated fallopian tube.

Figure 26:
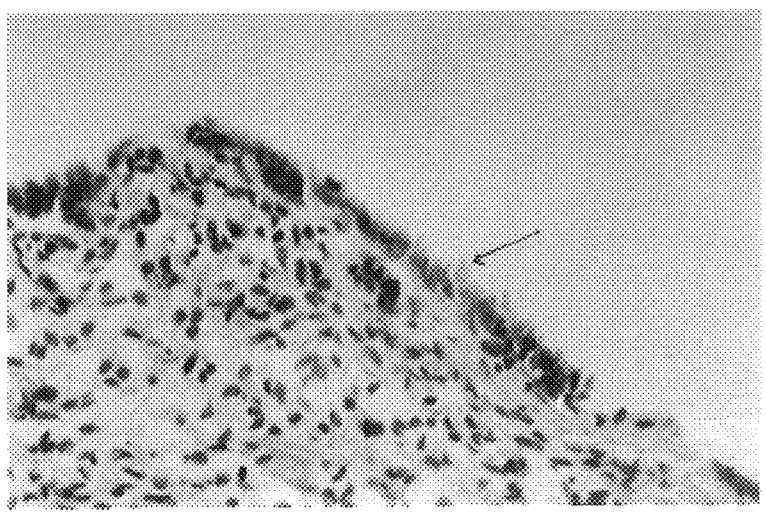

FIG. 26 shows clearly the development of cilia in the mucosal layer of the regenerated fallopian tube.

Figure 27:
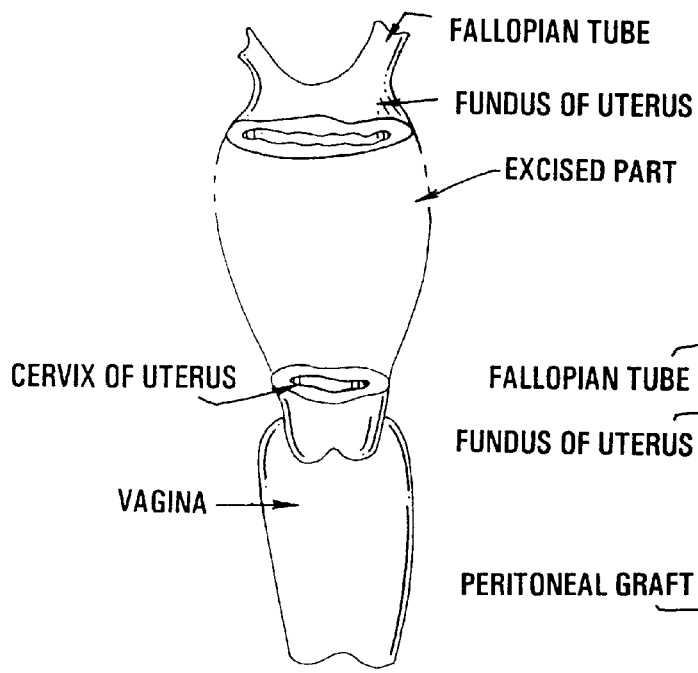
Figure 28:
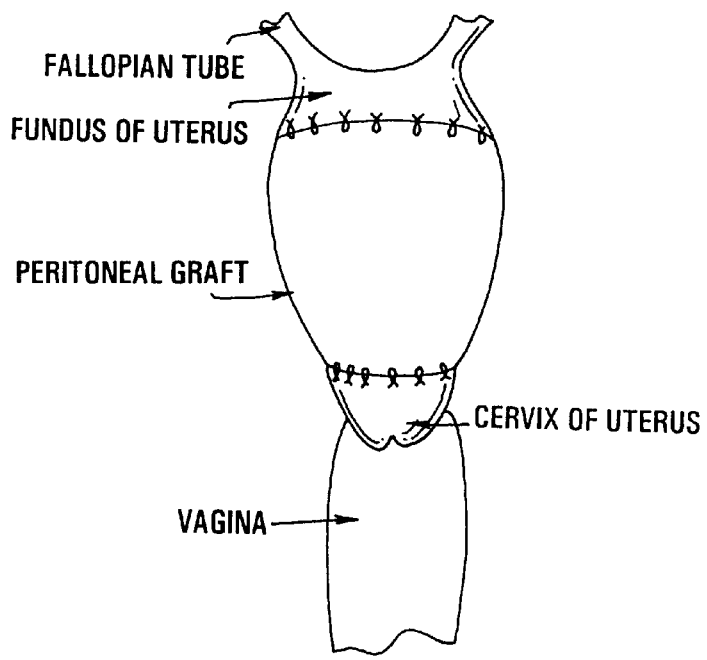

FIGS. 27 and 28 shows diagramatic representation of regeneration of uterus as per invention.

Figure 29:
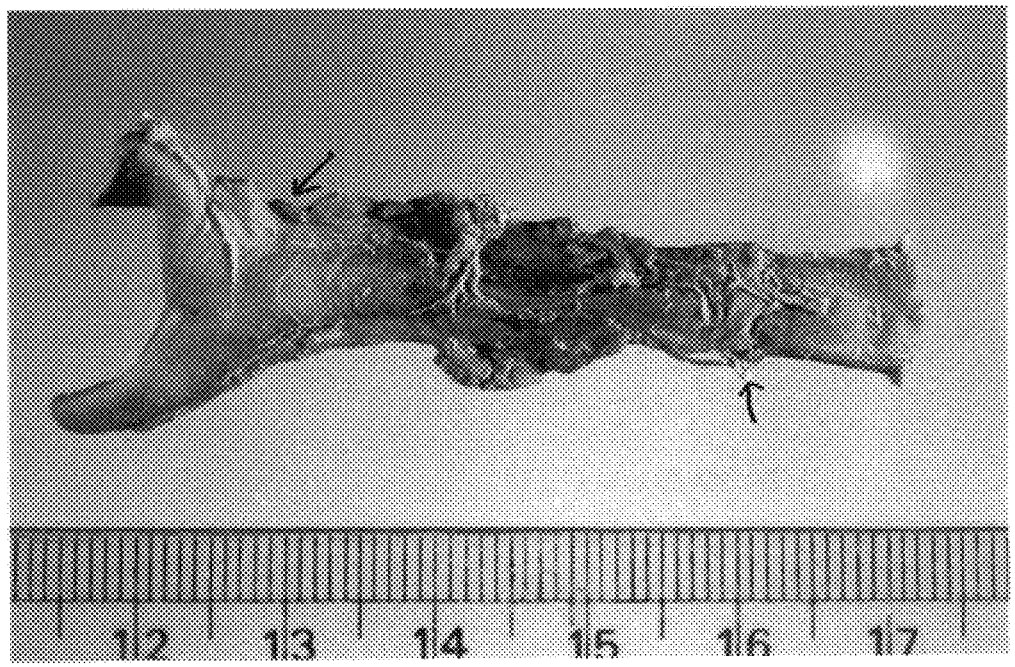

FIG. 29 shows regenerated uterus in gross which has adhesions over the grafted area.

Figure 30:
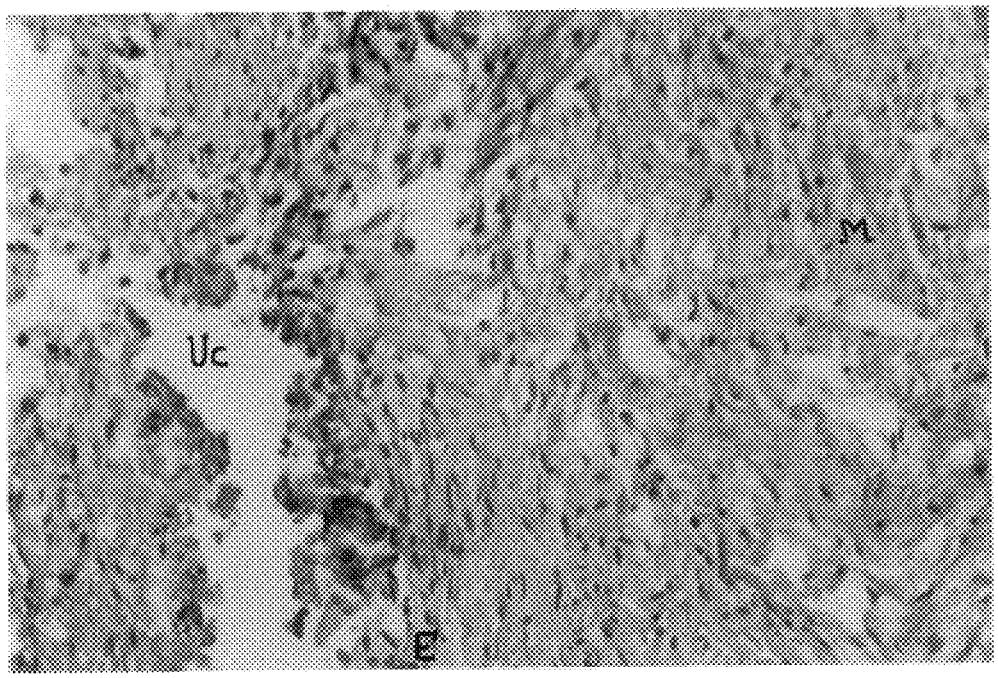

FIG. 30 shows the histological details of regenerated uterus in the graft (H&E stain).

Figure 31:
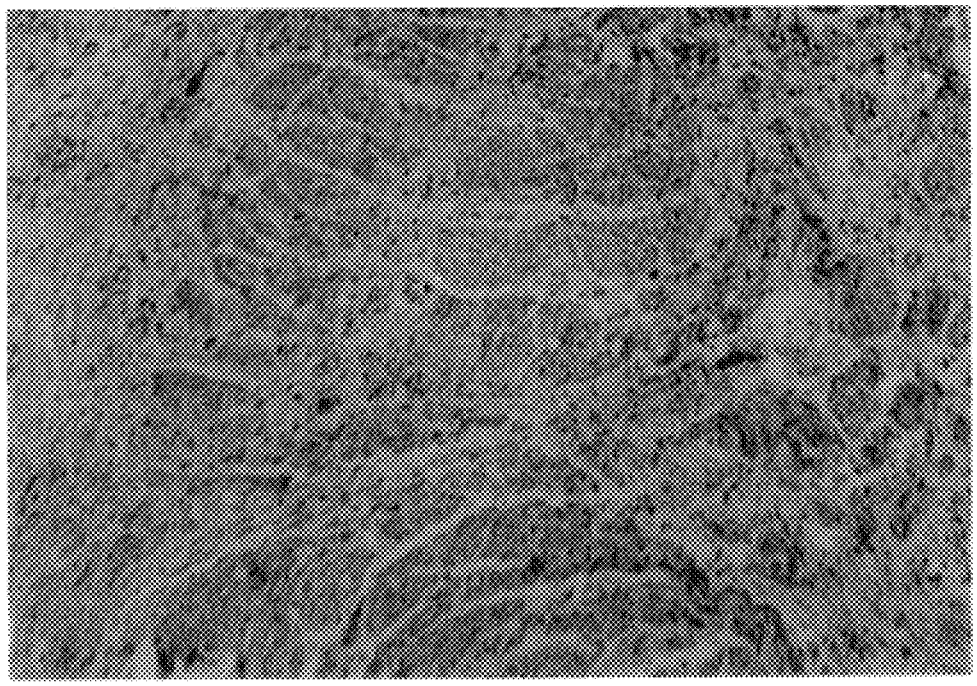

FIG. 31 shows the arrangement of regenerated smooth muscles in the graft-turned uterus. The different shapes of cut bundles of smooth muscles show the intricate arrangements of smooth muscle bundles in the microscopic section.

Figure 32:
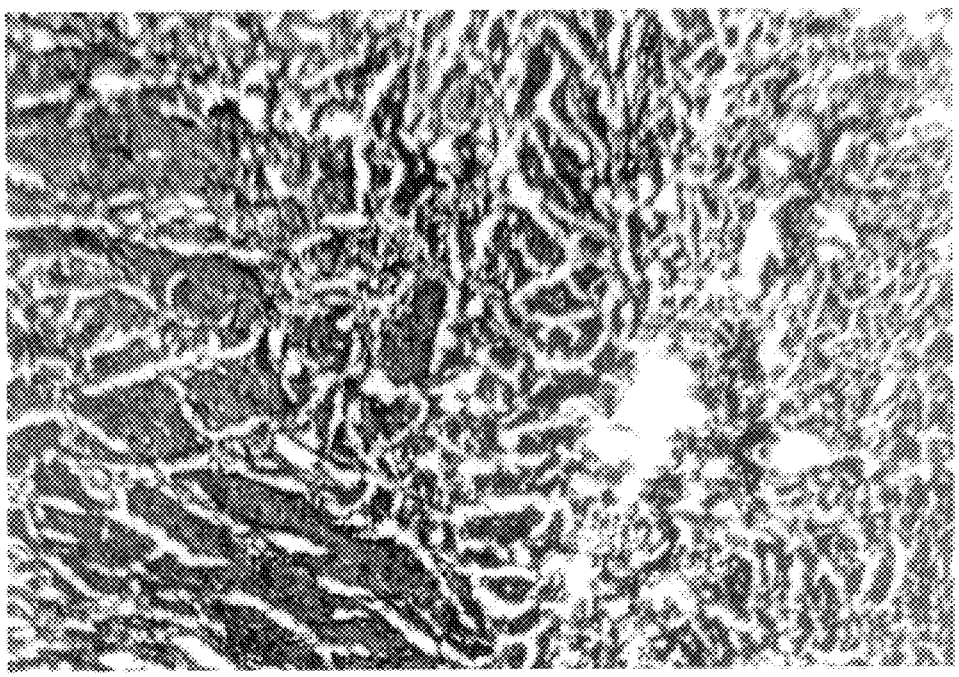

FIG. 32 shows the histology of the graft in Masson's trichrome stain. The smooth muscles are stained pink while fibrous tissue are stained green.

Figure 33:
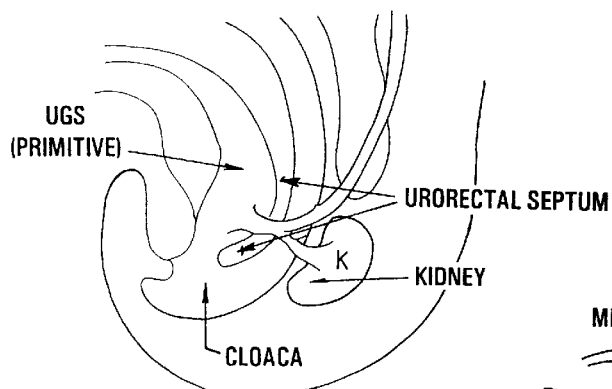
Figure 34:
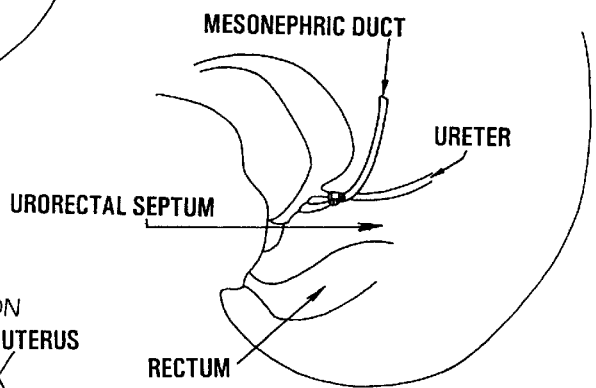

FIGS. 33 and 34 show the development of uro-rectal septum dividing cloaca and the development of urethra in embryo before sex differentiation.

Figure 35:
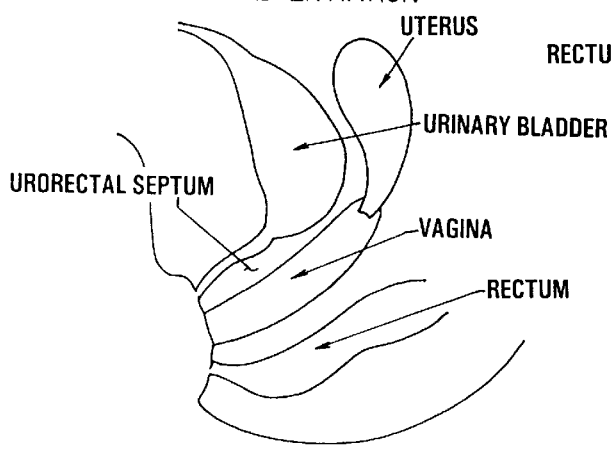

FIG. 35 shows the development of uro-rectal septum separating urinary, genital and rectal tracts after sex differentiation.

Figure 36:
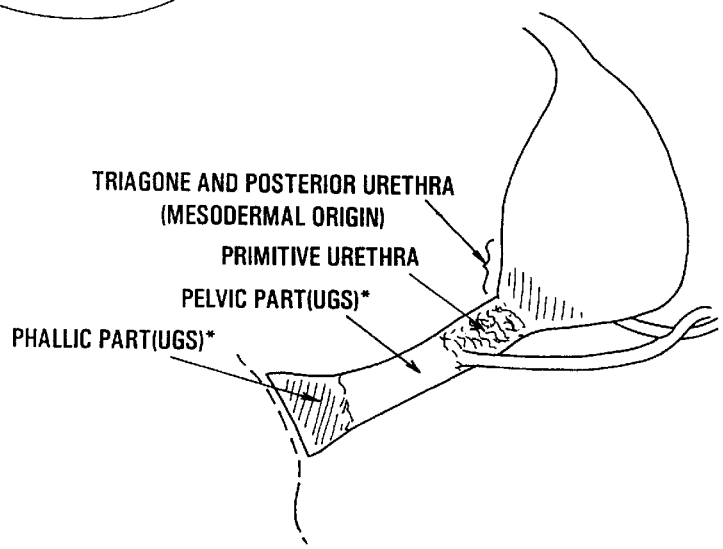

FIG. 36 shows development of urethra from primitive uro-genital sinus and definitive uro-genital sinus having pelvic part and phallic part (after sex differentiation).

Figure 37:
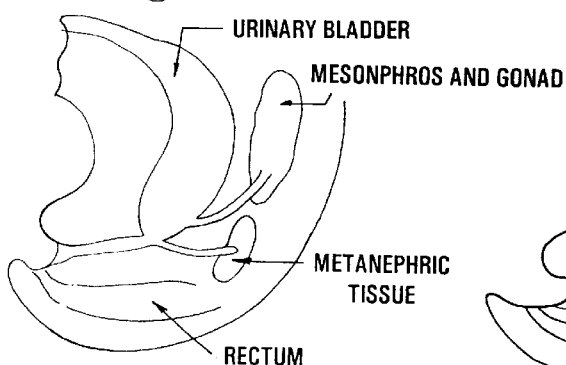
Figure 38:
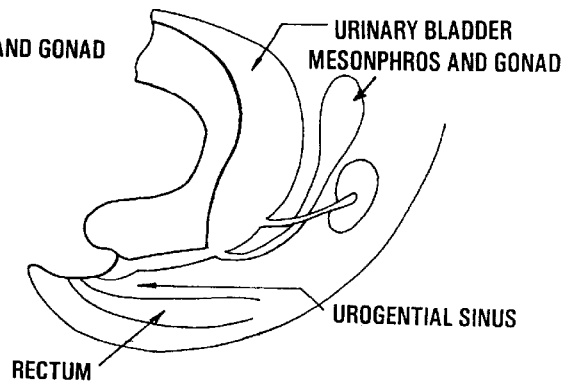
Figure 39:
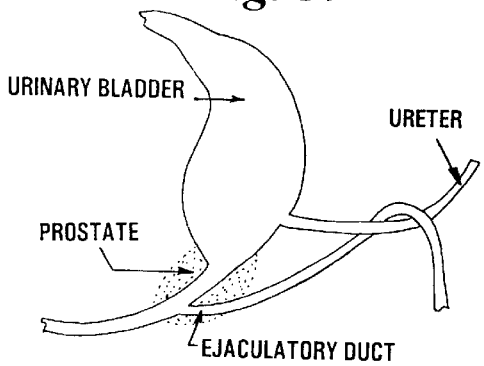
Figure 40:
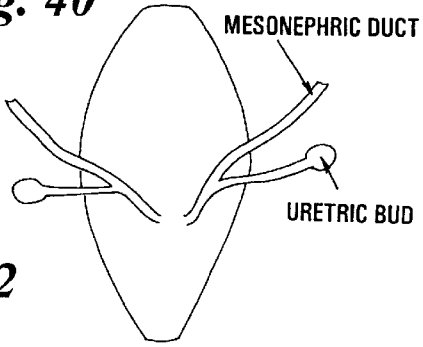
Figures 41, 42:
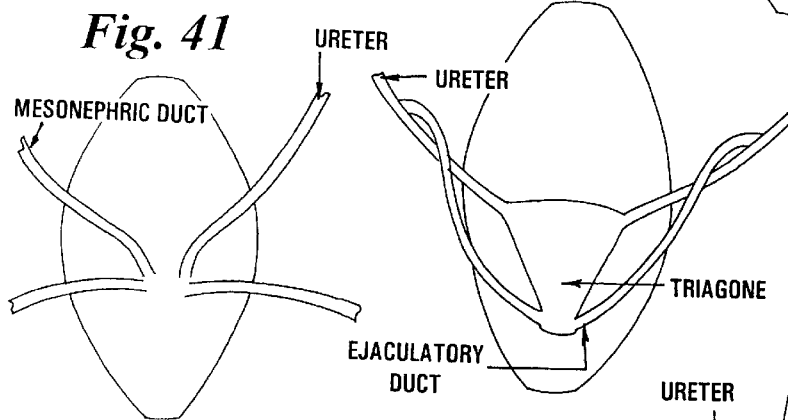
Figure 43:
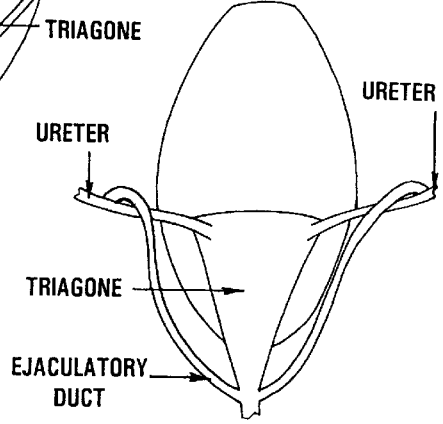

FIGS. 37 to 43 show the relationship of ureter and mesonephric ducts in developing embryo. FIGS. 37 to 39 show a sagittal section of the embryo wherein the development of trigone and posterior urehra are clearly shown. During division of cloaca, the caudal portion of mesonephric ducts are absorbed into the wall of uro-genital sinus and form trigone (FIGS. 40 to 43 of the drawings). The ureters as out growth from mesonephric ducts now enter the bladder separately (FIGS. 40 and 41 of the drawings). The ureteric entrance move cranially and mesonephric duct entrance move closer together and enter posterior urethra to become ejaculatory ducts in males (FIGS. 42 and 43 of the drawings).

Figure 44:
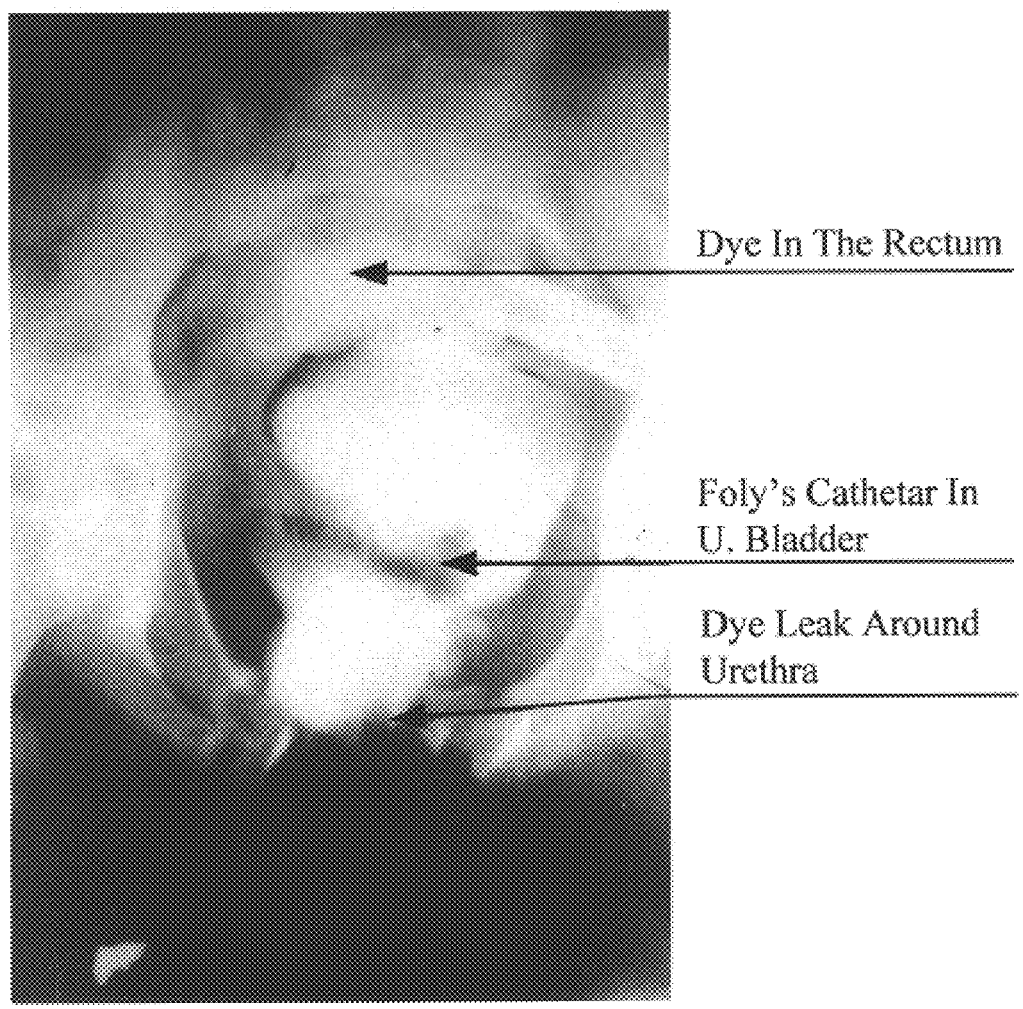

FIG. 44 is an X-ray photograph of pre-operative cystourethrogram of a patient of complex genito-urinary rectal fistula.

Figure 45:
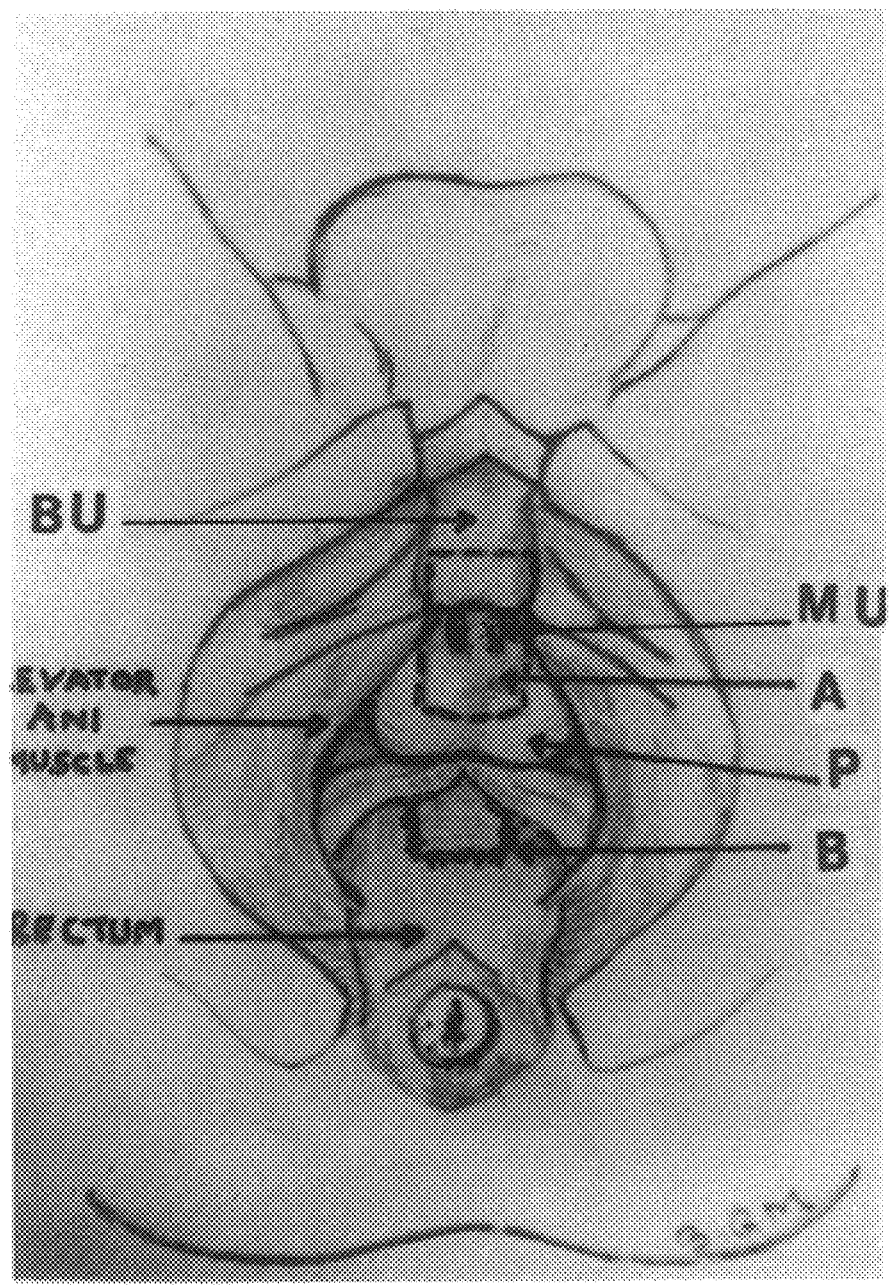

FIG. 45 shows the diagramatic representation of perineal view of exposed urethra and prostrate on one side and rectum on the other side. The dotted lines (A & B) represent use of graft.

Figure 46:
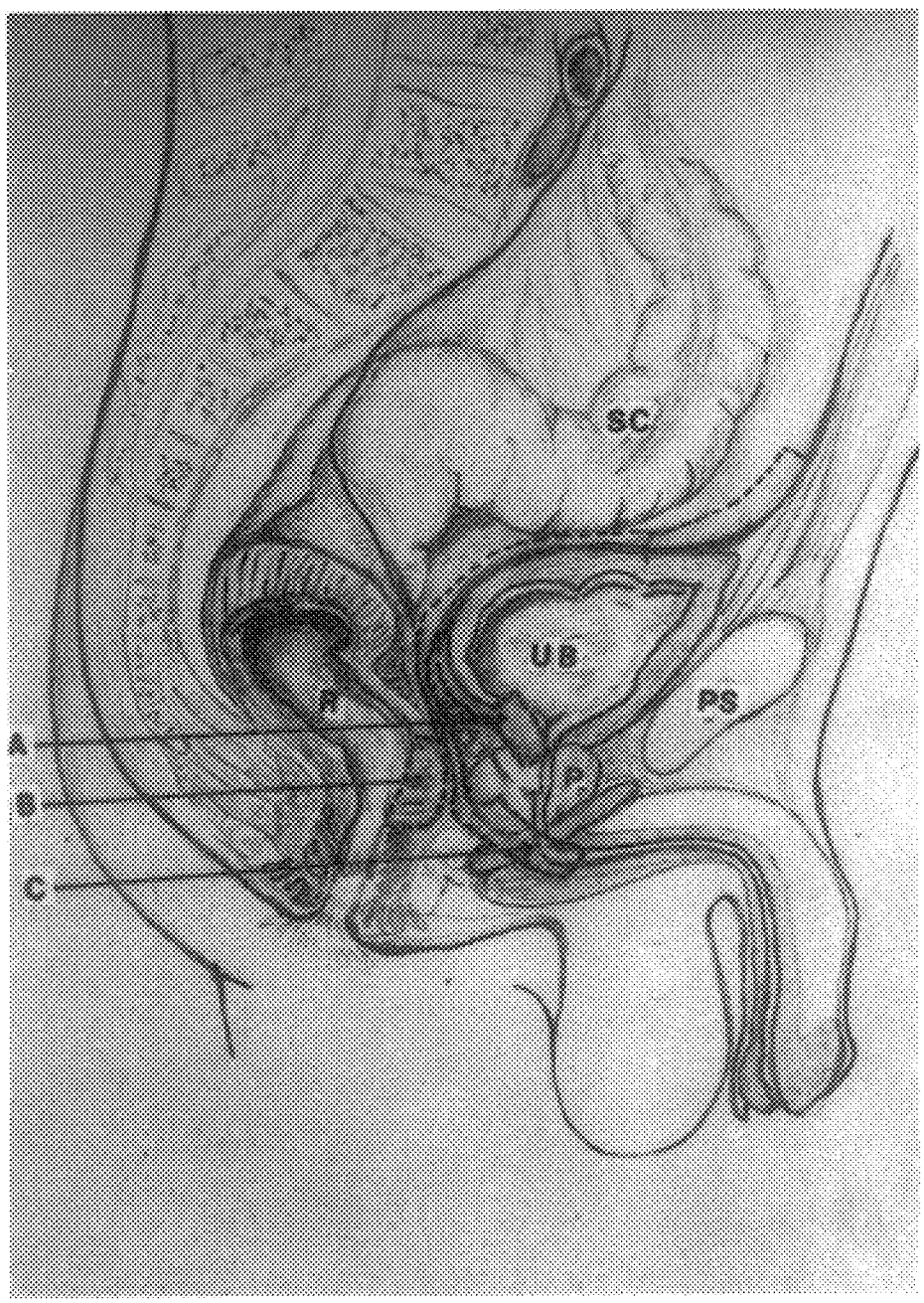

FIG. 46 shows sagittal view of perineum wherein dotted line showing the site of mobilisation of peritoneal graft for use as interpositional tissue between urinary bladder, urethra on one side and rectum virgin on the other side.

Figure 47:

FIG. 47 shows the early post operative cystourethrogram X-ray photograph of repaired genito urinary rectal fistula. Presence of air bubbles (as hollow spaces) in urethra and bladder indicate leak-proof, air tight repair.

Figure 48:
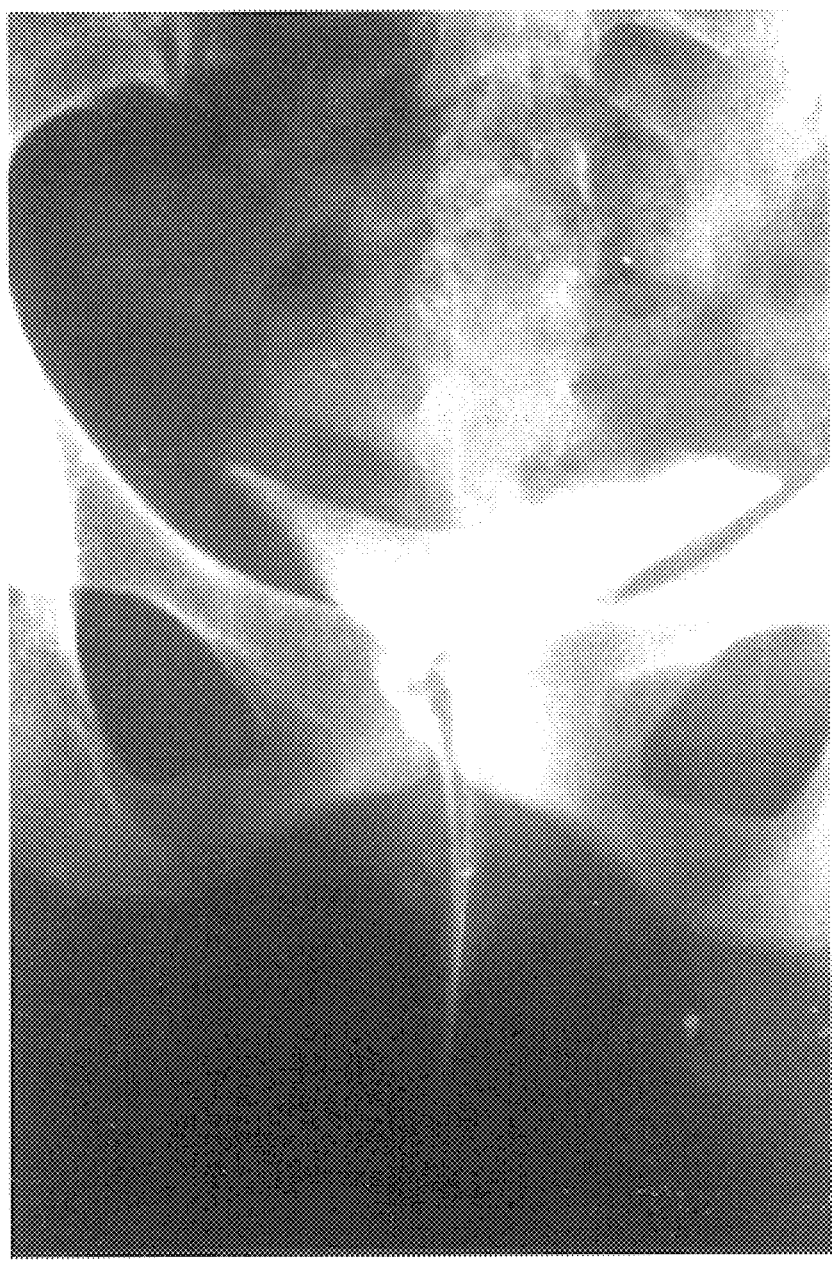

FIG. 48 shows the post operative micturating cystourethrogram X-ray photograph taken after three years subsequent to the repair of genito urinary rectal fistula.

Figure 49:
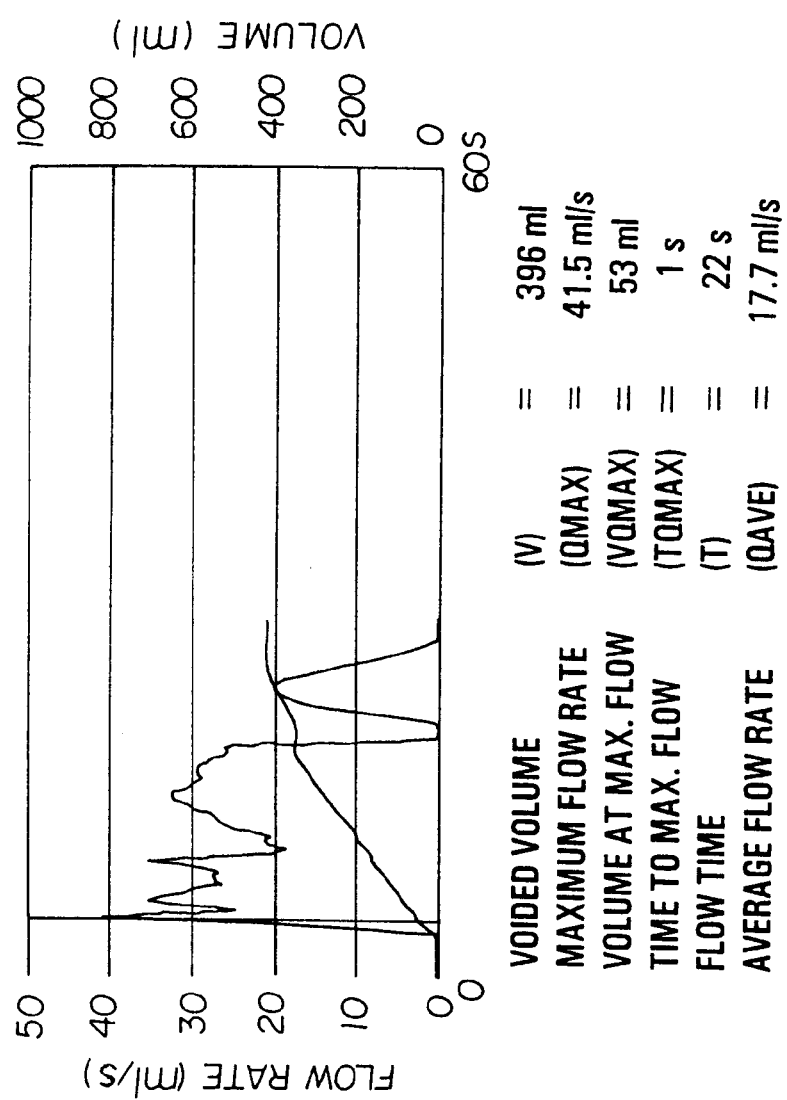

FIG. 49 shows the urine flow chart in a patient of repaired complex genito-urinary rectal fistula (5 year of post operative).

Figure 50:

FIG. 50 shows the immediate post operative photograph of a male patient illustrating abdomino perineal approach. The inverted v-shaped incision is appearing clearly.

Figure 51:
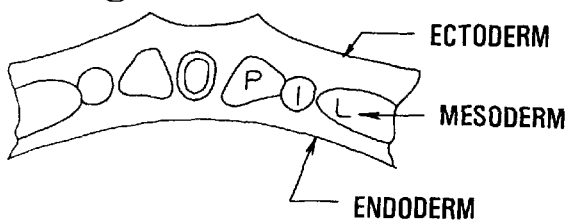

FIG. 51 shows the germ disc with different parts of intra-embryonic mesoderm-parexial mesoderm (P), intermediate cell mass mesoderm (I) and lateral plate mesoderm (L).

Figure 52:
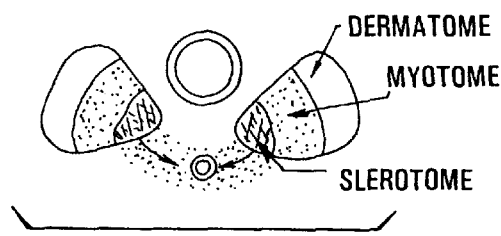

FIG. 52 shows somite subdivisions in embryo. The enlarged view of P in FIG. 51 showing sub-divisions of somite namely Dermatome, Myotome and Sclerotome.

Figure 53:
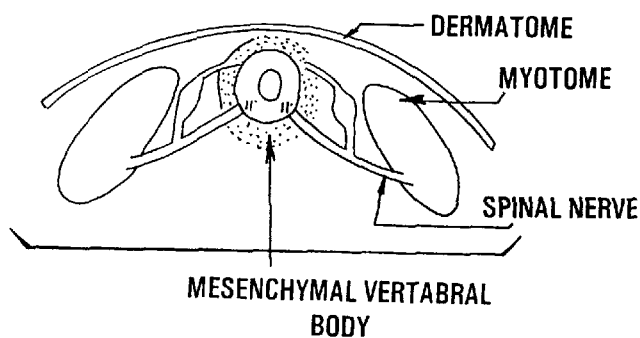
Figure 54:
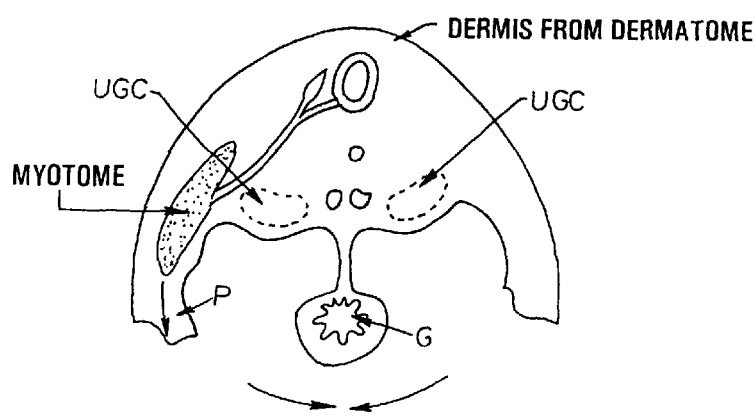

FIGS. 53 and 54 show the further progression in the development of somite from myotome into formation of abdominal wall musculature. FIG. 54 specifically shows the relation of myotome to the coelomic cavity epithelium (peritoneum-P). With folding of germ disc the two sides unite in mid line ventrally (arrow-Marked).

Figure 55:
Figure 56:
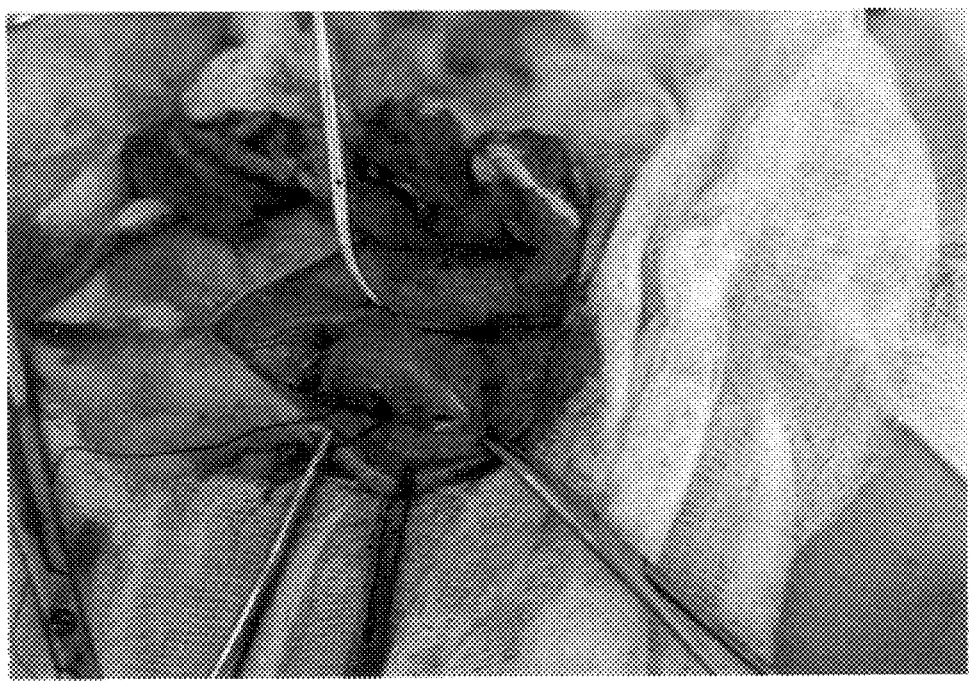

FIGS. 55 and 56 show the placement of peritoneal graft in the excised abdominal wall aponeurotic region. FIG. 56 of the drawings clearly shows the graft layer sutured in place.

Figure 57:
Figure 58:
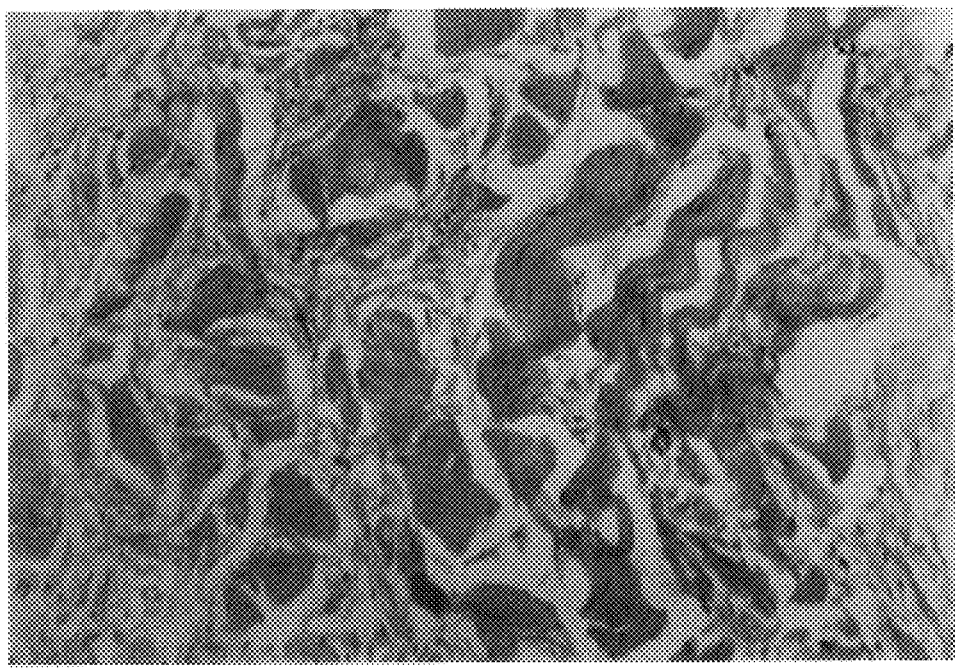

FIGS. 57 and 58 show histology (H & E stain) of the regenerated aponeurosis in the grafted region.

Figure 59:
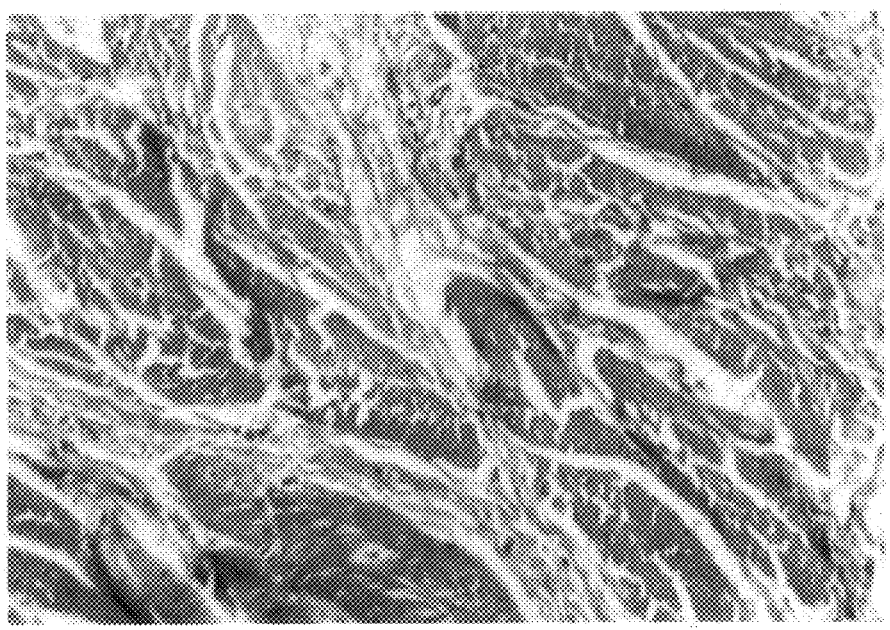

FIG. 59 shows histology of the graft in Masson's trichrome stain showing fibro-aponeurotic tissue in green colour.

Figure 60:
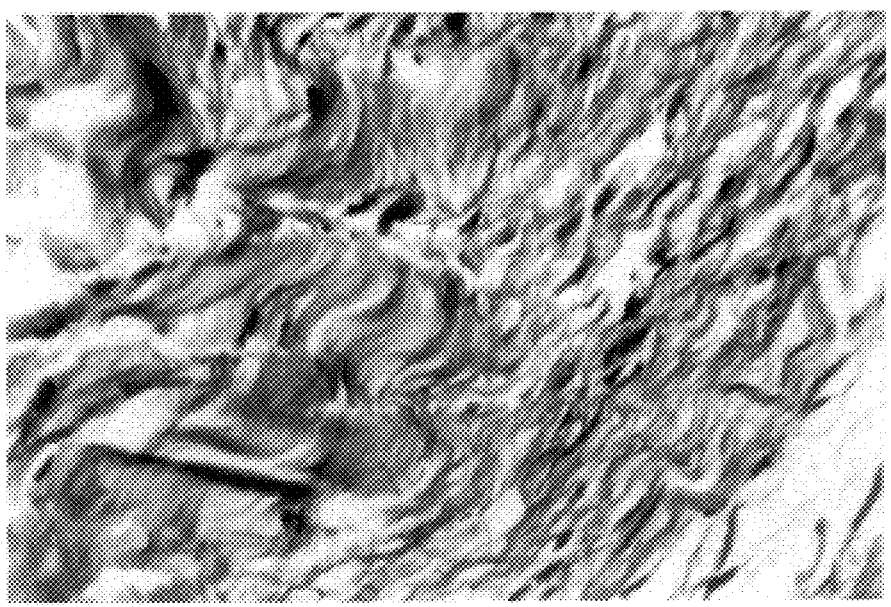

FIG. 60 shows histology of the graft in Masson's trichrome stain, the parallel wavy collagen fibre bundles shown in green indicating the arrangement of fibres in aponeurosis.

Figure 1:
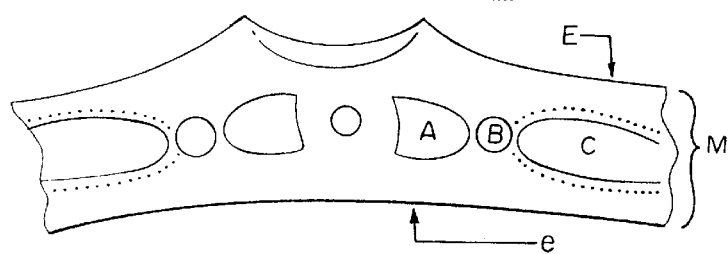
FIG. 1 shows embryonic disc with germ layers highlighting different parts of intra embryonic mesoderm.
Figure 2:
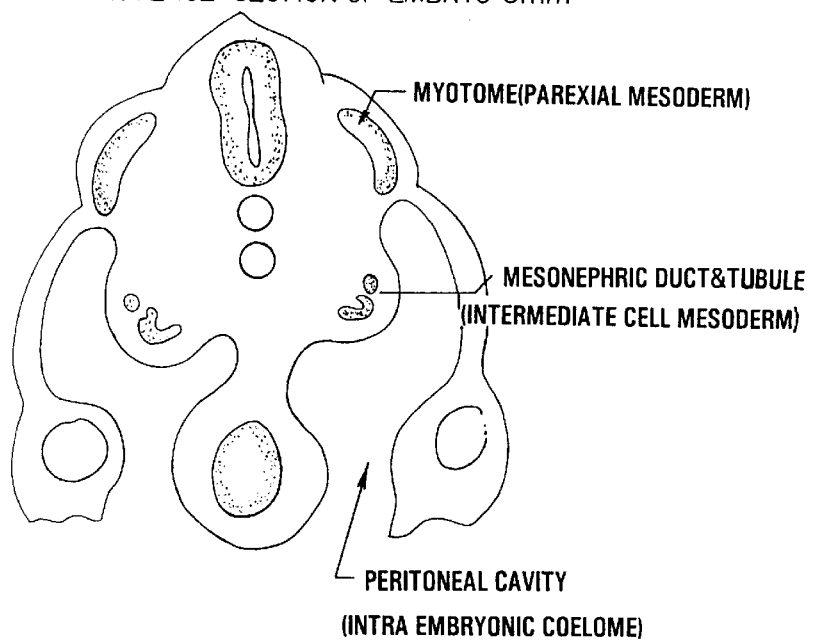
FIG. 2 shows transverse section of embryo on folding of germ disc.
Figure 3:
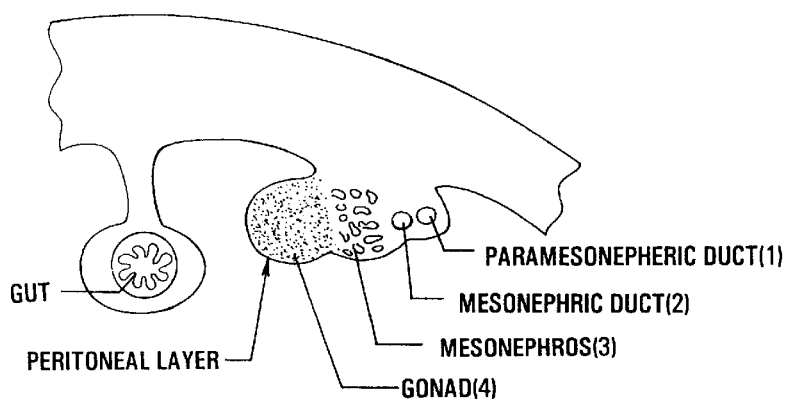
FIG. 3 shows structures of nephrogenic cord.

Therefore, in the present invention, the embryological principles were thoroughly studied, thereafter, the required contiguous areas were earmarked and utilized for the present experiments. FIG. 1 of the drawings relates to embryonal germ layer disk showing three essential germ layers namely ectoderm (E), endoderm (e) and mesoderm (M). In turn, mesoderm has three parts namely Paraxial (A), Intermediate cell mass (B) and lateral plate (C) as shown in FIG. 1. The intermediate cell mass mesoderm forms urogenital system. On the other hand, lateral plate mesoderm forms peritoneum and gastro-intestinal system. At the time of embryonic development, the germ disk folds upon itself. On folding, the germ disk forms into a structure as shown in FIG. 2 of the drawings. FIG. 2 of the drawings is a transverse section of embryo (5 mm size). This FIG. 2 of the drawings clearly shows the formation of intra-embryonic coelom )peritoneal cavity) and myotome from parexial mesoderm, intermediate cell mesoderm into nephrogenic cord (Please refer FIG. 3 of the drawings which shows the structures of nephrogenic cord) and the lateral plate mesoderm into peritoneal layer and gut. FIG. 3 of the drawings is the expanded view of FIG. 2 of the drawings showing the structures of nephrogenic cord comprising paramesonephric duct (1), mesonephric duct (2), mesonephros (3) and gonad (4). FIG. 4 of the drawings clearly illustrates the various stages of formation of paramesonephric duct by invagination of coelomic epithelium into nephrogenic cord mesenchyme.

FIGS. 5 and 6 of the drawings show the formation of paramesonephric ducts on either side of the middle line which eventually meet or unite at the lower end in the centre to form the utero-vaginal canal. In other words, the cells which form fallopian tube and uterus are, in fact, derived from coelomic epithelium by invagination which in embryo forms peritoneum (FIG. 4 of the drawings).

REGENERATION OF ORGANS/TISSUES

The inventor has carried out experiments in regenerating various tissues and organs in live animal models. The experiments were carried out first in dogs and the same were repeated in near human model, namely, Rhesus Monkeys. Also, a few other experiments were carried out successfully in human beings.

REGENERATION OF URETER

The inventor conducted the experiments on dogs and monkeys. In fact, a segment of Ureter was excised as shown in FIG. 7 of the drawings, and the excised portion was replaced by a free peritoneal tube graft obtained from the contiguous embryonal segment over a support as shown in FIG. 8 of the drawings. The donor peritoneum is selected from infra-umbilical region just anterior to caecum and ascending colon extending downward towards pelvis. A proper supporting tube such as a stent was kept in place for a period of three to five months. After removal of stent at the end of the above period, the patency of the tube was observed by X-ray investigation IVP (Intravenous Pyelography) at 6 months and 12 months period postoperatively. FIGS. 14 and 15 of the drawings are X-ray photographs of intravenous pyelography of dog taken at 6 and 12 months respectively. FIGS. 9 and 10 of the drawings show the gross appearance of the regenerated ureter in dog and monkey respectively, the arrows appearing in FIG. 9 of the drawings indicate the regenerated ureter in the grafted area. FIGS. 11 to 13 of the drawings show transverse and longitudinal sections of the regenerated ureter showing the well preserved lumen. In other words, FIGS. 9 and 10 of the drawings which are photographs of regenerated ureter of dog and monkey respectively, clearly show that the free peritoneal grafts from contiguous embryonal segment applied over the stent have developed into a full-fledged ureter. The biopsy specimen obtained at 3 months, 6 months and 12 months period revealed that the full cellular components of the wall of ureter namely epithelium, sub-epithelium, muscular layer and outer scrosal covering are fully developed as shown in microscopic pictures of FIGS. 16 and 17 of the drawings which resemble the normal/original ureter.

Materials and Methods

The following experiments are given as an example only and these should not be construed to limit the scope of the invention.

7 Mongrel dogs (3 males and 4 females) weighing 6–10 kg body weight, were used after quarantine period of 10 days. Under intravenous general anaesthesia with sodium pentobarbitone (40 mg/kg), the right sided ureter was exposed extraperitoneally through lumbar incision. Segments (5–10 cm) of middle ⅓rd of ureter was excised. A stent such as an infant feeding tube (FG-5 size) was introduced in the cut ends of ureter. Blunt blind end of tube was inserted into the proximal segment (FIG. 8 of the drawings) so that urine could come in contact with peritoneal tube by overflow. This arrangement was specially made to create the functional need and required environment for the total regeneration of ureter from the graft. The other end of infant feeding tube was inserted into distal ureter.

However, providing a stent to create a functional need and required environment for regeneration this preferred embodiment and the invention is not restricted to this embodiment only. In fact, the functional need and conducive environment for regeneration can be created by any method. While creating the functional need and a suitable condition, it is not desired to create partial block to urinary flow in the ureter and thereby producing the back pressure changes in the kidney. In other words, block to the urinary flow can be avoided in the ureter.

Peritoneal strip (preferably 5–10 cm long and 2–3 cm wide), taken from infra-umbilical part of abdominal wall just anterior to caecum and ascending colon towards pelvis. This is considered the most representative area of mesoderm from where ureter and peritoneum are developed. The peritoneal tube was constructed round the infant feeding tube by suturing the edges of peritoneum with 4/0 Vicryl eye less suture needle. Care was taken to keep surface of the peritoneal membrane facing peritoneal cavity towards the lumen. Continuity of ureter was established by suturing peritoneal tube to both the spatulated ends of the ureter to avoid narrowing.

Infant feeding tube acting as a stent was removed after 3 months. The specimens for histology were obtained after 3 and 6 months and 1 year postoperatively. Patency of ureter was confirmed by the intravenous pyelography after 6 months and 1 year period. Sections were taken from various sites, e.g. grafted and normal ureter for microscope examination (please refer FIGS. 9, 10 and 16 of the drawings. Antibiotics were used only in perioperative period.

Experiments performed on Mongrel dogs, were observed for 3 months (2 dogs), 6 months (2 dogs) and 1 year (3 dogs). Intravenous pyelography investigation revealed patency of ureter with dilated proximal ureter and mild back pressure changes (please refer FIGS. 14 and 15 of the drawings).

On reexploration of grafted area after 3 months revealed flimsy adhesions around grafted tube. However, no collection of urine, inflammatory exudate or pus was seen in any case. Still, in one dog, concretions were present over the stent but its lumen was patent. There was no compromise to the urinary flow. At 6 months and 1 year period the adhesions were firm but there was no collection of urine, exudate or pus. The peritoneal tube was thickened and indistinguishable from the rest of the normal ureter except the size was broader than the normal ureter. The transverse and longitudinal sections of the grafted tube showed well developed lumen and serosa (please refer FIGS. 11 to 13 of the drawings). In addition, the thickness of the wall having different hues suggests the development of different components of the wall of ureter. These findings were uniform through the length and breadth of the grafted peritoneal tube at 3, 6 and 12 months period. In fact, FIGS. 14 and 15 of the drawings clearly show post operative intravenous pyleography showing dilated ureter. Dye seen up to lower end of ureter (arrow marked) confirms potency of ureter (6 months post operative period). However, FIG. 15 of the drawings specifically relates to intravenous pyelography taken at 1 year post operative period.

The section through peritoneal graft showed all the layers of the wall of the ureter innermost epithelial layer of the graft showed transitional cell epithelium with focal areas of squamous metaplasia. Tunica propira showed infiltration of chronic inflammatory cells. The muscularis mucosa was arranged in circular and longitudinal bundles. The serosal layer was thickened showing inflammatory cells in some sections (please refer FIGS. 16 to 17.A of the drawings).

In the present method, regeneration of ureter was also successfully tried in monkeys. Seven Rhesus monkeys weighing 4.75 to 7 kg body weight aged between 9–12 years, were anaesthetised with Ketamine Hydrochloride (12 mg/kg body weight) by intramuscular injection of gentamycin (8 mg/kg intramuscular) as antibiotic, was given after induction of anaethesia and repeated on first Post Operative day. Kidney and ureter were exposed extraperitoneally by blank incision. Different areas of ureter were excised measuring between 5–15 cms length.

Peritoneum from infraumbilical region lateral to ascending colon was excised (preferably 2.5 cms×5 to 16 cms) and spread over flat surface with serosal surface facing was superficial. The tube of peritoneum was constructed over a stent having multiple perforations. Water tight tube of peritoneum was constructed using 5/0 vicryl suture and tested by injecting saline into the tube. The stent carrying this tube was kept in the place of excised ureter. The promixal end of stent inserted into proximal and distal end of stent into distal ureter. The continuity established by anastomosing tube to proximal and distal spatulated end of ureter. The tube was grafted in the different region of pelvic, pelviureteric junction and upper part of ureter (4 cases) and abdominal part of ureter 15 cms long in 3 cases.

Donor site of peritoneum sutured with 2/0 chronic cat gut to close the peritoneal cavity. The stent was removed after three months post operative period in all the monkeys. Patency of the graft tube was confirmed by intravenous pyelography. Tissue biopsy was taken at 3, 6 and 12 months period and were subjected to histological examination.

Operated Rhesus monkeys were observed for a period of 3 months (3 monkeys) 6 months (3 monkeys) 12 months (1 monkey). In all the monkeys the post operative period was uneventful.

Intravenous pyelography (FIGS. 14 and 15) showed patency of peritoneal tube with little back pressure. On re-exploration, mild adhesions were present around grafted area. There was no shrinkage of tube, collection of urine or inflammatory exudate etc. was observed. The patency of the peritoneum "tube turned ureter" was also confirmed in the biopsy specimen by injecting saline water through one end of regenerated ureter and found that the flow of saline was free without causing ballooning in any place of the tube even when the pressure of the flow of saline was increased.

In two monkeys after 6 and 12 months of post operative period the nephrourterectomy was performed. The adhesions on grafted site were firm, but separable with sharp dissection. The grafted tube was reasonably thick and tubular. Differentiation from the rest of the ureter was difficult.

Gross examination:

On transverse section, the grafted tube showed perfect lumen (please refer FIGS. 11 and 13 of the drawings). The wall had different hues indicating different layers of the wall of ureter. Longitudinal section showed full thickness of wall and smooth mucosal surface (please refer FIGS. 12 and 13 of the drawings).

Microscopic examination:

The scanned view (FIG. 16 of the drawings clearly reveal all the components of the wall of the regenerated ureter. In addition, FIG. 17-A clearly reveals the transitional epithelium in the grafted peritoneum at most of the places. Further, a few patches of squamous epithelium were also seen at a few places in some specimen. Epithelium and subepithelium layer showed infiltration of chronic inflammatory cells (FIG. 17 of the drawings). Muscularis wall was seen in two distinct layers of outer circular and inner longitudinal muscle bundles which are very clearly appearing in FIG. 17 of the drawings. Further, the blood vessels are also clearly visible. Serosal layers was distinct and showed chronic inflammatory cell infiltration.

The inventor has successfully regenerated ureter at different sites such as upper ureter, middle ureter etc., and different lengths of segments excised in different animals. FIG. 9 of the drawings shows the regeneration of mid-ureter in dog whereas FIG. 10 of the drawings shows the regeneration of upper part (near kidney) of the ureter in monkey.

Peritoneum is derived from embryonal mesodermal germ layer and preserves stem cell in its structure in adults. Embryologically, the urogential tract and peritoneum are contiguous position to each other (FIG. 2 of the drawings). Both are mesodermal derivatives. If stem cells of peritoneum are exposed to embryologically contiguous tissues of the urogential system, then these stem cells may undergo desired metaplastic transformation and regenerate desired tissues in the region where exposed i.e. it may regenerate tissues of urogential system. If tissue organizers and inducers of embryo are properly used at the same time coupled with functional need, the perfect organogenesis is possible. In other words, the urogential system develops from intermediate cell mass of mesoderm and the peritoneum develops from lateral plate of the mesoderm, the peritoneum having pluripotent cells may undergo change if exposed to urological tissues. Results of the present study show the formation of ureter in the region of grafted peritoneum. Surroundings and environment of urological tissue have stimulated the stem cells of peritoneum during proliferation and differentiation process to form ureter to carry out the function. The tissue organizers in the embryo regulate the development of the tissue. (Singh Inderbir. An Introduction to human embryology 5th ed. 1991. p. 380). Probably, similar factors in adults have also induced and organized the formation of perfect ureter.

The present experiment was performed to study the possibility of metaplastic transformation and tissue regeneration capacity of the primitive stem cells of adult tissues and hence, contiguous embryonal segment was selected as donor site for particular organ to be developed based on the principles already explained.

In the past, the researchers have used peritoneum with rectus sheath or skeletal muscle (transverse abdominis) to repair duodenum defects in pigs. In this case, the smooth muscles failed to regenerate. The lyophilized dura and free peritoneum from adjacent peritoneal envelope for grafting renal pelvis and pelvi ureteric junction was used but no ureter wall could be developed. This may be due to the fact that the proper embryonal segment was not used and in addition, the presence of associated rectus sheath and transverus abdominis muscle prevented the action of tissue inducers and organizers to induce organogenesis.

Metaplastic change of epithelium to transitional or squamous type may be due to the tube stent kept for 3 months duration. But the inventor observed the animals even after removal of stent up to 6 to 12 months post operatively and found such changes persistent even after stent removal.

In the present experiments, perfect regeneration of wall of ureter was achieved probably due the use of free peritoneum and that too without rectus sheath or muscle. The donor peritoneum was from proper (developmentally) embryonal segment contiguous to the ureter. In addition, according to the inventor, tissue inducers and organizers of embryo in the regions play part in perfect organ development.

REGENERATION OF FALLOPIAN TUBE

The role of totipotent nature of stem cells of embryo in organogensis and development of various tissues of the body in embryo is well known. However, the inventor for the first time realized that if stem cells of autogenous peritoneum from embryonal contiguous region exposed to tissue system of urogential tract in vivo, then these pluripotent cells may differentiate and proliferate into desired tissues in the region based on the principles of embryonal organogensis.

After successfully regenerating ureter in vivo from stem cells present in peritoneum in dogs and monkeys, the present study was undertaken to regenerate fallopian tube in live animal models. In fact, the inventor has successfully regenerated fallopian tube in dogs. FIG. 18 of the drawings clearly shows the excised portion of fallopian tube. The excised portion was replaced by peritoneal tube graft made from the peritoneum taken from pelvic and posterior wall peritoneum and anastomosed in the region over a stent which was passed through uterus into vagina and secured in the vagina with a stitch (FIG. 19 of the drawings). FIGS. 22 and 23 of the drawings show the successfully regenerated part of the fallopian tube with a probe in the lumen (FIG. 22 of the drawings), part of uterus (U) and contralateral fallopian tube (F) is also seen in the picture of the drawings. In other words, after replacing excised fallopian tube with autogenous peritoneal tube in mongrel dogs the regeneration was observed up to 12 months. The histological studies revealed complete regeneration of all the components of the wall of fallopian tube (please refer FIGS. 24 to 26 of the drawings).

Materials and methods

The following examples are given to understand the invention more clearly and easily, but never to restrict the scope of the invention.

The inventor attempted the present invention on seven mongrel female dogs of 7 to 10.5 kg. body weight. The fallopian tube segment measuring 5 to 7 cms was excised and replaced by a free peritoneal tube. The donor peritoneum measuring 2 to 8 cms. In size excised from retro vesicular pelvic and posterior wall and the abdomen, and was used to construct the tube. The tube was constructed by suturing the edges of excised peritoneum with 5/0 Vicryl eyeless suture on a suitable polythene tube stent. The cut end of the stent introduced into the fimbrial part of the fallopian tube while the other end introduced into the uterine cut end of the fallopian tube. This end of the stent preferably was brought down into the vagina through uterus and secured into the vagina with a suture (FIG. 19 of the drawings) to avoid accidental slip. The stent was removed after 3 months of post operative period in all the dogs. The biopsy specimens were obtained after reexploration at 3, 6 and 12 months period. Microsections were prepared for study with Haematoxylin and Eosino and Masson's trichrome stains.

On reexploration after 3 months post operatively in three dogs, the operation site of peritoneal graft revealed flimsy adhesions which were easily separable. The thin peritoneal membrane tube showed thickening on gross appearance. The lumen remained intact. The adhesions were found to be firm at 6 and 12 months in 3 and 1 dog respectively. The lumen of the grafted peritoneal tube remained intact and patent with free opening into the uterine and fimbrial end of the fallopian tube (please refer FIGS. 22 and 23 of the drawings). In FIG. 22 of the drawings, the regenerated fallopian tube (marked with arrows) is seen with a probe in the lumen, "F" indicates the cut end of contralateral fallopian tube and "U" indicates part of ureter attached with the regenerated tube.

Microscopic examination:

Haematoxylin & Esoin stain revealed development of all the components of wall of the fallopian tube in the grafted peritoneum (FIGS. 24 to 26 of the drawings). The mucosal epithelium was columnar in nature. The sub mucosal layer showed presence of glandular structure. The infiltration of chronic inflammatory cells seen in the mucosal and serosal layers. The muscles were arranged in two different layers circular and longitudinal layers. In one case, the peritoneum could not be approximated edge to edge at the time of construction of peritoneum, the development of the wall components were seen beyond the actual line of approximation (FIG. 25 of the drawings). In addition, the blood vessels are clearly visible.

Masson's Trichrome stain development of smooth muscles in pink & fibrous tissue in green.

Histological picture of the biopsy specimen obtained after three months period is (shown in FIGS. 24 to 26 of the drawings). It clearly shows different components namely epithelial layer, muscular layer and serosal of the wall of the fallopian tube. FIG. 25 of the drawings also reveals the development of full components in the part of peritoneum beyond the line of approximation (arrow in the centre) held by two sutures (S1 and S2—shown by Arrow marks). the chronic inflammatory cell infiltration seen in the mucosal and serosal layers was the result of local inflammation and the presence of infection resistant macrophages inherent in the peritoneal membrane.

The scientific rationale:

Fallopian tube and peritoneum both developed from the embryonal mesodermal germ layer in the embryo. Fallopian tube develops from intermediate cell mass mesoderm and peritoneum from lateral plate mesoderm (FIG. 1-B and FIG. 1-C of the drawings). After folding of germ disk, both intermediate cell mass and lateral plate mesoderm both lie in contiguous regions (FIG. 2 of the drawings). The urogential ridge with its component structures is covered with mesothelium of coelomic cavity (FIGS. 2 and 3 of the drawings). The fallopian tube develops from paramesonephric duct which is developed by the invagination of the covering mesothelium of embryonic coelom (FIG. 4 of the drawings). Therefore, the cells which form fallopian tube also form peritoneum. But the regional and functional needs are different and are responsible for specific differentiation and proliferation of these cells into different tissues. The tissue organizers, inducers and inhibitors, mould these tissues into perfect organs and tissues.

The present surgical technique provides cell movement of pluripotent cells present in the peritoneum membrane to the region where tissue or organ is to be developed. The intristic factors of cells are present in the stem cells and have the capacity to under go metaplastic transformation as explained in peritoneum section. Local tissue organizers present in the region once induce the differentiation of cells, these cells then proliferate into similar desired cells in the region. Thus, the desired tissue regeneration and organogensis is achieved. The tissue factors are present in the region and also the surrounding tissue organizers inhibit and govern the tissues development to proper size and shape of the organs and tissues.

The microsurgical reconstruction of fallopian tube studied by Gauwerky and others showed regeneration of mucosa (Hum. Reprod. 1994—9(11)—2090–2102 and Zentral bl Gynakol. 1994—116(3)—173–178). The ciliogenesis between 2nd and 3rd week after salpingostomy of rabbit has been observed by Vasquez et al (Eur. J. obst. Gynaecol. Reprod. Biol. 1984—18—103–118). The use of PTFE (Teflon) and biodegradable microporous synthetic tube as uterine horn graft has been attempted for healing and regeneration of endometrium of uterus and fallopian tube in rats. However, there is no regeneration occurred and in addition there is no mention of cilia or mucosal regeneration in the study. These produce obstruction at the junction of uterus and fallopian tube. The use of splints may contribute to the use of biodegradable microporous artificial fallopian tube in tubal surgery (Jonkman, M. F. et al. Artificial organs 1986—10(6)—475–480). In the present investigation no cilia could be observed in some of the dogs probably because the specimen fixed in formalin and microsections performed after 8 to 10 days time which increases the tissue friability and shedding up of the cilia in the process. In fact, the ciliogenesis and cilia bearing cell population depends upon (i) Site—the cilia are abundant in fimbrial end and ampula of the fallopian tube. The cilia are scanty in isthumus and interstitital part of the fallopian tubes. (ii) Phase of oestrous cycles—the cilia bearing cells increase in population during proliferative phase and decrease in secretory phase of oestrous cycle i.e. the ciliated cell population is different in different phases of oestrous cycle. In the present study, the part of fallopian tube regenerated is at the isthumus area of fallopian tube where cilia are scanty. However, the cilia were observed when injectable oestrogen was administered prior to biopsy (FIG. 26 of the drawings—the arrow shows the distinct cilia bearing cells).

In summary, the autogenous peritoneal stem cells have the capacity to form fallopian tube in vivo when proper segment of peritoneum is exposed to the tissue system of the fallopian tube. The above evidence established that the inventor for the first time has regenerated the fallopian tube.

REGENERATION OF UTERUS

Organogenesis and tissue regeneration based on embryonal principles by desired meteplasia of stem cells of autogenous tissue is a new venture and the inventor successfully employed the above principles to regenerate uterus. In fact, the above described regenerations of ureter and fallopian tube by surgical technique in dogs and monkeys have encouraged the inventor to take up the study of regeneration of uterus.

Central portion of uterus was excised leaving fundus uteri, fallopian tubes attached above and cervix uteri below (FIG. 27 of the drawings). The excised part of uterus was anastomosed with free peritoneal tubular graft of the size of the excised uterus (FIG. 28 of the drawings). The free peritoneum donor site was selected from the pelvic and posterior wall peritoneum. No stent was kept in this place as the lumen was big sized and obliteration of lumen was not feared. However, if desired, a suitable support or a stent can be kept inside the uterus. FIG. 29 of the drawings shows the regenerated uterus in the region of the grafted peritoneum. The biopsy specimen studied at the end of 3 months. FIG. 30 of the drawings shows histological picture of the regenerated uterus where all the components of the wall of the uterus appear well developed, for example, epithelium, muscular layer and serosal layer. The intricate arrangement of smooth muscle layer of the uterus is typical and it is clearly shown in FIG. 31 of the drawings by different shapes and sizes of cut sections of smooth muscle bundles in the microscopic section. The development of muscle layer of the uterus was specially and remarkably highlighted by using Masson's trichrome stain which stains smooth muscles pink and fibrous stain in green (Please refer FIG. 32 of the drawings).

Material and Methods

The following description is given merely to illustrate the present invention and this description should not be used to restrict the scope of the invention.

The standard guidelines for the care and use of animals approved by animal ethical committee of the local institution were followed. Seven Mongrel female dogs of 2 to 5 years of age weighing 6 to 10 Kg were operated after 10 to 15 days of quaratine period. Under general anesthesia with Sodium pento brabitone (40 mg/kg. Body weight), perioperative antibiotic cover, with aseptic and antiseptic precautions the body of uterus was excised after separating uterine arteries on both sides. The excised part of uterus was replaced with suitable size of peritoneal tube and anastomosed with proximal and distal stump of the uterus (FIGS. 27 and 28 of the drawings). The donor peritoneum was selected from pelvic peritoneum posterior to uterus extending on to the peritoneum of the posterior abdominal wall. The operated dogs were observed for three months (3 dogs) and six months (4 dogs). At the end of observation period, the grafted peritoneum was excised along with healthy uterus at both the ends of the grafts. The histological changes were noted in serial sections of the graft. The sections were stained with Haematoxylene-Eosin and Masson's trichrome stains.

Results

The post operative period in all the seven dogs was uneventful except in one dog, In this dog, on first post operative day there was slight bleeding through vagina. All the dogs accepted the feed on first post operative day. At three months on reexploration, the region of the graft showed mild adhesions around it. There was no collection of haematoma, inflammatory extrudate or pus. The adhesions were easily separable. At six months, the adhesions were more marked and strong. The grafted peritoneum was having uniform thickness and consistency as compared to normal uterine stumps. The gross appearance at 3 and 6 months was similar (FIG. 29 of the drawings). Histology of serial sections of the graft revealed uniform changes throughout the graft. The mucous membrane was low columnar. The mucous and submucous layer showed inflammatory cell infiltration. The smooth muscles were arranged in distinct layers (please refer FIGS. 30, 31 and 32 of the drawings). The development of smooth muscles in pink color and connective tissue in green stain is separately shown by Masson's trichrome stain in (FIG. 32 of the drawings).

Discussion

After the fertilization of ovum the egg is formed which gradually grows and forms germ layer disc of ecto, endo and mesoderm (FIG. 1 of the drawings). These layers either along or in combination form all body tissues. The mesoderm forms majority of body tissues independently (Harrison R. G. introduction to embryology. Cunningham's T. B. of Anatomy 12th ed. reprint.1991p. 42–49). The peritoneum and uterus both are derivative of lateral plate and intermediate cell mass mesoderm respectively (FIG. 1 of the drawings). The uterus is developed by the union of two paramesonephric ducts in the mid line (FIGS. 5 and 6 of the drawings). The paramesonephric ducts are developed from the cells of epithelial lining of intraembryonic coelem, as these cells invaginate into the nephrogenic cord mesenchyme (FIG. 4 of the drawings) to form the paramesonephbric ducts. The intraembryonic coelemic epithelum later becomes peritoneum. In other words, the peritoneum cells in fact forms the uterus. The peritoneum cells are pluripotent primitive stem cells and remain so even in adult life. These stem cells as explained earlier have the capacity to undergo metaplasia to form mesodermal tissues. Since the uterus is derived from the mesoderm germ layer and the stem cells of peritoneum membrane are also derived from mesoderm, the peritoneal cells are used in the present invention.

The formation of all the components of the wall of the uterus in the present experiment is due to the fact that both peritoneum and uterus are of mesodermal origin. The surgical technique provides cell movement to proper location. The selection of peritoneum from contiguous embryonal segment is important. Since the metaplasia of cells is needed functionally and morphologically in the desired location of uterine region, the term "desired metaplasia" seemed to be more appropriate. The inventor feels that the conversion of stem cells of autogenous peritoneum to uterine tissue is due to the intrinsic capacity of stem cells to differentiate and proliferate, new environmental and functional need to which the cells are exposed and the interaction with neighboring cells.

NEW SURGICAL TECHNIQUE IN THE MANAGEMENT OF COMPLEX GENITO-URINARY RECTAL FISTULAE IN HUMAN BEINGS:

Repair of genitourinary and rectal fistula is a difficult problem. The incidence is 1% of all pelvic operations. The combined fistulae, urinary and rectal are 3–4% in large series of obstetric & gynaeological injuries (Turner-Warwick. R. The use of pedicle graft in repair of urinary tract fistula. Brit J. Urol. 1972. 44: 644) Urinary fistulae are seen in 2% following hystrectomy (Macasset M. A.: Lu. T: Nelson J. H. Ureterovaginal fistula as a complication of radical pelvic surgery Am. J. Obst. & Gynae. 1976, 124: 757) recurrence of fistula is from 4% to 30% following repair (Lazarus H. M. Urinary fistula in women with special reference to their operative technique. J.Obdst.Gynae.India (1958: 10: 1., T. E. Dreschcer C. Martey J. O. Fort D. Vesicovaginal fistula. revisited. Obst. Gynae. 1988: 72: 307, Rao. K. B. Postgraduate Obst. Gynae 3rd ed. by M. R. Krishna Menon, P. K. Devi, K. Bhaskar. Orient Longman, 1986. Even though, the success of repair after first attempt is 86% and 94% is subsequent attempts in simple genito urinary fistula (Elkins T. E. Ghosh T. S. Tagore G. A., Stokes, R. Transvaginal mobilistion and utilisation of the anterior bladder wall to repair vesicovaginal fistulae involving urethra: Obst. Gynaecol. 1992: 79: 455.) the management of complex fistulae involving bladder and urethra is difficult. The complications after repair of large fistula are seen upto 40–60%. Attempts at repair of simple fistula after 19–23 previous attempts are on record (Kiricuta. I. Goldstein. A. M. B. The repair of extensive vesico vaginal fistula with pedicled omentum a review of 27 cases., J. Urol. 1972, 108: 724). The need to improve the existing surginal procedures has been realized especially when there is partial or total urethral loss. Peritoneum consists of stem cells of mesodermal origin and is capable of undergoing metaplasia (Rosai Juan. Ackerman's "Surgical Pthology" C. V. Mosby Co., 1989. Vol.II. Ch. 26 p. 1638). Autogenous peritoneum can thus be used in repairing complex genitourinary rectal fistula. Regeneration of urethral mucosa is observed in animal studies using synthetic absorbable material in urethral reconstruction. (Olsen L. Bowald S. Busch C. Canlstein J., Ericson I., Urethral reconstruction with a new synthetic absorbable device. An experimental study Scand J. Urol. Nephrol. 1992, 26: 323).

The first attempt should be the best attempt for repair of complex urinary fistulae as with each unsuccessful repair there is more tissue damage and increased scarring. These fistulae are difficult to repair as their location is deep in pelvis. Even after successful repair of the fistula the complications which may persist are incontinance of urine, urethral stricture, vaginal stenosis, small bladder syndrome, dysparunia etc. (Elkins T. E. Ghosh, T. S. Tagore G. A. Stokes. R. Transvaginal mobilisation and utilisation of the anterior bladder wall to repair vestivaginal fistulae involving urethra: Obst. Gynaecol. 1992; 79: 455) The description of surgical technique to approach this type of fistula in literature is meagre and results are not encouraging. The success of repair is low.(Leela Prasad M. York Masson procedure for recto urethral fistula in benign tumour. Mastery of surgery, 1993, Vol.II. 2nd ed. Ch.135) the dissection is through scarred areas which is due to trauma of injury/operation, urinary and fecal irritation of tissues, making the approach difficult. Considering the causes of failure namely imperfect closure of fistula, haematoma formation, ischaemia of tissues etc. a combined abdomino-perineal/vaginal approach should be used. Surgical repair varies from case to case. Temporary faecal diversion is important in gut injury cases. For interpositional tissue the locality available pelvic peritoneum, vaginal mucosal flap to form urethra over indwelling catheter has been advocated but because of scarring and repeated attempts this is difficult. The technique of pedicled graft of skeletal muscle is available but undergoes disuse and fibrotic atrophy and is ill adopted to resist infection which is common with such fistula. (Venable D. D. Modification of anterior perineal trans rectal approach for complicated prostatico urethrorectal fistula repair J. Urol. , 1989=142=381.) Use of vascularised scrotal dartos flap interposition has been used for low variety of urinary fistula but for associated bladder and high rectal injury this procedure may not be suitable (see table 1). Rectal fistula developed after prostatectomy repaired by modified York Masson procedure in single stage is an excellent cost effective procedure for low cariety of fistula. Its suitability for recurrent variety needs evaluation. Pedicled omental graft is suitable as it has abundant blood supply, lymphatic drainage, has adequate length and can be positioned properly for which mobilisation of ascending colon and appendicetomy is advisable. (Turner-War-wick R. "Urinary fistulae in female" Campbell's Urol. 1986. Vol.3. Ch. 74. p.2718) females, child bearing potential could be compromised by occlusion of the fallopian tube. If transeveras colostomy is done for rectal "injury," this may produce difficulty in omental mobilisation. Late complication of omental buldge into vagina may need excision of excess omentum after incising anterior vaginal wall. (Hamel H. K. Sharma S. K. Goswami A. K. Urethrorectal fistula complicated by posterior urethral structure an appraisal of management by transpublic approach. Urol. International, 1991, 15: 768) Various procedures have been tried to create new urethra using microvascular free radial forearm flap, buccal mucosa a combined free autologus bladder mucosal/skin graft, vascularized tube flap of tunica vaginalis, lyophilized human dura, synthetic absorbable device (Table II).

The present study is based on the embryological principles of mesodermal development of the urethra and local regional tissues. Reconstruction of posterior urethra (prostatomembranous) is complicated no only by the relatively restricted surgical access but fundamentally its whole length is sphincter active.(Turner Warwick R. Urethral stricture surgery. Urologic Surgery 4th edition, J.B. Lippincott Co. Philadelphia N.Y. London 1991 ch. 65 p. 713–749). The material as substitute for urethroplasty should be region friendly and protective to the functional sphincter mechanism in the region. Because of the reasons already explained in scientific rationale of the use of peritoneum, this membrane is used in this study for interpositional purpose and urethroplasty.

In the conventional surgical management of complex genito-urinary rectal fistulae, which required either excision or plastic repair/replacement, lots of post-operative complications as well as high failure rates of treatment have been observed. The repair of complex genito-urinary rectal fistulae is a most complicated one and the success rate of which is marginal. This human ailment is still quite common in developing countries. The management of complex fistula which involves both the bladder and urethra is also difficult. The complications after repair of large defects are seen upto 40–60% (Elkins T. E. et al Obst. Gynaecol. 1992=74=455). Urinary incontinance, stricture urethra, vaginal stenosis, amenorrhoea, small bladder syndrome, dysparunia are some of the complications after closure of fistula (Elkins, T. E. et al: Transvaginal mobilisation and utilisation of the anterior bladder wall to repair vesicovaginal fistulae involving urethra: Obst. Gynaecol. 1992=79=455). Repair of simple fistula after 19–23 prior attempts are on record (Kiricuta, I., Goldstein, A. M. B. The repair of extensive vesicovaginal fistula with pedicled omentum a review of 27 cases., J. Urol., 1972=108=724). Genito vesico-urethral fistula are difficult due to deep situation in the pelvis where access is difficult and repair interferes with control mechanisms of bladder neck. A need to improve the existing surgical procedures has been long realized especially when there is loss of partial or total urethral substance ((Elkins, T. E. et al: Transvaginal mobilisation and utilisation of the anterior bladder wall to repair vesicovaginal fistulae involving urethra: Obst. Gynaecol. 1992=79=455).

A repair of complex genito urinary rectal fistula is dependent upon a correct diagnosis, adequate exposure and meticulous dissection. In addition, there is a need of some form of viable interpositional tissue which has long been realized. Table 1 provides a list of interpositional tissues used in the prior art.

TABLE 1

(Interpositional tissues used in the prior art)

| Sl. No. | Author's Name | Diagnosis | Operative procedure | Number of cases | Tissue used |
|---|---|---|---|---|---|
| 1 | Fazio V. W. et al. SGO 1987 = 164 = 148 | rectourethral fistula | rectal flap | 3 | rectal flap |
| 2 | Jones I. T. et.al. Dis colon Rectum 1987 = 55 = 615 | Urethrorectal fistula | Transanal rectal flap | 4 | rectal flap |
| 3 | Venable D. D. J. Urol 1989 = 42 = 381 | Prostatic urethrorectal fistula | Anterior perineal transanorectal Park's technique modified | 1 | pedicled dartos island flap and anterior rectal wall flap |
| 4 | Wood T. W. and Middleton R. G, Urol. 1990 = 35 = 27 | Rectourinary fistula | Single stage transrectal trans-sphincteric | 7 | rectal wall |
| 5 | Hamel H. K. et.al. Urol Internat. 1991 = 15 = 768 | Urethrorectal fistula with stricture | Transpublic approach urethroplasty | 7 accident cases | omentum |
| 6 | Elkins, T. E. et al Obstet Gynacol 1992 = 79 = 455 | Vesi-courethro vaginal fistula | Transvaginal | 1 re-current 19 primary | anterior bladder wall |

In cases where there are urethral injury with urethral substance loss, a suitable substitute to construct urethra/ urethroplasty is essential to avoid post-operative complications. In the past, many attempts were made to reconstruct urethra employing various materials. A list of such materials is given below in table 2. Table 2 illustrates various materials used to reconstruct urethra e.g. as Scrotal flap to even Synthetic absorbable material but, unfortunately, employing such materials were accompanied with various complications. Therefore, attempts to use so many different materials to identify a suitable material for urethral reconstruction itself is an evidence to show that none of the materials used in the prior art were satisfactory.

TABLE II

VARIOUS MATERIALS USED IN URETHRAL RECONSTRUCTION

| Author & Title | Year | Material used |
|---|---|---|
| Blandy, J. P. et al Urethroplasty by scrotal flaps for long urethral stricture Br. J. Urol. 68 = 40 = 261 | 1968 | Scrotal flap |
| Gilbaugh, J. H. et al Partial replacement of the canine urethra with silicon prosthesis. Invest. Urol. 1969 = 7 = 41 | 1969 | Silicon prosthesis Partial replacement of urethra |
| Hendren, W. H. et al. Tubed free skin graft for construction of male urethra J. Urol. = 1980 = 123 = 858 | 1980 | Tubed free skin graft |

TABLE II-continued

VARIOUS MATERIALS USED
IN URETHRAL RECONSTRUCTION

| Author & Title | Year | Material used |
|---|---|---|
| Harrison D. Reconstruction of urethra for hypospadic cripples by microvascular free flap transfers. Brit. J. Plastic Surg. 1986 = 39 = 408 | 1986 | Microvascular free radial fore arm flap |
| Duffy P. et al Combined free autologous bladder mucosa/skin tube for urethral reconstruction: An Update. Brit. J. Urol. 1988 = 61 = 505 | 1988 | Combined free autologus bladder mucosa/skin tube graft |
| Khoury A. et al Urethral replacement with tunica vaginalis: A pilot study. J. Urol. 1989 = 142:628 | 1989 | Vascularized tube flap of tunica vaginalis |
| Villavicencio H. Reconstructive plastic surgery of urethral stenosis: Urethroplasty with lyophilised dura mater. Arch. exp. Urology 1989 = 42 = 309 | 1989 | Lyophilized dura mater. |
| Hubner W. A. et al Autologus everted vein graft for repairing long section urethral defects Urol. Res. 1991 = 19 = 131–134 | 1991 | Autologus everted vein graft |
| Osler L. et al Urethral reconstruction with new synthetic absorbable device. An experimental study, Scand. J. Urol. Nephrol., 1992 = 199 = 26–32 | 1992 | New synthetic absorbable device PGA-PHB prosthesis (Astra Meditech Co. Molndal Sweden) |
| Morey A. F. & MC Aninch J. Urol. 1996 = 155 = 1696 | 1996 | Buccal mucosa |

Therefore, as stated earlier, these fistulae are difficult to repair as their location is deep in pelvis and even after successful repair of the fistula, the complications may persist. In other words, the success of repair is low. In addition, the description of surgical technique to approach this type of fistula in litertue is meagre and results are not encouraging. (Leela Prasad M., York Masson procedure for recto urethal fistula in benign tumour. Mastery of surgery 1993 vol.II 2nd edition). The dissection is through scarred areas which is due to trauma of injury/operation, urinary and fecal irritation of tissues, making the approach difficult. Therefore, the first attempt should be the best attempt for repair of complex urinary fistulae as with each successful repair there is a tissue damage and increased scarring.

Considering the causes of failure namely imperfect closure of fistula, haematoma formation, ischaemia of tissues etc. a combined abdomino-perineal/vaginal approach should be used. Surgical repair varies from case to case. Temporary fecal diversion is important in gut injury cases. For interpositional tissue, the locally available pelvic peritoneum vaginal muscosal flap to form urethra over indwelling catheter has been advocated but because of scarring and repeated attempts, this is difficult. The technique of pedicled graft of skeletal muscle is available but undergoes disuse atrophy and is ill adopted to resist infection which is common with such fistula. Use of vascularized scrotal dartos flap interposition has been used for low variety of urinary fistula but for associated bladder and high rectal injury this procedure may not be suitable. Rectal fistula developed after prostatectomy repaired by modified York Masson procedure in single stage is an excellent cost effective procedure for low variety of fistula. However, its suitability for recurrent variety needs evaluation. Pedicled omental graft is suitable as it has abundant blood supply lymphatic drainage has adequate length and can be positioned properly for which mobilisation of ascending colon and appendicectomy is advisable. In females, child bearing potential could be compromised by occlusion of the fallopian tube. If transverse colostomy is done for rectal injury this may produce difficulty in omental mobilisation. Late complications of omental buldge into vagina may need excision of excess omentum after incising anterior vaginal wall. Various procedures have been tried to create new urethera using microvascular, free radial forearm flap, buccal mucosa, a combined free autologous bladder mucosal and/or skin graft, vascularized tube flap of tunica vaginalis, lyophilized human dura, synthetic absorbable device etc. (please refer Table 2).

In cases of primary failure and/or long urethral strictures and/or traumatic defects of urethera, scientists are attempting alternative methods. In a few cases, use of absorbable synthetic material has shown good results experimentally. However, even though absorbable, it is a foreign body and clinical trials are still awaited.

Scientific rational for use of peritoneum in the present invention:

In the developing embryo the urogenital sinus is seperated from rectal part of cloaca by mesodermal septum, "the uro-rectal septum," which is developed from intermediate cell mass mesoderm of embryo. This septum divides original cloacal membrane into urogenital and anal membrane. Similarly, the trigone of urinary bladder, posterior urethera, smooth muscle and connective tissue of urethera in both sexes are developed from mesoderm Based on the embryonal principles described earlier and the capacity of the stem cells of peritoneum of mesodermal origin from embryonal contiguous regions to undergo needed change by desired metaplastic transformation, the inventor for the first time identified that peritoneum from suitable site is the best material for use as an interpositional tissue.

Triagone of urinary bladder and posterior urethra developed from absorbed mesonephric ducts while the anterior part of posterior urethra, prostatic and membrances urethra are formed by the primitive and definitive urogenital sinus. But mesoderm forms muscle and connective tissue of urethra. The Epithelium of the urinary tract has the capacity to grow by extension even on artificial scaffolding.(Osler L. et al, Scand. J. Urol Nephrol. 1992=199=26). Therefore, the peritoneum from mesoderm germ layer is the best suited material for urethoplasty of posterior urethra.

Urorectal septum (FIGS. 33 to 35 of the drawings) separates urethra, urinary bladder, anal canal rectum, and genital tract from each other. This septum forms the intervening connective, fatty and loose aerolar tissue in the region. This is of mesodermal origin and therefore, peritoneum which is also of mesodermal origin having stem cells capable of undergoing desired metaplasia is most suitable material (physiologically and embryologically) as an interpositional tissue to separate urethra, urinary bladder on one side and rectum, vagina on other side, Peritoneum for interpositional purpose provides natural physiological covering. It has all qualities like that of omentum. In addition, it has fast healing capacity, infection resistant property, haematoma preventing property and it helps in healing in a speedy way. It holds sutures extremely well and the subperitoneal tissue has lymphatic plexus and rich plexus of capillaries if used in continuity with sufficient subperitoneal tissue. All these properties of peritoneum are needed to contain the fistula. The stem cell are capable of undergoing metaplastic transformation to adapt to local surroundings. The peritoneum heals by metamorphosis of insitu mesenchymal cells of which it is composed of the large defects heal as rapidly as small defects. Peritoneal defects are restored simultaneously every where and majority of cells involved in peritoneal healing are derived from differentiation of stem cells present within the subperitoneal tissue. Cells shed from intact peritoneum implant in the area of injury and in growth of mesothelial cells from edges of peritoneum are additional mechanism which play minor role in peritoneal healing. In addition, it has infection resistant, haematoma preventing and absorption properties due to its semipermeability.

Further, peritoneal mesenchymal cells with macrophages along with phagocytic activity provide perfect surroundings for healing. Rapid healing properties of peritoneum prevent delay in healing of fibrosed area. Speed of healing is important here as the covering of the defect with viable tissue membrane to prevent subsequent fistula formation which is a notorious complication. The disadvantages of use of omental pedicle graft in the repair of fistula as mentioned above are not seen with the use of peritoneal graft as an interpositional tissue. This technique can be used in the repair of high as well as low variety of fistula. Thus, peritoneum not only helps in promoting healing but also actively takes part in healing. It also has the advantage of having proper basement membrane which is lacking in omentum or irregularly present in the omentum tissues.

The inventor feels that the success of repair of genito urinary rectal fistulae is due to these properties of peritoneum along with meticulous and painstaking dissection of areas of defects.

Though, it is known that peritoneum consists of stem cells of mesodermal origin and is capable of undergoing metaplasia (Rosai Juan, Ackerman's Surgical Pathology C.V. Mosby Co., 1989, Vol. II, CH.26 p. 1638), none of the prior art knowledge suggests or even envisages regeneration of desired organs such as urethra from stem cells of peritoneum.

In a developing embryo, the urogenital sinus is separated from rectal part of cloaca by mesodermal septum—"the uro-rectal septum" developed from intermediate cell mass mesoderm of embryo (please refer FIGS. 33–36 of the drawings). This septum divides original cloacal membrane into urogenital and anal membrane. Similarly, the trigone of urinary bladder, posterior urethra, smooth muscle and connective tissue of urethra in both sexes are developed from mesoderm (Harrison, R. G., Introduction to embryology in Cunningham's text book of anatomy., Edited by G. J. Romanes, Oxford University Press, 1991, p. 576). The above knowledge indeed helped the inventor to identify the embryonic contiguous segment of peritoneum to repair/regenerate uro-rectal septum in human beings.

The inventor has now identified that the stem cells of peritoneum from embryonal contiguous regions are capable of undergoing desired metaplastic transformation. Hence, the inventor after much research realised that the peritoneum being a mesodermal origin like that of uro-rectal septum of embryo is the best material for use as an interpositional tissue and for posterior urethroplasty. Posterior urethra in males and almost whole of urethra in female is developed from mesoderm.

The present knowledge of embryology reveals that the part of urethea extending from urinary bladder upto ejaculatory ducts is developed from vesicouretheral canal (FIGS. 33–36 of the drawings). The vasico uretheral canal is separated from hind gut by the developement of urorectal septum (FIGS. 33–35 of the drawings) since this part of urethera is from visco-urethral canal it is of endodermal origin. The posterior wall of this part of urethera is developed from absorbed mesonephric ducts (FIG. 33, and FIGS. 37 to 43 of the drawings—the sagittal and dorsal view of urinary bladder) and hence it is mesodermal in origin. The prostatic urethera, membranous urethera are developed from pelvic part of definitive urogenital sinus. Penile part of urethera (except terminal part) is derived from epithelium of phallic part of definitive urogenital sisus (U.G.S. FIG. 36 of the drawings).

But the musculature and connective tissue of the wall of whole urethera is of mesodermal original (Longman's Medical embryology 7th edition Edited by T. W. Sadler, 1995 published by Williams & Wilkins Baltimore, Philadelphia, Hong Kong, London, P 284).

Thus, it is clear from the above that the trigone and urethera upto ejaculatory ducts is developed from mesoderm. The smooth musculature and connective tissue of wall of whole urethera is of mesodermal origin. The mucosa of urethera and urinary bladder is of endodermal origin. Interestingly, this mucosa has the capacity to grow by extension thus provides lining to the trigone and posterior urethera also. This fact has been proved experimentally (Osler et al. Scand. J. Urol. Nephrol. 1992: 1999: P 26–32). In this experiment, biodegradable absorbable scaffolding has been used. The mucosal lining has grown over the scaffolding by extension and thus provided the mucosal lining to artificial urethral tube.

In other words, epithelium of urinary bladder and urethera in both sexes is of endodermal origin and is capable of growing by extension. The musculature and connective tissue of urethral wall is of mesodermal origin. The separation of urogenital system from the rectal (hind gut) system is accomplished by urorectal septum of mesodermal origin and provides fatty tissue, loose areolar tissue and connective tissue in between urinary tract, genital tract and rectal tract (urological, genital and rectal systems—FIGS. 33–35 of the drawings).

Therefore, mesodermal stem cells of peritoneum from contiguous embryonal segment having proved capacity of metaplastic transformation to desired mesodermal tissues essential in the system is the best material, physiologically, embryologically and developmentally and is an ideal tissue to be used in the area for repair.

In repair of genito urinary fistula, omental pedical graft is commonly used for inter positional purposes, which obviously has disadvantages.

The peritoneum has all qualities like that of omentum and in addition, it has fast healing property, infection resistant property and haematoma preventing property, apart from holding sutures extremely well due to the presence of basement membrane. Therefore, the inventor for the first time realized that the peritoneum for interpositional purpose provides the excellent natural physiological covering and provides tissues in the area as per the embyological development of the region. Further, since uro-rectal septum which is a derivative of mesoderm separates or divides organs such as Bladder, urethra, female genital organs and rectum during embryonal development. Till to date, it is considered that the peritoneum is not a suitable substitute for urinary tract replacement because of probable apprehensions that (a) it was considered as unsuitable as a substitute in urinary tract. (b) Peritoneum is a thin membrane and the tube constructed from it is likely to be compressed and produce obstruction due to surrounding fibrosis etc. (c) Leakage of urine and formation of urinoma in the surrounding area. (d) Free peritoneum is liable for calcification and necrosis. (e) No effective urinary expulsion possible from the tube of peritoneum when it is used as a substitute in urinary tract ureter/urethra etc. and (f) Donor area of peritoneum from peritoneal cavity is likely to form adhesions in the abdominal cavity, infection and fatal peritonitis etc.

Contrary to the above apprehensions and hesitations, the inventor has now invented a method of regenerating or successfully repairing the urethra or urinary tract.

In short, the success of the invention is because the inventor has now identified that peritoneum being the mesodermal derivative, is well suited for interpositional purpose between the repaired organs such as bladder, urethra on one side and vagina and/or rectum on the other side (see FIGS. 45 and 46 of the drawings). Not only this, but also the realization that the capacity of stem cells of peritoneum to undergo desired metaplasia and form needed tissues in the region. In other words, peritoneum has unique property of healing by metamorphosis of in situ mesenchymal cell of which it is composed. This property of peritoneum is utilized in this technique.

Materials and Methods:

The illustrations given herebelow are merely for the purpose of understanding the invention better and these should not be construed to limit the scope of the present invention.

The inventor has now successfully repaired many complex genital urinary rectal fistulae. In a typical case, where a patient of 19 years male was operated earlier elsewhere for repair of fistula. Unfortunately, the earlier attempt resulted in recurrence of genito urinary rectal fistula. FIG. 44 of the drawings shows that the pre-operative retrograde cystourethrogram revealing dye leaking into rectum and surrounding area. The FIGS. 45 and 46 of the drawings show a schematic use of peritoneum for interpositional purpose. FIG. 45 shows perineal view of exposed urethra, prostate and rectum wherein BU refers to Bulbus Urethra and MU as Membranous Urethra, P is Prostrate and A and B as grafts. FIG. 46 of the drawings show the sagittal section of pelvic cavity showing UB as Urinary Bladder, P as Prostate and PS as Pubic Symphysis, SC as Sigmoid Colon, R as Rectum and A and C grafts on bladder and urethra while B is a graft on rectum. The dotted line on the anterior abdominal wall shows the mobilisation of peritoneal strips. In other words, FIG. 46 of the drawings show the use of the present invention wherein strips of peritoneal layer from lower abdomen extending into pelvis were used for interpositional purpose after excision of fistulous track and repair of defects of rectum on one side and the urinary bladder and urethra on the other side. The posterior urethra was ruptured and there was loss of substance of urethra. The margins of urethra were irregular and devitalized needing excision. Thus, further loss of urethral substance was inevitable. Therefore, any direct repair would have resulted in shortening and stricture. For this reason, the inventor adapted urethroplastic method using peritoneum from contiguous embryonal segment i.e. healthy pelvic peritonium. The posterior urethra was reconstructed using free peritoneal graft from healthy pelvic peritoneum for urethroplasty over urethral catheter as a stent. FIG. 47 of the drawings show early post operative cysto urethrogram, clearly indicating the perfect repair of posterior urethra and urinary bladder. There was not leakage of dye in the surrounding area or in the rectum was observed. The presence of air bubbles in the repaired region in urinary bladder and urethra indicates air tight repair of the defect. The late post operative micturating cysto-urotherogram (three years post operative) in a patient of repaired complex genito-urinary fistula indicates good control of the urinary flow (FIG. 48 of the drawings). Urine flow chart (five years post operative) shows good urinary flow rate (FIG. 49 of the drawings).

The success of the above surgery encouraged the inventor and to reconfirm the inference of the above surgical experiment, the inventor subsequently attempted repair of sixteen cases of complex genito urinary/rectal fistula. The peritoneum was used as interpositional tissue in all the sixteen cases and for reconstruction of urethra in seven patients. Eleven cases underwent primary repair and five cases had recurrent fistula previously operated elsewhere. Nine were female and seven were males, their ages ranged between 15 to 30 years. Diagnosis was established by history, clinical examination, routine and special investigation cystourethrogram (FIG. 44 of the drawings), cytoscopic examination whenever possible. The abdominoperineal approach in males and abdominovaginal in females was used for demonstration of defects in urethra, urinary bladder on one side and vagina/rectum on other side. After removal of the urinary catheter/stent retrograde cystourethrogram was performed to see the integrity of the repair and repeated one and five years postoperatively for detecting urethral narrowing or stricture formation. Seven cases were followed for 2–5 years postoperatively. Follow up investigation of micturating cystourethrogram and urinary flow rate studied (FIGS. 48 and 49 respectively of the drawings).

Use of peritoneum

The strip of peritoneum from pelvis extending on to abdominal wall in continuity was used to cover the rectal, vaginal and vesicourethral defects as an interpositional tissue (please refer FIGS. 45 and 46 of the drawings). For urethral tube reconstruction and patch repair of urethra, a free peritoneal graft selected from retrovesical pelvic peritoneum was used. The peritoneum selected was healthy and not involved in scarring. An indwelling catheter in the urethra was used as a stent in those who underwent urethroplasty.

Technique of Repair

Pre-operative preparation

4–6 weeks waiting is helpful if repair has been attempted with faecal or urinary diversion. Bowel preparation with oral metronidezole (400 mg three times a day for 5 days) and saline colonic wash outs (two days) prior to surgery. Urinary tract infection treated with appropriate antibiotics. Urinary diversion is not effective as urine easily leaks out through vagina or rectum as it is the easy way. Urethral catheterization is difficult due to damaged urethra or misdirected distal end of urethra.

Approach

Abdominoperineal or vaginal extraperitoneally approach.

Position

As for synchronous abdominoperineal operation with head end lowered.

Abdominal Part

Incision: Midline suprapublic incision.

Dissection

Urinary bladder reached extraperitonealy and opened by middle vertical incision. If urethral catheterization was not possible then indwelling urethral catheter passed by a rail road method. (Bailey & Love's Short practic e of surgery revised by C. V. Mann. R. C. G. Russell, 21st ed. E.L.B.S. ed. H. K. Levis and co. Ltd. 1991. Ch.48. p. 1100. Rail road technique p.1447) Ureters on both the sides catheterized to protect them in subsequent dissection. By blunt and sharp dissection retrovesical space opened extraperitoneally. Sufficient space is created between rectum and urinary bladder, prostate and urethra in males and between bladder, urethra on one side and the uterus and vagina on the other side in females.

Peritoneal part

Incision: Inverted 'V' shaped incision in males to have "more space" for deep dissection and to "safeguard anal sphincter" (FIG. 50 of the drawings). In females space between urethra and anterior vaginal wall created with blunt and sharp dissection. Space widened with proper haemostasis. A full tunnel is created meeting abdominal dissector. Dissection is carried out here the urethra using the urethral catheter as a guide.

Repair of Urethra

Both the above mentioned dissections are difficult and time consuming and need meticulous care. All the scar tissue is carefully excised. Edges of the rent in urinary bladder, urethra, vagina/rectum need excision and refreshening for better healing. Urethral tissue if refreshed produces a further deficit and direct repair will result in stricture formation. No attempt is made at end to end repair if the tissue is deficient due to ischemia, necrosis as a result of trauma or previous surgery. If only the posterior wall is missing it is bridged with peritonial sheet (from the donor area as described above) over urethral catheter acting as a stent. If the urethral tube is missing then, peritoneum is used to reconstruct the urethra and bridge the defect by making a tube of peritoneum over the urethral catheter using 4/0 vicryl continuous sutures.

Repair of urinary bladder and bladder neck

Every attempt is needed here to preserve the continence mechanism and carefully protect the ureter. The urinary bladder is repaired in longitudinal fashion. This can be easily done from perineal side after retracting vagina/rectum posteriorly. The site of defect is pushed towards the perineal wound by hand in the urinary bladder and with fingers it is displayed in the wound and suturing is easily achieved.

Repair of Vagina and rectum

Repair of vaginal/rectum poses no difficulty and is carried out by a single layer interrupted sutures on the vagina and on the rectum.

Peritoneal flaps

Two flaps raised from parietal peritoneum/each 1" wide. Its length depending upon distance of the defect site from the anterior or posterior abdominal wall (FIG. 46 of the drawings). The strips are brought down into the abdominoperineal tunnel. One strip is used to cover the defects in the rectum or vagina (FIGS. 45 and 46 of the drawings). Free peritoneum from retrovesical area of pelvis and posterior abdominal wall used for urethral reconstruction and urethroplasty. This part of the peritoneum is considered the contiguous area of mesonephric duct development which forms the trigone and posterior urethra. This part of peritoneum has capacity to undergo desired metaplastic transformation. The repaired areas of urinary tract, genital tract/rectum are covered with these mobilized peritoneal strips on either side (FIGS. 45 and 46 of the drawings), in urethral repair and urethroplasty, care being taken to keep the serosal surface of the peritoneum towards urethral lumen as this surface undergoes metaplasia. The abdominal wall surface of the peritoneum is kept away from the viscera as this carries lymphatics and blood vessles. Free drainage of urine from both supra pubic and urethral catheter is very important during the immediate postoperative period. Urethral catheter as stent is important when some form of urethroplasty is carried out and left in situ for 3–6 weeks for safe healing. Postoperatrive retrograde cystourethrogram is performed to determine the integrity of repair (FIG. 47 of the drawings).

Peritoneum from the pelvis and anterior abdominal wall used as an interpositional tissue to cover area after repair of complex genito urinary rectal fistula in sixteen patients. Eleven cases underwent primary repair and five cases had undergone initial repair elsewhere. Three patients needed urethral wall repair. In four patients, a urethral tube was reconstructed. The fistulous tract was closed successfully in all the cases. Urinary tract infection persisted upto two months post operatively in two patients. They responded well to antibiotic treatment. Initially urinary incontinence was present in 14 patients as the injury was noted at the neck of urinary bladder. This was successfully treated by perineal exercises. One case had initial difficulty in starting the act of micturition which improved subsequently without any intervention. The suprapublic catheter was kept for a maximum period of 2 weeks and urethral catheter up to 4 weeks. In urethral reconstruction, the catheter was kept for a period of 6 weeks. When the colostomy was performed in patients with rectal injury, which was closed 6–8 weeks post operatively after establishment of satisfactory repair of the fistulous defect and satisfactory report of post operative cystourotherogram (FIG. 47 of the drawings). In seven cases where urethral reconstruction was done, there was no need for urethral dilation as repaired area appeared wide on cystourethrogram (FIG. 47 of the drawings). There was no evidence of stricture up to 2–5 years of post operative follow up.

Urinary flow studies were satisfactory. In one patient who had undergone hysterectomy for fibroid uterus four years after fistula repair. She still has a leak of one or two drops of urine after very severe stress, for example, like severe bout of cough or severe sneeze. Otherwise the patient is fully continent and satisfied (FIG. 49 of the drawings).

The above description establishes beyond any doubt that the inventor has successfully regenerated human body parts such as ureter and uro-rectal septum.

Regeneration of Abdominal Wall Aponeurosis

As discussed earlier, reparative regeneration is a constant endeavour in nature's life processes. It is maximum in plants and lower forms of life. Regeneration is minimum or even absent in higher forms of life, mammals and man. This is because of the specialization and maintenance of specialisation of stem cells to perpetuate life in higher animal forms.

In fact, the results of animal experimental study of conversion of stem cells of peritoneum into aponeurosis is tried and successfully achieved in abdominal wall in the present invention. The term 'aponeurosis' means flat tendon of flat muscles in the body, for example, the flat muscles of the anterior abdominal wall such as external abdominis muscle, internal abdominis muscle and transverus abdominis muscle form aponeurosis in the anterior abdominal wall and this tendon is now regenerated as per the present invention.

In the present experiment, anterior abdominal wall peritoneum correspondent to the somite segment of that region was transferred and sutured in the excised part of the aponeurosis of the abdominal wall in dogs as shown in FIGS. 55 and 56 of the accompanying drawings. Biopsy of the grafted area after 3 months of the post-operative period revealed conversion of peritoneal graft into the aponeurosis. The embryonic principle employed in the present invention is explained in FIGS. 51 to 54 of the accompany drawings. In FIG. 51 of the drawings, 'P' represents the parexial mesoderm which forms somite. This somite undergoes subdivisions into dermatome, myotome, and sclerotome as shown in FIG. 52 of the drawings (enlarged view of somite). Sclerotome forms vertebral column segments and Myotome is shown with segmental nerve supply as in FIG. 53 of the drawings. On folding of the germ disk the myotome also migrates anteriorly alongwith coelomic cavity epithelium of the lateral plate mesoderm. Thus, explaining the contiguous area of the peritoneum in the embryonal development of anterior abdominal wall (FIGS. 53 and 54 of the drawings).

During the course of the peritoneal experiments, the inventor has observed that using peritoneum from random places other than embryonal segments, landed in failure to regenerate the desired tissues. For example, the blood vessels, in fact, develop from wandering mesenchymal cells and hence, the peritoneum from anterior and/or posterior wall failed to regenerate proper blood vessel formation.

In addition, the inventor observed that the use of peritoneal graft along with muscle and fascia interferes with the effective stimulation and induction of differentiation of stem cells present in the peritoneal layer to the desired metaplasia. Therefore, the thin layer of peritoneum, i.e., single celled layer on basement membrane (not with muscle or fascia) is utilized by the inventor in his experiments.

The present invention is based on experiments on seven mongrel dogs. A suitable embryonal segment of autogenous peritoneum was excised and transferred to rectus sheath region. The gross appearance of the grafted membrane, after three months post operative period, revealed a tough and thick tissue formation. The histology confirmed the collagen fiber tissue in layers similar to aponeurosis in the grafted peritoneum membrane.

Materials and Method

The following examples are mainly illustrative to understand the invention easily and clearly but not to restrict the scope of the invention.

The laid down standards and guide lines by animal ethical committee for the care and use of animals were strictly followed.

Seven Mongrel dogs, 4 males and 3 females, of 3–7 years of age approximately, weighing 6 to 8 kg. body weight were used in the experiment, after 10 to 15 days of quarantine period.

Operations performed under general anaesthesia using sodium pentobarbitone (40 mg/kg body weight) and with perioperative antibiotic cover. The abdomen wall was opened by mid line incision 10 cms to 12 cms long in supra umbilical region (2 dogs), infra umbilical region (3 dogs) and at umbilical region (2 dogs). The peritoneum about 5 cms to 7 cms long and 4 cms to 6 cms wide, was excised from left side of the incision of the abdominal wall. A similar size of rectus sheath was excised from right side of the abdominal incision. The peritoneal patch was sutured in place of excised rectus sheath using 5/o Vicryl suture (FIGS. 55 and 56 of the drawings) the serosal aspect of perital peritoneum was kept facing rectus muscle. The abdominal incision was closed in layers.

The grafted peritoneum region was re-explored after 3 months post operative period. The gross appearance was noted. The histology of the graft was studied under Haematoxylene-Eosin stain and also under Masson's trichrome stain.

The post operative period of all the seven dogs was uneventful, except in two dogs. There was some stitch infection in these dogs and needed post-operative antibiotic therapy. In rest of the five dogs, the peri-operative antibiotic shot was sufficient.

On re-exploration after three months of post operative period, the grafted peritoneum membrane was found to be thickened and tough. There were mild adhesions on either side of the grafted membrane. The adhesions were more marked in two dogs where stitch infection was observed. There was no collection of pus, inflammatory exudate, seroma or haematoma formation in the grafted peritoneum region in any of the seven dogs. The gross examination revealed that the grafted thin membrane of peritoneum was thickened greyish white tissue. This change was seen through out the length and breadth of the graft. The serial sections of the graft were stained with haematoxylene-eosin stain and with Massons' trichrome stain for better demonstration of connective tissue and collagen fiber tissue.

H & E stain (10×6.3 magnification) showed eosinophilic collagen tissue arranged as dense parallel wavy fibrous structures of variable lengths and widths in different layers (FIG. 57 of the drawings). The thick eosinophilic collagen structures of different size and shape cut longitudinally and transverely. The irregularly shaped bundles in different layers are shown in FIG. 58 of the drawings. Masson's trichrome stain (25×6.3 magnification) showed light green stained collagen fibers arranged as parallel wavy structures. The transverse cut bundles of the collagen fibers are shown in (FIG. 59 of the drawings).

Embryonic Principle underlying the invention

These transformed structures described above are derived from embroynal germ layer mesoderm. Therefore, the mesodermal stem cells have capacity to form mesodermal tissues. The aponeurosis of flat muscles of the abdomen is a derivative of germ layer mesoderm (Harrison R. G., Cunningham's Text Book of Anatomy, 12th Reprinted by G. J. Romanis, Oxford University Press, Oxford N.Y. Toronto. P.15: 1991). Therefore, the peritoneum is used in this experiment to regenerate aponeurosis.

It is known that once a single celled ovum is fertilized by the sperm it acquires a tremendous capacity to form all the body tissues and organs. The body tissues and organs are formed from the germ layer cells of ecto, endo and mesoderm of germlayer disc of developing embryo (FIG. 1 of the drawings)) The mesoderm differentiates into paraxial, intermediate cell mass, and lateral plate mesoderm. A coelomic cavity developes in lateral plate mesoderm. The lining of this intra embryonic coelem forms peritoneum. The paraxial mesoderm forms somites of the embryo. These somites subdivide into dermatome, myotome and sclerotome (FIG. 52 of the drawings). The myotome of the somite migrates lateroventrally and on folding of the germ disc comes to lie in contiguous region to intra embryonic coelemic and together forms the coelomic wall. This forms the muscular wall of the abdominal cavity, lined with peritoneum. Thus it is clear that the mytome of the somite develops in contiguous region to peritoneum and joins the counter part in the mid line (FIG. 54 of the drawings). The cells of the somites and peritoneum are the same cells of the mesoderm of germ disc of developing embryo. But due to location and functional need of the region these cells become different tissues, the peritoneum and sheet muscles. The peritoneum preseves stem cells with pluripotent capacity and can undergo metaplasia as explained earlier. The surgical technique in the present experiment provides changed new location, surrounding and functional need of the aponeurotic tissue system and forcing a new demand on stem cells to differentiate and proliferate into desired tissue locally. It is now known that the vertebrate development is a process driven mainly by cellular interaction rather than direct genetic instructions. The process of development are capable of disturbance by environmental factors (Schmid, P., Cox. D. Bilbe; G "Differential expression of TGF, B1, B2, & B3 genes during mouse embryogenesis" Development 1991=111=117: Berry, C. L. "The molecular basis of development" Progress in pathology, ed by Nigel Kirkham & Peter Hall, Published by Chuchil Livingstgon Med. Div., Longman group Ltd. 1995: Vol I, Ch.7. p. 121). The peritoneal membrane sutured in rectus sheath region is subjected to pull, traction, stress and strain exerted by the respiratory movements, distention of abdomen and muscular activity of the abdominal wall muscles. It is demonstrated in the literature that the functional load augments the presence of fibrils in regenerating tendinous tissues (Envemeka C. S. "Membrane bound intra cellular collagen fibrils fibroblast & myofibroblast of regenerating rabbit calcaneal tendons "Tissue Cell. 1991=23(2)=73=1191). The collagen growth is helped by the fibroblast traction mechanism (Harris, A. K. Stopak, D. Wild, P. "Fibroblast traction as a mechanism for collegen morphogenesis. Nature. 1981=290=249). The mesodermal component of skin is responsible for pattern regulation of regenerating exolotl limb. (Tortensen, T. A. Meen, H. D. Steris, M. "The effect of medical exercise therapy on a patient with chronic supraspinatous tendinities "Diagnonstic ultra sound: Tissue regeneration A case study" J. Orthop. Sports Phys. Ther. 1994=20(6)=319). Probably all these factors are responsible for the formation of aponeurosis in the grafted peritoneal membrane. Even though tendon and aponeurosis are low metabolic structures, they show regeneration in lower forms of life and in man as well as shown in supra spinatous tendinitis (Holder N. "Organisation of connective tissue pattern by dermal fibroblastin the regeneration of axolotl limb. Development 1989=105=585). The result of the present experiment shows on gross appearance and histologically the formation of aponeurosis in the grafted peritoneum. This suggests the transformation of fully developed tissue, the peritoneum into another fully developed tissue, the aponeurosis. This is known as metaplasia (Lugo, M. Putung, P. B.; "Metaplasia" An over view. Arch. Pathol. Lab. Med 1984=108=185). Since this change is very much needed for morhologically, anatomically and functionally in the region, it can appropriately be termed as: "desired metaplasia".

In a prior art entitled "A New Technique of Marlex-peritoneal Sandwich in the Repair of Large Incisional Hernia" (Matapurkar B. G. et al World Journal of Surgery 1991, 15, 768 to 770), a technique using "Marlex Peritoneal Sandwich" in repair of hernia has been disclosed. Though, the above technique employed two peritoneal layers sandwiching Marlex mesh to repair incisional hernia, yet the above disclosure does not envisage or even suggest the regeneration of aporneurosis now disclosed in the present invention. In fact, the above prior art neither mentions use of stem cells nor the specific characteristics features (properties) of such stem cells. Further, there is no indication of employing embryonic contiguous segment of peritoneum in that known art, which is an essential aspect of the present invention. In fact, the above prior art is merely for the repair of incisional hernias using a synthetic mesh but never discloses the regeneration of aponeurosis which is affected by any kind of ailments such as damage of muscle due to trauma, accident, gum-shot wounds, blast injury, tumour infiltration, repeated surgery at the same site etc. Furthermore, the required metaplastic transformation of aponeurosis (desired metaplasia) i.e. the complete regeneration of aponeurosis was not achieved or even observed in the prior art as fully achieved in the present invention. In addition, only a single layer of peritoneum is used in the present invention as opposed to use of two layers of peritoneum in the prior art. Moreover, the principle of providing a functional need to the Marlex-peritoneal sandwich was not envisaged in the prior art. In the technique of Marlex peritoneal sandwich, use of free-peritoneum i.e. single cellular peritoneal layer without muscle or fascia was not identified and used as it has been done successfully in the present invention to achieve the total regeneration of aporneurosis.

The inventor indeed was able to successfully regenerate/repair the organs in human beings.

What is claimed is:

1. An in vivo and in situ method of organogenesis of various tissues or organs in a mammalian body, comprising steps of surgically transferring an autogenous peritoneal segment containing stem cells, said segment being selected from a corresponding contiguous embryonal region of the body that is away from the site where the organ or tissue is to be regenerated and providing a new functional need and a new tissue environment for regeneration of the desired tissue or organ.

2. A method as claimed in claim 1, wherein organogenesis of various tissues or organs involves repair or regeneration of such tissues or organs.

3. A method as claimed in claim 1 wherein the autogenous peritoneum is shifted by surgical technique to provide the proper cell movements to the desired site for regeneration of required tissue or/organ.

4. A method as claimed in claim 1 wherein the peritoneum used is a single stem celled layer on a basement membrane.

5. A method as claimed in claim 1, wherein an intrinsic factor such as messenger gene and genetic factor, inherent in the stem cells is exploited for the regeneration of the required tissue or organ.

6. A method as claimed in claim 1 which includes creating a stress of new functional need of a tissue system of new location to which the stem cells have been shifted, to induce desired metaplasia.

7. A method as claimed in claim 1 wherein a peritoneal layer is exclusively peritoneal membrane devoid of any muscle or fascia.

8. A method as claimed in claim 1 wherein the organ or tissue to be regenerated is selected from the group consisting of ureter, fallopian tube, uterus, uro-rectal septum, urethra, trigone and aponeurosis.

9. A method as claimed in claim 1 wherein the organogenesis or various tissues or organs incorporates functions of tissue inducers and/or tissue organizers to achieve regeneration/repair of any tissue or organ into its proper size, shape and form to perform its inherent function.

10. A method as claimed in claim 1 wherein a serosal surface of peritoneum is kept towards a lumen of the organ to be regenerated or repaired.

11. A method as claimed in claim 1 wherein a time period of 2 to 5 months is provided for the regeneration of organs or tissues from a grafted peritoneum.

12. A method as claimed in claim 1 wherein the organ is ureter a which is regenerated from a free peritoneal tube graft obtained from infra umbilical region just anterior to caecum and ascending colon extending downwards towards pelvis.

13. A method as claimed in claim 12 wherein cut ends of the ureter are spatulated before anastomosis with free ends of a peritoneal tube graft.

14. A method as claimed in claim 13 wherein a support is placed inside a free peritoneal graft tube to counter act abdominal pressure exerted on retro-peritoneal space.

15. A method as claimed in claim 12 wherein a support stent which is a tubular structure having a blunt-closed end placed towards a kidney and having an opening just below the blunt end, and an open end towards a urinary bladder is used to discharge the urine in the bladder, and the stent has perforations on side walls used to permit urine to come in contact with a graft and to allow excess urine to return back to a stent cavity.

16. A method as claimed in claim 12 wherein regeneration of ureter occurs in 2 to 5 months period.

17. A method as claimed in claim 12 wherein the regeneration of ureter occurs due to new functional need to which the stem cells of the free peritoneal graft is subjected to.

18. A method as claimed in claim 12 wherein the regeneration of the ureter from a peritoneal membrane graft occurs due to new tissue environment of the urinary tract.

19. A method as claimed in claim 1 wherein the organ to be regenerated is a fallopian tube which is being regenerated from a free peritoneal tube graft obtained from pelvic and posterior abdominal wall region.

20. A method as claimed in claim 19 wherein a stent is placed inside a free peritoneal graft tube as a support.

21. A method as claimed in claim 20 wherein the stent which is placed as a support passes through a uterus into a vagina and is secured into a vagina.

22. A method as claimed in claim 19 wherein the regeneration of fallopian tube takes place in 2 to 5 months time.

23. A method as claimed in claim 19 wherein cilia formation is observed in the inner layer of the regenerated fallopian tube and such formation is enhanced by the administration of a hormone such as estrogen in a manner known per se.

24. A method as claimed in claim 19 wherein the ends of the tubular graft and the fallopian tube are spatulated before anastomosis to avoid constriction at the anastomosed site.

25. A method as claimed in claim 1 wherein the organ to be regenerated is a uterus, a donor peritoneum being selected from pelvic peritoneum posterior to uterus extending on to the posterior abdomenal wall.

26. A method as claimed in claim 25 wherein a suitable support or stent being kept inside a tubular graft of the uterus preventing collapse of a grafted tube.

27. A method as claimed in claim 25 wherein the uterine artries on either side of the uterus are preserved and kept intact to provide blood supply to the unexcised part of the uterus.

28. A method as claimed in claim 25 wherein the duration of regeneration of uterus is from 2 to 5 months.

29. A method as claimed in claim 1 wherein the organ to be regenerated is uro-rectal septum for interpositional purpose, a peritoneal graft is selected from pelvic and parietal peritoneum.

30. A method as claimed in claim 1 wherein organs to be regenerated is urethra, the peritoneal graft for urethroplasty is selected from retrovescical peritoneum extending on posterior abdominal wall.

31. A method as claimed in claim 29 wherein two flaps of the size depending upon the distance of the defective site in pelvis from the anterior abdomenal wall, are obtained from parietal peritoneum and brought down in an abdomino-perineal tunnel which is surgically created to facilitate the repair, one of said flaps being used to cover the required defects of the rectum and/or vagina and the other of said flaps is being used to cover the repaired defect of urinary bladder and urethra.

32. A method as claimed in claim 29 wherein abdomino-perineal tunnel is created in male human being by providing inverted V-shaped incision to afford more space for deep dissection and to safeguard anal sphincter.

33. A method as claimed in claim 29 wherein a abdomino-vaginal tunnel is created in female human being by providing incision in the vagina and there by creating a space between urethra and anterior vaginal wall.

34. A method as claimed in claim 1 wherein the organ to be regenerated or repaired is a trigone, urethrial reconstruction or urethero plasty is performed employing the free peritoneum from retrovesiular pelvic and posterior abdomenal wall.

35. A method as claimed in claim 29 wherein the visceral aspect of peritoneum is placed towards the part to be regenerated or repaired in uro-rectal spetum.

36. A method as claimed in claim 30 wherein the visceral aspect of the peritoneum is placed towards the urethral lumen.

37. A method as claimed in claim 1 wherein the organs to be regenerated is aponeurosis which is regenerated from the peritoneal graft obtained from anterior abdominal wall developed from corresponding somite division.

38. A method as claimed in claim 37 wherein the regeneration occurs in 3 to 5 months period.

39. A method as claimed in claim 37 wherein the regenerating aponeurosis is being subjected to the pull and drag due to muscular activity of the abdominal muscles, abdominal distension, constant movements of the abdominal wall due to respiration, in order to impart the required strength to the regenerating aponeurosis.

* * * * *